(12) United States Patent
Yao et al.

(10) Patent No.: US 11,302,421 B2
(45) Date of Patent: Apr. 12, 2022

(54) DATA STORAGE USING PEPTIDES

(71) Applicant: THE HONG KONG POLYTECHNIC UNIVERSITY, Hong Kong (CN)

(72) Inventors: Zhongping Yao, Hong Kong (CN); Cheuk Chi Albert Ng, Hong Kong (CN); Haidi Yin, Hong Kong (CN)

(73) Assignee: THE HONG KONG POLYTECHNIC UNIVERSITY, Hong Kong (CN)

( * ) Notice: Subject to any disclaimer, the term of this patent is extended or adjusted under 35 U.S.C. 154(b) by 0 days.

(21) Appl. No.: 16/949,047

(22) Filed: Oct. 12, 2020

(65) Prior Publication Data

US 2021/0090688 A1 Mar. 25, 2021

Related U.S. Application Data

(63) Continuation-in-part of application No. 16/224,957, filed on Dec. 19, 2018.

(Continued)

(51) Int. Cl.
*G16B 50/40* (2019.01)
*G06F 16/245* (2019.01)
*G16B 50/50* (2019.01)

(52) U.S. Cl.
CPC .............. *G16B 50/40* (2019.02); *G16B 50/50* (2019.02); *G06F 16/245* (2019.01)

(58) Field of Classification Search
CPC ...... G06N 3/123; G11C 13/02; G11C 13/004; G11C 13/0069; G11C 13/0019;
(Continued)

(56) References Cited

U.S. PATENT DOCUMENTS 6,653,076 B1 * 11/2003 Franza, Jr ................ C12Q 1/02
424/9.1
2005/0053968 A1 * 3/2005 Bharadwaj ............. G16B 30/00
435/6.12
(Continued)

FOREIGN PATENT DOCUMENTS

CN 101123497 A 2/2008
WO 20170189914 A1 11/2017

OTHER PUBLICATIONS

Nemzer, Louis R., "A binary representation of the genetic code", Biosystems, vol. 155, May 2017, pp. 10-19 (Year: 2017).*
(Continued)

*Primary Examiner* — Ajay Ojha
(74) *Attorney, Agent, or Firm* — S&F/WEHRW

(57) ABSTRACT

Methods and systems for storing digital data into peptide sequences and retrieving digital data from peptide sequences are disclosed. The method for storing digital data into peptide sequences may include: encoding the digital data into a digital code; translating the digital code into the peptide sequences; and synthesizing the translated peptide sequences. The method for retrieving digital data from peptide sequences may include: sequencing and determining an order of the peptide sequences; converting the peptide sequences with the determined order into a digital code; and decoding the digital data from the digital code. Codes with error-correction capability are developed for encoding digital data into peptide sequences, and a computational method implemented in a software is developed for sequencing the digital data bearing peptides.

28 Claims, 29 Drawing Sheets

Specification includes a Sequence Listing.

Related U.S. Application Data

(60) Provisional application No. 62/657,026, filed on Apr. 13, 2018.

(58) Field of Classification Search
CPC ...... G06F 11/10; G06F 16/245; G06F 16/258; G06F 16/2237; G06F 11/1048; G16B 99/00; G16B 50/40; G16B 50/50; G16B 50/00; C12N 15/00
See application file for complete search history.

(56) References Cited

U.S. PATENT DOCUMENTS

| | | | |
|---|---|---|---|
| 2018/0045721 A1* | 2/2018 | Goodrich | C07K 1/13 |
| 2018/0253563 A1* | 9/2018 | Peck | G16B 50/00 |
| 2020/0348308 A1* | 11/2020 | Chee | C40B 40/10 |

OTHER PUBLICATIONS

Extended European Search Report of EP application No. 18914399.3 issued from the European Patent Office dated Nov. 17, 2021.

\* cited by examiner

800

A mixture of peptides

↓ LC separation

LC chromatogram

↓ MS/MS analysis

MS/MS Spectra

↓ Data analysis by the software 1200

Peptide sequences
(43 18-mer peptides)

```
FSSFSYTLTFLASAEAER
FS[ET]YSSYLYELATLSYR
..........................
PALSSEYVTAASSVFLSR
P[SLE]ATEFTFETESL[YT]R
```

↓ Converting 504

Digital code with error-correction codes
(43 lines of 16 triplets of bits)

```
000 000 111 000 011 001 110 001 111 110 100 000 100 010 100 010
000 [010 001] 011 000 000 011 110 011 010 110 100 001 110 000 011
..........................
100 110 000 000 010 011 101 001 100 100 000 000 101 111 110 000
[000 110 010] 100 001 010 111 001 111 010 001 010 000 110 [011 001]
```

↓ Elimination by scoring

Digital code
(40 lines of 16 triplets of bits)

```
000 000 111 000 011 001 110 001 111 110 100 000 100 010 100 010
000 010 001 011 000 000 011 110 011 010 110 100 001 110 000 011
..........................
100 110 000 000 010 011 101 001 100 100 000 001 000 010 010 000
```

↓ Decoding 506 (by 700)

Digital data

香港理工大學，八十周年校慶；開物成務，勵學利民。
The Hong Kong Polytechnic University, 80th anniversary.

Without error correction
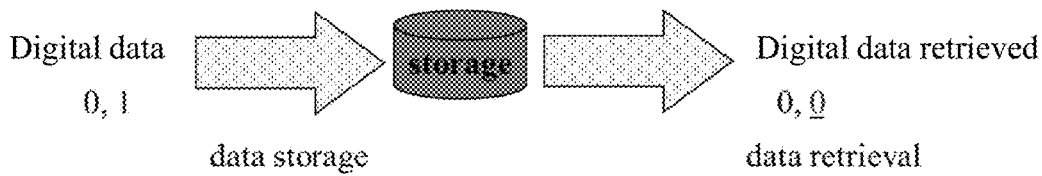
With error correction
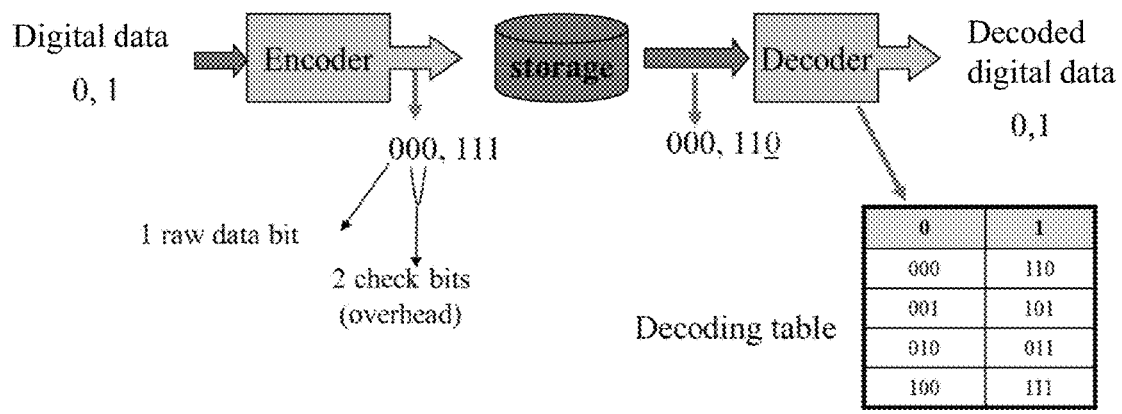
FIG. 10
1000
| Bit | Amino acid mapping |
|---|---|
| 0 | A |
| 1 | T |
FIG. 11A
| Bits | Amino acid mapping |
|---|---|
| 000 | A |
| 001 | T |
| 010 | L |
| 011 | V |
FIG. 11B
| Symbol | Amino acid mapping |
|---|---|
| 0 | A |
| 1 | T |
| 2 | L |
| 3 | V |
| 4 | E |
| 5 | H |
| 6 | Y |
| 7 | F |
FIG. 11C
| Symbol | Amino acids mapping |
|---|---|
| 0 | AAA |
| 1 | AAT |
| 2 | ATA |
| 3 | ATT |
| 4 | TAA |
| 5 | TAT |
| 6 | TTA |
| 7 | TTT |
FIG. 11D
| Symbols | Amino acid mapping |
|---|---|
| 00 | A |
| 01 | T |
| 02 | L |
| 10 | V |
| 11 | E |
| 12 | H |
| 20 | Y |
| 21 | F |
| 22 | D |
FIG. 11E

| Symbols | Amino acids mapping |
|---|---|
| 00 | AAA |
| 01 | AAT |
| 02 | AAL |
| 03 | AAV |
| 04 | ATA |
| 05 | ATT |
| 06 | ATL |
| 07 | ATV |
| 10 | ALA |
| 11 | ALT |
| 12 | ALL |
| 13 | ALV |
| 14 | AVA |
| 15 | AVT |
| 16 | AVL |
| 17 | AVV |
| 20 | TAA |
| 21 | TAT |
| 22 | TAL |
| 23 | TAV |
| 24 | TTA |
| 25 | TTT |
| 26 | TTL |
| 27 | TTV |
| 30 | TLA |
| 31 | TLT |
| 32 | TLL |
| 33 | TLV |
| 34 | TVA |
| 35 | TVT |
| 36 | TVL |
| 37 | TVV |
| 40 | LAA |
| 41 | LAT |
| 42 | LAL |
| 43 | LAV |
| 44 | LTA |
| 45 | LTT |
| 46 | LTL |
| 47 | LTV |
| 50 | LLA |
| 51 | LLT |
| 52 | LLL |
| 53 | LLV |
| 54 | LVA |
| 55 | LVT |
| 56 | LVL |
| 57 | LVV |
| 60 | VAA |
| 61 | VAT |
| 62 | VAL |
| 63 | VAV |
| 64 | VTA |
| 65 | VTT |
| 66 | VTL |
| 67 | VTV |
| 70 | VLA |
| 71 | VLT |
| 72 | VLL |
| 73 | VLV |
| 74 | VVA |
| 75 | VVT |
| 76 | VVL |
| 77 | VVV |

FIG. 11F

| Bit | Previous bit-to-amino-acid mapping | |
|---|---|---|
| | A | T |
| 0 | T | A |
| 1 | A | T |

FIG. 11G

| Bit | Amino acid that the last bit 0 mapped to | | | | Amino acid that the last bit 1 mapped to | | | |
|---|---|---|---|---|---|---|---|---|
| | A | T | L | V | E | H | Y | F |
| 0 | T | L | V | A | - | - | - | - |
| 1 | - | - | - | - | H | Y | F | E |

FIG. 11H

| Bit | Amino acid that the last bit 0 mapped to | | | | Amino acid that the last bit 1 mapped to | | | |
|---|---|---|---|---|---|---|---|---|
| | A | T | L | V | E | H | Y | F |
| 0 | - | - | - | - | A | T | L | V |
| 1 | E | H | Y | F | - | - | - | - |

FIG. 11I

| Bit | Amino acid that the last bit 0 mapped to | | | | Amino acid that the last bit 1 mapped to | | | |
|---|---|---|---|---|---|---|---|---|
| | A or T | | L or V | | E or H | | Y or F | |
| | Amino acid that the last bit 1 mapped to | | Amino acid that the last bit 1 mapped to | | Amino acid that the last bit 0 mapped to | | Amino acid that the last bit 0 mapped to | |
| | E or H | Y or F | E or H | Y or F | A or T | L or V | A or T | L or V |
| 0 | L | V | A | T | - | - | - | - |
| 1 | - | - | - | - | Y | F | E | H |

FIG. 11J

| Symbol | Previous symbol-to-amino-acid mapping | | | | | | | |
|---|---|---|---|---|---|---|---|---|
| | A | T | L | V | E | H | Y | F |
| 0 | T | L | V | E | H | Y | F | A |
| 1 | L | V | E | H | Y | F | A | T |
| 2 | V | E | H | Y | F | A | T | L |
| 3 | E | H | Y | F | A | T | L | V |
| 4 | H | Y | F | A | T | L | V | E |
| 5 | Y | F | A | T | L | V | E | H |
| 6 | F | A | T | L | V | E | H | Y |
| 7 | A | T | L | V | E | H | Y | F |

FIG. 11K(a)

| Symbol | Previous symbol-to-amino-acid mapping | | | | | | | |
|---|---|---|---|---|---|---|---|---|
| | A | T | L | V | E | H | Y | F |
| 0 | T | L | V | E | H | Y | F | A |
| 1 | L | V | E | H | Y | F | A | T |
| 2 | V | E | H | Y | F | A | T | L |
| 3 | E | H | Y | F | A | T | L | V |
| 4 | H | Y | F | A | T | L | V | E |
| 5 | Y | F | A | T | L | V | E | H |
| 6 | F | A | T | L | V | E | H | Y |

FIG. 11K(b)

| Symbol | Previous symbol-to-amino-acids mapping | | | | | | | |
|---|---|---|---|---|---|---|---|---|
| | AAA | AAT | ATA | ATT | TAA | TAT | TTA | TTT |
| 0 | AAT | ATA | ATT | TAA | TAT | TTA | TTT | AAA |
| 1 | ATA | ATT | TAA | TAT | TTA | TTT | AAA | AAT |
| 2 | ATT | TAA | TAT | TTA | TTT | AAA | AAT | ATA |
| 3 | TAA | TAT | TTA | TTT | AAA | AAT | ATA | ATT |
| 4 | TAT | TTA | TTT | AAA | AAT | ATA | ATT | TAA |
| 5 | TTA | TTT | AAA | AAT | ATA | ATT | TAA | TAT |
| 6 | TTT | AAA | AAT | ATA | ATT | TAA | TAT | TTA |
| 7 | AAA | AAT | ATA | ATT | TAA | TAT | TTA | TTT |

FIG. 11L(a)

| Symbol | Previous symbol-to-amino-acids mapping | | | | | | | |
|---|---|---|---|---|---|---|---|---|
| | AAA | AAT | ATA | ATT | TAA | TAT | TTA | TTT |
| 0 | AAT | ATA | ATT | TAA | TAT | TTA | TTT | AAA |
| 1 | ATA | ATT | TAA | TAT | TTA | TTT | AAA | AAT |
| 2 | ATT | TAA | TAT | TTA | TTT | AAA | AAT | ATA |
| 3 | TAA | TAT | TTA | TTT | AAA | AAT | ATA | ATT |
| 4 | TAT | TTA | TTT | AAA | AAT | ATA | ATT | TAA |
| 5 | TTA | TTT | AAA | AAT | ATA | ATT | TAA | TAT |
| 6 | TTT | AAA | AAT | ATA | ATT | TAA | TAT | TTA |

FIG. 11L(b)

| Symbols | Previous symbols-to-amino-acid mapping | | | | | | | | |
|---|---|---|---|---|---|---|---|---|---|
| | A | T | L | V | E | H | Y | F | D |
| 00 | T | L | V | E | H | Y | F | D | A |
| 01 | L | V | E | H | Y | F | D | A | T |
| 02 | V | E | H | Y | F | D | A | T | L |
| 10 | E | H | Y | F | D | A | T | L | V |
| 11 | H | Y | F | D | A | T | L | V | E |
| 12 | Y | F | D | A | T | L | V | E | H |
| 20 | F | D | A | T | L | V | E | H | Y |
| 21 | D | A | T | L | V | E | H | Y | F |
| 22 | A | T | L | V | E | H | Y | F | D |

FIG. 11M

| Symbols | Previous symbols-to-amino-acids mapping | | | | | | | | | | | |
|---|---|---|---|---|---|---|---|---|---|---|---|---|
| | AAA | AAT | AAL | AAV | ATA | ATT | ATL | ATV | ALA | ALT | ALL | ALV | ... |
| 00 | AAT | AAL | AAV | ATA | ATT | ATL | ATV | ALA | ALT | ALL | ALV | AVA | ... |
| 01 | AAL | AAV | ATA | ATT | ATL | ATV | ALA | ALT | ALL | ALV | AVA | AVT | ... |
| 02 | AAV | ATA | ATT | ATL | ATV | ALA | ALT | ALL | ALV | AVA | AVT | AVL | ... |
| 03 | ATA | ATT | ATL | ATV | ALA | ALT | ALL | ALV | AVA | AVT | AVL | AVV | ... |
| 04 | ATT | ATL | ATV | ALA | ALT | ALL | ALV | AVA | AVT | AVL | AVV | TAA | ... |
| 05 | ATL | ATV | ALA | ALT | ALL | ALV | AVA | AVT | AVL | AVV | TAA | TAT | ... |
| 06 | ATV | ALA | ALT | ALL | ALV | AVA | AVT | AVL | AVV | TAA | TAT | TAL | ... |
| 07 | ALA | ALT | ALL | ALV | AVA | AVT | AVL | AVV | TAA | TAT | TAL | TAV | ... |
| 10 | ALT | ALL | ALV | AVA | AVT | AVL | AVV | TAA | TAT | TAL | TAV | TTA | ... |
| 11 | ALL | ALV | AVA | AVT | AVL | AVV | TAA | TAT | TAL | TAV | TTA | TTT | ... |
| 12 | ALV | AVA | AVT | AVL | AVV | TAA | TAT | TAL | TAV | TTA | TTT | TTL | ... |
| 13 | AVA | AVT | AVL | AVV | TAA | TAT | TAL | TAV | TTA | TTT | TTL | TTV | ... |
| 14 | AVT | AVL | AVV | TAA | TAT | TAL | TAV | TTA | TTT | TTL | TTV | TLA | ... |
| 15 | AVL | AVV | TAA | TAT | TAL | TAV | TTA | TTT | TTL | TTV | TLA | TLT | ... |
| 16 | AVV | TAA | TAT | TAL | TAV | TTA | TTT | TTL | TTV | TLA | TLT | TLL | ... |
| 17 | TAA | TAT | TAL | TAV | TTA | TTT | TTL | TTV | TLA | TLT | TLL | TLV | ... |
| 20 | TAT | TAL | TAV | TTA | TTT | TTL | TTV | TLA | TLT | TLL | TLV | TVA | ... |
| 21 | TAL | TAV | TTA | TTT | TTL | TTV | TLA | TLT | TLL | TLV | TVA | TVT | ... |
| 22 | TAV | TTA | TTT | TTL | TTV | TLA | TLT | TLL | TLV | TVA | TVT | TVL | ... |
| 23 | TTA | TTT | TTL | TTV | TLA | TLT | TLL | TLV | TVA | TVT | TVL | TVV | ... |
| 24 | TTT | TTL | TTV | TLA | TLT | TLL | TLV | TVA | TVT | TVL | TVV | LAA | ... |
| 25 | TTL | TTV | TLA | TLT | TLL | TLV | TVA | TVT | TVL | TVV | LAA | LAT | ... |
| 26 | TTV | TLA | TLT | TLL | TLV | TVA | TVT | TVL | TVV | LAA | LAT | LAL | ... |
| 27 | TLA | TLT | TLL | TLV | TVA | TVT | TVL | TVV | LAA | LAT | LAL | LAV | ... |
| 30 | TLT | TLL | TLV | TVA | TVT | TVL | TVV | LAA | LAT | LAL | LAV | LTA | ... |
| 31 | TLL | TLV | TVA | TVT | TVL | TVV | LAA | LAT | LAL | LAV | LTA | LTT | ... |
| 32 | TLV | TVA | TVT | TVL | TVV | LAA | LAT | LAL | LAV | LTA | LTT | LTL | ... |
| 33 | TVA | TVT | TVL | TVV | LAA | LAT | LAL | LAV | LTA | LTT | LTL | LTV | ... |
| 34 | TVT | TVL | TVV | LAA | LAT | LAL | LAV | LTA | LTT | LTL | LTV | LLA | ... |
| 35 | TVL | TVV | LAA | LAT | LAL | LAV | LTA | LTT | LTL | LTV | LLA | LLT | ... |
| 36 | TVV | LAA | LAT | LAL | LAV | LTA | LTT | LTL | LTV | LLA | LLT | LLL | ... |
| 37 | LAA | LAT | LAL | LAV | LTA | LTT | LTL | LTV | LLA | LLT | LLL | LLV | ... |
| 40 | LAT | LAL | LAV | LTA | LTT | LTL | LTV | LLA | LLT | LLL | LLV | LVA | ... |
| 41 | LAL | LAV | LTA | LTT | LTL | LTV | LLA | LLT | LLL | LLV | LVA | LVT | ... |
| 42 | LAV | LTA | LTT | LTL | LTV | LLA | LLT | LLL | LLV | LVA | LVT | LVL | ... |
| 43 | LTA | LTT | LTL | LTV | LLA | LLT | LLL | LLV | LVA | LVT | LVL | LVV | ... |
| 44 | LTT | LTL | LTV | LLA | LLT | LLL | LLV | LVA | LVT | LVL | LVV | VAA | ... |
| 45 | LTL | LTV | LLA | LLT | LLL | LLV | LVA | LVT | LVL | LVV | VAA | VAT | ... |
| 46 | LTV | LLA | LLT | LLL | LLV | LVA | LVT | LVL | LVV | VAA | VAT | VAL | ... |
| 47 | LLA | LLT | LLL | LLV | LVA | LVT | LVL | LVV | VAA | VAT | VAL | VAV | ... |
| 50 | LLT | LLL | LLV | LVA | LVT | LVL | LVV | VAA | VAT | VAL | VAV | VTA | ... |
| 51 | LLL | LLV | LVA | LVT | LVL | LVV | VAA | VAT | VAL | VAV | VTA | VTT | ... |
| 52 | LLV | LVA | LVT | LVL | LVV | VAA | VAT | VAL | VAV | VTA | VTT | VTL | ... |
| 53 | LVA | LVT | LVL | LVV | VAA | VAT | VAL | VAV | VTA | VTT | VTL | VTV | ... |
| 54 | LVT | LVL | LVV | VAA | VAT | VAL | VAV | VTA | VTT | VTL | VTV | VLA | ... |
| 55 | LVL | LVV | VAA | VAT | VAL | VAV | VTA | VTT | VTL | VTV | VLA | VLT | ... |
| 56 | LVV | VAA | VAT | VAL | VAV | VTA | VTT | VTL | VTV | VLA | VLT | VLL | ... |
| 57 | VAA | VAT | VAL | VAV | VTA | VTT | VTL | VTV | VLA | VLT | VLL | VLV | ... |
| 60 | VAT | VAL | VAV | VTA | VTT | VTL | VTV | VLA | VLT | VLL | VLV | VVA | ... |
| 61 | VAL | VAV | VTA | VTT | VTL | VTV | VLA | VLT | VLL | VLV | VVA | VVT | ... |
| 62 | VAV | VTA | VTT | VTL | VTV | VLA | VLT | VLL | VLV | VVA | VVT | VVL | ... |
| 63 | VTA | VTT | VTL | VTV | VLA | VLT | VLL | VLV | VVA | VVT | VVL | VVV | ... |
| 64 | VTT | VTL | VTV | VLA | VLT | VLL | VLV | VVA | VVT | VVL | VVV | AAA | ... |
| 65 | VTL | VTV | VLA | VLT | VLL | VLV | VVA | VVT | VVL | VVV | AAA | AAT | ... |
| 66 | VTV | VLA | VLT | VLL | VLV | VVA | VVT | VVL | VVV | AAA | AAT | AAL | ... |
| 67 | VLA | VLT | VLL | VLV | VVA | VVT | VVL | VVV | AAA | AAT | AAL | AAV | ... |
| 70 | VLT | VLL | VLV | VVA | VVT | VVL | VVV | AAA | AAT | AAL | AAV | ATA | ... |
| 71 | VLL | VLV | VVA | VVT | VVL | VVV | AAA | AAT | AAL | AAV | ATA | ATT | ... |
| 72 | VLV | VVA | VVT | VVL | VVV | AAA | AAT | AAL | AAV | ATA | ATT | ATL | ... |
| 73 | VVA | VVT | VVL | VVV | AAA | AAT | AAL | AAV | ATA | ATT | ATL | ATV | ... |
| 74 | VVT | VVL | VVV | AAA | AAT | AAL | AAV | ATA | ATT | ATL | ATV | ALA | ... |
| 75 | VVL | VVV | AAA | AAT | AAL | AAV | ATA | ATT | ATL | ATV | ALA | ALT | ... |
| 76 | VVV | AAA | AAT | AAL | AAV | ATA | ATT | ATL | ATV | ALA | ALT | ALL | ... |
| 77 | AAA | AAT | AAL | AAV | ATA | ATT | ATL | ATV | ALA | ALT | ALL | ALV | ... |

FIG. 11N

| Symbols | Previous symbols-to-amino-acids mapping | | | | | | | | | | |
|---|---|---|---|---|---|---|---|---|---|---|---|
| | ... | AVA | AVT | AVL | AVV | TAA | TAT | TAL | TAV | TTA | TTT | TTL | ... |
| 00 | ... | AVT | AVL | AVV | TAA | TAT | TAL | TAV | TTA | TTT | TTL | TTV | ... |
| 01 | ... | AVL | AVV | TAA | TAT | TAL | TAV | TTA | TTT | TTL | TTV | TLA | ... |
| 02 | ... | AVV | TAA | TAT | TAL | TAV | TTA | TTT | TTL | TTV | TLA | TLT | ... |
| 03 | ... | TAA | TAT | TAL | TAV | TTA | TTT | TTL | TTV | TLA | TLT | TLL | ... |
| 04 | ... | TAT | TAL | TAV | TTA | TTT | TTL | TTV | TLA | TLT | TLL | TLV | ... |
| 05 | ... | TAL | TAV | TTA | TTT | TTL | TTV | TLA | TLT | TLL | TLV | TVA | ... |
| 06 | ... | TAV | TTA | TTT | TTL | TTV | TLA | TLT | TLL | TLV | TVA | TVT | ... |
| 07 | ... | TTA | TTT | TTL | TTV | TLA | TLT | TLL | TLV | TVA | TVT | TVL | ... |
| 10 | ... | TTT | TTL | TTV | TLA | TLT | TLL | TLV | TVA | TVT | TVL | TVV | ... |
| 11 | ... | TTL | TTV | TLA | TLT | TLL | TLV | TVA | TVT | TVL | TVV | LAA | ... |
| 12 | ... | TTV | TLA | TLT | TLL | TLV | TVA | TVT | TVL | TVV | LAA | LAT | ... |
| 13 | ... | TLA | TLT | TLL | TLV | TVA | TVT | TVL | TVV | LAA | LAT | LAL | ... |
| 14 | ... | TLT | TLL | TLV | TVA | TVT | TVL | TVV | LAA | LAT | LAL | LAV | ... |
| 15 | ... | TLL | TLV | TVA | TVT | TVL | TVV | LAA | LAT | LAL | LAV | LTA | ... |
| 16 | ... | TLV | TVA | TVT | TVL | TVV | LAA | LAT | LAL | LAV | LTA | LTT | ... |
| 17 | ... | TVA | TVT | TVL | TVV | LAA | LAT | LAL | LAV | LTA | LTT | LTL | ... |
| 20 | ... | TVT | TVL | TVV | LAA | LAT | LAL | LAV | LTA | LTT | LTL | LTV | ... |
| 21 | ... | TVL | TVV | LAA | LAT | LAL | LAV | LTA | LTT | LTL | LTV | LLA | ... |
| 22 | ... | TVV | LAA | LAT | LAL | LAV | LTA | LTT | LTL | LTV | LLA | LLT | ... |
| 23 | ... | LAA | LAT | LAL | LAV | LTA | LTT | LTL | LTV | LLA | LLT | LLL | ... |
| 24 | ... | LAT | LAL | LAV | LTA | LTT | LTL | LTV | LLA | LLT | LLL | LLV | ... |
| 25 | ... | LAL | LAV | LTA | LTT | LTL | LTV | LLA | LLT | LLL | LLV | LVA | ... |
| 26 | ... | LAV | LTA | LTT | LTL | LTV | LLA | LLT | LLL | LLV | LVA | LVT | ... |
| 27 | ... | LTA | LTT | LTL | LTV | LLA | LLT | LLL | LLV | LVA | LVT | LVL | ... |
| 30 | ... | LTT | LTL | LTV | LLA | LLT | LLL | LLV | LVA | LVT | LVL | LVV | ... |
| 31 | ... | LTL | LTV | LLA | LLT | LLL | LLV | LVA | LVT | LVL | LVV | VAA | ... |
| 32 | ... | LTV | LLA | LLT | LLL | LLV | LVA | LVT | LVL | LVV | VAA | VAT | ... |
| 33 | ... | LLA | LLT | LLL | LLV | LVA | LVT | LVL | LVV | VAA | VAT | VAL | ... |
| 34 | ... | LLT | LLL | LLV | LVA | LVT | LVL | LVV | VAA | VAT | VAL | VAV | ... |
| 35 | ... | LLL | LLV | LVA | LVT | LVL | LVV | VAA | VAT | VAL | VAV | VTA | ... |
| 36 | ... | LLV | LVA | LVT | LVL | LVV | VAA | VAT | VAL | VAV | VTA | VTT | ... |
| 37 | ... | LVA | LVT | LVL | LVV | VAA | VAT | VAL | VAV | VTA | VTT | VTL | ... |
| 40 | ... | LVT | LVL | LVV | VAA | VAT | VAL | VAV | VTA | VTT | VTL | VTV | ... |
| 41 | ... | LVL | LVV | VAA | VAT | VAL | VAV | VTA | VTT | VTL | VTV | VLA | ... |
| 42 | ... | LVV | VAA | VAT | VAL | VAV | VTA | VTT | VTL | VTV | VLA | VLT | ... |
| 43 | ... | VAA | VAT | VAL | VAV | VTA | VTT | VTL | VTV | VLA | VLT | VLL | ... |
| 44 | ... | VAT | VAL | VAV | VTA | VTT | VTL | VTV | VLA | VLT | VLL | VLV | ... |
| 45 | ... | VAL | VAV | VTA | VTT | VTL | VTV | VLA | VLT | VLL | VLV | VVA | ... |
| 46 | ... | VAV | VTA | VTT | VTL | VTV | VLA | VLT | VLL | VLV | VVA | VVT | ... |
| 47 | ... | VTA | VTT | VTL | VTV | VLA | VLT | VLL | VLV | VVA | VVT | VVL | ... |
| 50 | ... | VTT | VTL | VTV | VLA | VLT | VLL | VLV | VVA | VVT | VVL | VVV | ... |
| 51 | ... | VTL | VTV | VLA | VLT | VLL | VLV | VVA | VVT | VVL | VVV | AAA | ... |
| 52 | ... | VTV | VLA | VLT | VLL | VLV | VVA | VVT | VVL | VVV | AAA | AAT | ... |
| 53 | ... | VLA | VLT | VLL | VLV | VVA | VVT | VVL | VVV | AAA | AAT | AAL | ... |
| 54 | ... | VLT | VLL | VLV | VVA | VVT | VVL | VVV | AAA | AAT | AAL | AAV | ... |
| 55 | ... | VLL | VLV | VVA | VVT | VVL | VVV | AAA | AAT | AAL | AAV | ATA | ... |
| 56 | ... | VLV | VVA | VVT | VVL | VVV | AAA | AAT | AAL | AAV | ATA | ATT | ... |
| 57 | ... | VVA | VVT | VVL | VVV | AAA | AAT | AAL | AAV | ATA | ATT | ATL | ... |
| 60 | ... | VVT | VVL | VVV | AAA | AAT | AAL | AAV | ATA | ATT | ATL | ATV | ... |
| 61 | ... | VVL | VVV | AAA | AAT | AAL | AAV | ATA | ATT | ATL | ATV | ALA | ... |
| 62 | ... | VVV | AAA | AAT | AAL | AAV | ATA | ATT | ATL | ATV | ALA | ALT | ... |
| 63 | ... | AAA | AAT | AAL | AAV | ATA | ATT | ATL | ATV | ALA | ALT | ALL | ... |
| 64 | ... | AAT | AAL | AAV | ATA | ATT | ATL | ATV | ALA | ALT | ALL | ALV | ... |
| 65 | ... | AAL | AAV | ATA | ATT | ATL | ATV | ALA | ALT | ALL | ALV | AVA | ... |
| 66 | ... | AAV | ATA | ATT | ATL | ATV | ALA | ALT | ALL | ALV | AVA | AVT | ... |
| 67 | ... | ATA | ATT | ATL | ATV | ALA | ALT | ALL | ALV | AVA | AVT | AVL | ... |
| 70 | ... | ATT | ATL | ATV | ALA | ALT | ALL | ALV | AVA | AVT | AVL | AVV | ... |
| 71 | ... | ATL | ATV | ALA | ALT | ALL | ALV | AVA | AVT | AVL | AVV | TAA | ... |
| 72 | ... | ATV | ALA | ALT | ALL | ALV | AVA | AVT | AVL | AVV | TAA | TAT | ... |
| 73 | ... | ALA | ALT | ALL | ALV | AVA | AVT | AVL | AVV | TAA | TAT | TAL | ... |
| 74 | ... | ALT | ALL | ALV | AVA | AVT | AVL | AVV | TAA | TAT | TAL | TAV | ... |
| 75 | ... | ALL | ALV | AVA | AVT | AVL | AVV | TAA | TAT | TAL | TAV | TTA | ... |
| 76 | ... | ALV | AVA | AVT | AVL | AVV | TAA | TAT | TAL | TAV | TTA | TTT | ... |
| 77 | ... | AVA | AVT | AVL | AVV | TAA | TAT | TAL | TAV | TTA | TTT | TTL | ... |

FIG. 11N (cont'd)

| Symbols | | Previous symbols-to-amino-acids mapping | | | | | | | | | | |
|---|---|---|---|---|---|---|---|---|---|---|---|---|
| | ... | TTV | TLA | TLT | TLL | TLV | TVA | TVT | TVL | TVV | LAA | LAT | ... |
| 00 | ... | TLA | TLT | TLL | TLV | TVA | TVT | TVL | TVV | LAA | LAT | LAL | ... |
| 01 | ... | TLT | TLL | TLV | TVA | TVT | TVL | TVV | LAA | LAT | LAL | LAV | ... |
| 02 | ... | TLL | TLV | TVA | TVT | TVL | TVV | LAA | LAT | LAL | LAV | LTA | ... |
| 03 | ... | TLV | TVA | TVT | TVL | TVV | LAA | LAT | LAL | LAV | LTA | LTT | ... |
| 04 | ... | TVA | TVT | TVL | TVV | LAA | LAT | LAL | LAV | LTA | LTT | LTL | ... |
| 05 | ... | TVT | TVL | TVV | LAA | LAT | LAL | LAV | LTA | LTT | LTL | LTV | ... |
| 06 | ... | TVL | TVV | LAA | LAT | LAL | LAV | LTA | LTT | LTL | LTV | LLA | ... |
| 07 | ... | TVV | LAA | LAT | LAL | LAV | LTA | LTT | LTL | LTV | LLA | LLT | ... |
| 10 | ... | LAA | LAT | LAL | LAV | LTA | LTT | LTL | LTV | LLA | LLT | LLL | ... |
| 11 | ... | LAT | LAL | LAV | LTA | LTT | LTL | LTV | LLA | LLT | LLL | LLV | ... |
| 12 | ... | LAL | LAV | LTA | LTT | LTL | LTV | LLA | LLT | LLL | LLV | LVA | ... |
| 13 | ... | LAV | LTA | LTT | LTL | LTV | LLA | LLT | LLL | LLV | LVA | LVT | ... |
| 14 | ... | LTA | LTT | LTL | LTV | LLA | LLT | LLL | LLV | LVA | LVT | LVL | ... |
| 15 | ... | LTT | LTL | LTV | LLA | LLT | LLL | LLV | LVA | LVT | LVL | LVV | ... |
| 16 | ... | LTL | LTV | LLA | LLT | LLL | LLV | LVA | LVT | LVL | LVV | VAA | ... |
| 17 | ... | LTV | LLA | LLT | LLL | LLV | LVA | LVT | LVL | LVV | VAA | VAT | ... |
| 20 | ... | LLA | LLT | LLL | LLV | LVA | LVT | LVL | LVV | VAA | VAT | VAL | ... |
| 21 | ... | LLT | LLL | LLV | LVA | LVT | LVL | LVV | VAA | VAT | VAL | VAV | ... |
| 22 | ... | LLL | LLV | LVA | LVT | LVL | LVV | VAA | VAT | VAL | VAV | VTA | ... |
| 23 | ... | LLV | LVA | LVT | LVL | LVV | VAA | VAT | VAL | VAV | VTA | VTT | ... |
| 24 | ... | LVA | LVT | LVL | LVV | VAA | VAT | VAL | VAV | VTA | VTT | VTL | ... |
| 25 | ... | LVT | LVL | LVV | VAA | VAT | VAL | VAV | VTA | VTT | VTL | VTV | ... |
| 26 | ... | LVL | LVV | VAA | VAT | VAL | VAV | VTA | VTT | VTL | VTV | VLA | ... |
| 27 | ... | LVV | VAA | VAT | VAL | VAV | VTA | VTT | VTL | VTV | VLA | VLT | ... |
| 30 | ... | VAA | VAT | VAL | VAV | VTA | VTT | VTL | VTV | VLA | VLT | VLL | ... |
| 31 | ... | VAT | VAL | VAV | VTA | VTT | VTL | VTV | VLA | VLT | VLL | VLV | ... |
| 32 | ... | VAL | VAV | VTA | VTT | VTL | VTV | VLA | VLT | VLL | VLV | VVA | ... |
| 33 | ... | VAV | VTA | VTT | VTL | VTV | VLA | VLT | VLL | VLV | VVA | VVT | ... |
| 34 | ... | VTA | VTT | VTL | VTV | VLA | VLT | VLL | VLV | VVA | VVT | VVL | ... |
| 35 | ... | VTT | VTL | VTV | VLA | VLT | VLL | VLV | VVA | VVT | VVL | VVV | ... |
| 36 | ... | VTL | VTV | VLA | VLT | VLL | VLV | VVA | VVT | VVL | VVV | AAA | ... |
| 37 | ... | VTV | VLA | VLT | VLL | VLV | VVA | VVT | VVL | VVV | AAA | AAT | ... |
| 40 | ... | VLA | VLT | VLL | VLV | VVA | VVT | VVL | VVV | AAA | AAT | AAL | ... |
| 41 | ... | VLT | VLL | VLV | VVA | VVT | VVL | VVV | AAA | AAT | AAL | AAV | ... |
| 42 | ... | VLL | VLV | VVA | VVT | VVL | VVV | AAA | AAT | AAL | AAV | ATA | ... |
| 43 | ... | VLV | VVA | VVT | VVL | VVV | AAA | AAT | AAL | AAV | ATA | ATT | ... |
| 44 | ... | VVA | VVT | VVL | VVV | AAA | AAT | AAL | AAV | ATA | ATT | ATL | ... |
| 45 | ... | VVT | VVL | VVV | AAA | AAT | AAL | AAV | ATA | ATT | ATL | ATV | ... |
| 46 | ... | VVL | VVV | AAA | AAT | AAL | AAV | ATA | ATT | ATL | ATV | ALA | ... |
| 47 | ... | VVV | AAA | AAT | AAL | AAV | ATA | ATT | ATL | ATV | ALA | ALT | ... |
| 50 | ... | AAA | AAT | AAL | AAV | ATA | ATT | ATL | ATV | ALA | ALT | ALL | ... |
| 51 | ... | AAT | AAL | AAV | ATA | ATT | ATL | ATV | ALA | ALT | ALL | ALV | ... |
| 52 | ... | AAL | AAV | ATA | ATT | ATL | ATV | ALA | ALT | ALL | ALV | AVA | ... |
| 53 | ... | AAV | ATA | ATT | ATL | ATV | ALA | ALT | ALL | ALV | AVA | AVT | ... |
| 54 | ... | ATA | ATT | ATL | ATV | ALA | ALT | ALL | ALV | AVA | AVT | AVL | ... |
| 55 | ... | ATT | ATL | ATV | ALA | ALT | ALL | ALV | AVA | AVT | AVL | AVV | ... |
| 56 | ... | ATL | ATV | ALA | ALT | ALL | ALV | AVA | AVT | AVL | AVV | TAA | ... |
| 57 | ... | ATV | ALA | ALT | ALL | ALV | AVA | AVT | AVL | AVV | TAA | TAT | ... |
| 60 | ... | ALA | ALT | ALL | ALV | AVA | AVT | AVL | AVV | TAA | TAT | TAL | ... |
| 61 | ... | ALT | ALL | ALV | AVA | AVT | AVL | AVV | TAA | TAT | TAL | TAV | ... |
| 62 | ... | ALL | ALV | AVA | AVT | AVL | AVV | TAA | TAT | TAL | TAV | TTA | ... |
| 63 | ... | ALV | AVA | AVT | AVL | AVV | TAA | TAT | TAL | TAV | TTA | TTT | ... |
| 64 | ... | AVA | AVT | AVL | AVV | TAA | TAT | TAL | TAV | TTA | TTT | TTL | ... |
| 65 | ... | AVT | AVL | AVV | TAA | TAT | TAL | TAV | TTA | TTT | TTL | TTV | ... |
| 66 | ... | AVL | AVV | TAA | TAT | TAL | TAV | TTA | TTT | TTL | TTV | TLA | ... |
| 67 | ... | AVV | TAA | TAT | TAL | TAV | TTA | TTT | TTL | TTV | TLA | TLT | ... |
| 70 | ... | TAA | TAT | TAL | TAV | TTA | TTT | TTL | TTV | TLA | TLT | TLL | ... |
| 71 | ... | TAT | TAL | TAV | TTA | TTT | TTL | TTV | TLA | TLT | TLL | TLV | ... |
| 72 | ... | TAL | TAV | TTA | TTT | TTL | TTV | TLA | TLT | TLL | TLV | TVA | ... |
| 73 | ... | TAV | TTA | TTT | TTL | TTV | TLA | TLT | TLL | TLV | TVA | TVT | ... |
| 74 | ... | TTA | TTT | TTL | TTV | TLA | TLT | TLL | TLV | TVA | TVT | TVL | ... |
| 75 | ... | TTT | TTL | TTV | TLA | TLT | TLL | TLV | TVA | TVT | TVL | TVV | ... |
| 76 | ... | TTL | TTV | TLA | TLT | TLL | TLV | TVA | TVT | TVL | TVV | LAA | ... |
| 77 | ... | TTV | TLA | TLT | TLL | TLV | TVA | TVT | TVL | TVV | LAA | LAT | ... |

FIG. 11N (cont'd)

| Symbols | | Previous symbols-to-amino-acids mapping | | | | | | | | | | |
|---|---|---|---|---|---|---|---|---|---|---|---|---|
| | ... | LAL | LAV | LTA | LTT | LTL | LTV | LLA | LLT | LLL | LLV | LVA | ... |
| 00 | ... | LAV | LTA | LTT | LTL | LTV | LLA | LLT | LLL | LLV | LVA | LVT | ... |
| 01 | ... | LTA | LTT | LTL | LTV | LLA | LLT | LLL | LLV | LVA | LVT | LVL | ... |
| 02 | ... | LTT | LTL | LTV | LLA | LLT | LLL | LLV | LVA | LVT | LVL | LVV | ... |
| 03 | ... | LTL | LTV | LLA | LLT | LLL | LLV | LVA | LVT | LVL | LVV | VAA | ... |
| 04 | ... | LTV | LLA | LLT | LLL | LLV | LVA | LVT | LVL | LVV | VAA | VAT | ... |
| 05 | ... | LLA | LLT | LLL | LLV | LVA | LVT | LVL | LVV | VAA | VAT | VAL | ... |
| 06 | ... | LLT | LLL | LLV | LVA | LVT | LVL | LVV | VAA | VAT | VAL | VAV | ... |
| 07 | ... | LLL | LLV | LVA | LVT | LVL | LVV | VAA | VAT | VAL | VAV | VTA | ... |
| 10 | ... | LLV | LVA | LVT | LVL | LVV | VAA | VAT | VAL | VAV | VTA | VTT | ... |
| 11 | ... | LVA | LVT | LVL | LVV | VAA | VAT | VAL | VAV | VTA | VTT | VTL | ... |
| 12 | ... | LVT | LVL | LVV | VAA | VAT | VAL | VAV | VTA | VTT | VTL | VTV | ... |
| 13 | ... | LVL | LVV | VAA | VAT | VAL | VAV | VTA | VTT | VTL | VTV | VLA | ... |
| 14 | ... | LVV | VAA | VAT | VAL | VAV | VTA | VTT | VTL | VTV | VLA | VLT | ... |
| 15 | ... | VAA | VAT | VAL | VAV | VTA | VTT | VTL | VTV | VLA | VLT | VLL | ... |
| 16 | ... | VAT | VAL | VAV | VTA | VTT | VTL | VTV | VLA | VLT | VLL | VLV | ... |
| 17 | ... | VAL | VAV | VTA | VTT | VTL | VTV | VLA | VLT | VLL | VLV | VVA | ... |
| 20 | ... | VAV | VTA | VTT | VTL | VTV | VLA | VLT | VLL | VLV | VVA | VVT | ... |
| 21 | ... | VTA | VTT | VTL | VTV | VLA | VLT | VLL | VLV | VVA | VVT | VVL | ... |
| 22 | ... | VTT | VTL | VTV | VLA | VLT | VLL | VLV | VVA | VVT | VVL | VVV | ... |
| 23 | ... | VTL | VTV | VLA | VLT | VLL | VLV | VVA | VVT | VVL | VVV | AAA | ... |
| 24 | ... | VTV | VLA | VLT | VLL | VLV | VVA | VVT | VVL | VVV | AAA | AAT | ... |
| 25 | ... | VLA | VLT | VLL | VLV | VVA | VVT | VVL | VVV | AAA | AAT | AAL | ... |
| 26 | ... | VLT | VLL | VLV | VVA | VVT | VVL | VVV | AAA | AAT | AAL | AAV | ... |
| 27 | ... | VLL | VLV | VVA | VVT | VVL | VVV | AAA | AAT | AAL | AAV | ATA | ... |
| 30 | ... | VLV | VVA | VVT | VVL | VVV | AAA | AAT | AAL | AAV | ATA | ATT | ... |
| 31 | ... | VVA | VVT | VVL | VVV | AAA | AAT | AAL | AAV | ATA | ATT | ATL | ... |
| 32 | ... | VVT | VVL | VVV | AAA | AAT | AAL | AAV | ATA | ATT | ATL | ATV | ... |
| 33 | ... | VVL | VVV | AAA | AAT | AAL | AAV | ATA | ATT | ATL | ATV | ALA | ... |
| 34 | ... | VVV | AAA | AAT | AAL | AAV | ATA | ATT | ATL | ATV | ALA | ALT | ... |
| 35 | ... | AAA | AAT | AAL | AAV | ATA | ATT | ATL | ATV | ALA | ALT | ALL | ... |
| 36 | ... | AAT | AAL | AAV | ATA | ATT | ATL | ATV | ALA | ALT | ALL | ALV | ... |
| 37 | ... | AAL | AAV | ATA | ATT | ATL | ATV | ALA | ALT | ALL | ALV | AVA | ... |
| 40 | ... | AAV | ATA | ATT | ATL | ATV | ALA | ALT | ALL | ALV | AVA | AVT | ... |
| 41 | ... | ATA | ATT | ATL | ATV | ALA | ALT | ALL | ALV | AVA | AVT | AVL | ... |
| 42 | ... | ATT | ATL | ATV | ALA | ALT | ALL | ALV | AVA | AVT | AVL | AVV | ... |
| 43 | ... | ATL | ATV | ALA | ALT | ALL | ALV | AVA | AVT | AVL | AVV | TAA | ... |
| 44 | ... | ATV | ALA | ALT | ALL | ALV | AVA | AVT | AVL | AVV | TAA | TAT | ... |
| 45 | ... | ALA | ALT | ALL | ALV | AVA | AVT | AVL | AVV | TAA | TAT | TAL | ... |
| 46 | ... | ALT | ALL | ALV | AVA | AVT | AVL | AVV | TAA | TAT | TAL | TAV | ... |
| 47 | ... | ALL | ALV | AVA | AVT | AVL | AVV | TAA | TAT | TAL | TAV | TTA | ... |
| 50 | ... | ALV | AVA | AVT | AVL | AVV | TAA | TAT | TAL | TAV | TTA | TTT | ... |
| 51 | ... | AVA | AVT | AVL | AVV | TAA | TAT | TAL | TAV | TTA | TTT | TTL | ... |
| 52 | ... | AVT | AVL | AVV | TAA | TAT | TAL | TAV | TTA | TTT | TTL | TTV | ... |
| 53 | ... | AVL | AVV | TAA | TAT | TAL | TAV | TTA | TTT | TTL | TTV | TLA | ... |
| 54 | ... | AVV | TAA | TAT | TAL | TAV | TTA | TTT | TTL | TTV | TLA | TLT | ... |
| 55 | ... | TAA | TAT | TAL | TAV | TTA | TTT | TTL | TTV | TLA | TLT | TLL | ... |
| 56 | ... | TAT | TAL | TAV | TTA | TTT | TTL | TTV | TLA | TLT | TLL | TLV | ... |
| 57 | ... | TAL | TAV | TTA | TTT | TTL | TTV | TLA | TLT | TLL | TLV | TVA | ... |
| 60 | ... | TAV | TTA | TTT | TTL | TTV | TLA | TLT | TLL | TLV | TVA | TVT | ... |
| 61 | ... | TTA | TTT | TTL | TTV | TLA | TLT | TLL | TLV | TVA | TVT | TVL | ... |
| 62 | ... | TTT | TTL | TTV | TLA | TLT | TLL | TLV | TVA | TVT | TVL | TVV | ... |
| 63 | ... | TTL | TTV | TLA | TLT | TLL | TLV | TVA | TVT | TVL | TVV | LAA | ... |
| 64 | ... | TTV | TLA | TLT | TLL | TLV | TVA | TVT | TVL | TVV | LAA | LAT | ... |
| 65 | ... | TLA | TLT | TLL | TLV | TVA | TVT | TVL | TVV | LAA | LAT | LAL | ... |
| 66 | ... | TLT | TLL | TLV | TVA | TVT | TVL | TVV | LAA | LAT | LAL | LAV | ... |
| 67 | ... | TLL | TLV | TVA | TVT | TVL | TVV | LAA | LAT | LAL | LAV | LTA | ... |
| 70 | ... | TLV | TVA | TVT | TVL | TVV | LAA | LAT | LAL | LAV | LTA | LTT | ... |
| 71 | ... | TVA | TVT | TVL | TVV | LAA | LAT | LAL | LAV | LTA | LTT | LTL | ... |
| 72 | ... | TVT | TVL | TVV | LAA | LAT | LAL | LAV | LTA | LTT | LTL | LTV | ... |
| 73 | ... | TVL | TVV | LAA | LAT | LAL | LAV | LTA | LTT | LTL | LTV | LLA | ... |
| 74 | ... | TVV | LAA | LAT | LAL | LAV | LTA | LTT | LTL | LTV | LLA | LLT | ... |
| 75 | ... | LAA | LAT | LAL | LAV | LTA | LTT | LTL | LTV | LLA | LLT | LLL | ... |
| 76 | ... | LAT | LAL | LAV | LTA | LTT | LTL | LTV | LLA | LLT | LLL | LLV | ... |
| 77 | ... | LAL | LAV | LTA | LTT | LTL | LTV | LLA | LLT | LLL | LLV | LVA | ... |

FIG. 11N (cont'd)

| Symbols | Previous symbols-to-amino-acids mapping | | | | | | | | | | | |
|---|---|---|---|---|---|---|---|---|---|---|---|---|
| | ... | LVT | LVL | LVV | VAA | VAT | VAL | VAV | VTA | VTT | VTL | VTV | ... |
| 00 | ... | LVL | LVV | VAA | VAT | VAL | VAV | VTA | VTT | VTL | VTV | VLA | ... |
| 01 | ... | LVV | VAA | VAT | VAL | VAV | VTA | VTT | VTL | VTV | VLA | VLT | ... |
| 02 | ... | VAA | VAT | VAL | VAV | VTA | VTT | VTL | VTV | VLA | VLT | VLL | ... |
| 03 | ... | VAT | VAL | VAV | VTA | VTT | VTL | VTV | VLA | VLT | VLL | VLV | ... |
| 04 | ... | VAL | VAV | VTA | VTT | VTL | VTV | VLA | VLT | VLL | VLV | VVA | ... |
| 05 | ... | VAV | VTA | VTT | VTL | VTV | VLA | VLT | VLL | VLV | VVA | VVT | ... |
| 06 | ... | VTA | VTT | VTL | VTV | VLA | VLT | VLL | VLV | VVA | VVT | VVL | ... |
| 07 | ... | VTT | VTL | VTV | VLA | VLT | VLL | VLV | VVA | VVT | VVL | VVV | ... |
| 10 | ... | VTL | VTV | VLA | VLT | VLL | VLV | VVA | VVT | VVL | VVV | AAA | ... |
| 11 | ... | VTV | VLA | VLT | VLL | VLV | VVA | VVT | VVL | VVV | AAA | AAT | ... |
| 12 | ... | VLA | VLT | VLL | VLV | VVA | VVT | VVL | VVV | AAA | AAT | AAL | ... |
| 13 | ... | VLT | VLL | VLV | VVA | VVT | VVL | VVV | AAA | AAT | AAL | AAV | ... |
| 14 | ... | VLL | VLV | VVA | VVT | VVL | VVV | AAA | AAT | AAL | AAV | ATA | ... |
| 15 | ... | VLV | VVA | VVT | VVL | VVV | AAA | AAT | AAL | AAV | ATA | ATT | ... |
| 16 | ... | VVA | VVT | VVL | VVV | AAA | AAT | AAL | AAV | ATA | ATT | ATL | ... |
| 17 | ... | VVT | VVL | VVV | AAA | AAT | AAL | AAV | ATA | ATT | ATL | ATV | ... |
| 20 | ... | VVL | VVV | AAA | AAT | AAL | AAV | ATA | ATT | ATL | ATV | ALA | ... |
| 21 | ... | VVV | AAA | AAT | AAL | ATA | ATT | ATL | ATV | ALA | ALA | ALT | ... |
| 22 | ... | AAA | AAT | AAL | AAV | ATA | ATT | ATL | ATV | ALA | ALT | ALL | ... |
| 23 | ... | AAT | AAL | AAV | ATA | ATT | ATL | ATV | ALA | ALT | ALL | ALV | ... |
| 24 | ... | AAL | AAV | ATA | ATT | ATL | ATV | ALA | ALT | ALL | ALV | AVA | ... |
| 25 | ... | AAV | ATA | ATT | ATL | ATV | ALA | ALT | ALL | ALV | AVA | AVT | ... |
| 26 | ... | ATA | ATT | ATL | ATV | ALA | ALT | ALL | ALV | AVA | AVT | AVL | ... |
| 27 | ... | ATT | ATL | ATV | ALA | ALT | ALL | ALV | AVA | AVT | AVL | AVV | ... |
| 30 | ... | ATL | ATV | ALA | ALT | ALL | ALV | AVA | AVT | AVL | AVV | TAA | ... |
| 31 | ... | ATV | ALA | ALT | ALL | ALV | AVA | AVT | AVL | AVV | TAA | TAT | ... |
| 32 | ... | ALA | ALT | ALL | ALV | AVA | AVT | AVL | AVV | TAA | TAT | TAL | ... |
| 33 | ... | ALT | ALL | ALV | AVA | AVT | AVL | AVV | TAA | TAT | TAL | TAV | ... |
| 34 | ... | ALL | ALV | AVA | AVT | AVL | AVV | TAA | TAT | TAL | TAV | TTA | ... |
| 35 | ... | ALV | AVA | AVT | AVL | AVV | TAA | TAT | TAL | TAV | TTA | TTT | ... |
| 36 | ... | AVA | AVT | AVL | AVV | TAA | TAT | TAL | TAV | TTA | TTT | TTL | ... |
| 37 | ... | AVT | AVL | AVV | TAA | TAT | TAL | TAV | TTA | TTT | TTL | TTV | ... |
| 40 | ... | AVL | AVV | TAA | TAT | TAL | TAV | TTA | TTT | TTL | TTV | TLA | ... |
| 41 | ... | AVV | TAA | TAT | TAL | TAV | TTA | TTT | TTL | TTV | TLA | TLT | ... |
| 42 | ... | TAA | TAT | TAL | TAV | TTA | TTT | TTL | TTV | TLA | TLT | TLL | ... |
| 43 | ... | TAT | TAL | TAV | TTA | TTT | TTL | TTV | TLA | TLT | TLL | TLV | ... |
| 44 | ... | TAL | TAV | TTA | TTT | TTL | TTV | TLA | TLT | TLL | TLV | TVA | ... |
| 45 | ... | TAV | TTA | TTT | TTL | TTV | TLA | TLT | TLL | TLV | TVA | TVT | ... |
| 46 | ... | TTA | TTT | TTL | TTV | TLA | TLT | TLL | TLV | TVA | TVT | TVL | ... |
| 47 | ... | TTT | TTL | TTV | TLA | TLT | TLL | TLV | TVA | TVT | TVL | TVV | ... |
| 50 | ... | TTL | TTV | TLA | TLT | TLL | TLV | TVA | TVT | TVL | TVV | LAA | ... |
| 51 | ... | TTV | TLA | TLT | TLL | TLV | TVA | TVT | TVL | TVV | LAA | LAT | ... |
| 52 | ... | TLA | TLT | TLL | TLV | TVA | TVT | TVL | TVV | LAA | LAT | LAL | ... |
| 53 | ... | TLT | TLL | TLV | TVA | TVT | TVL | TVV | LAA | LAT | LAL | LAV | ... |
| 54 | ... | TLL | TLV | TVA | TVT | TVL | TVV | LAA | LAT | LAL | LAV | LTA | ... |
| 55 | ... | TLV | TVA | TVT | TVL | TVV | LAA | LAT | LAL | LAV | LTA | LTT | ... |
| 56 | ... | TVA | TVT | TVL | TVV | LAA | LAT | LAL | LAV | LTA | LTT | LTL | ... |
| 57 | ... | TVT | TVL | TVV | LAA | LAT | LAL | LAV | LTA | LTT | LTL | LTV | ... |
| 60 | ... | TVL | TVV | LAA | LAT | LAL | LAV | LTA | LTT | LTL | LTV | LLA | ... |
| 61 | ... | TVV | LAA | LAT | LAL | LAV | LTA | LTT | LTL | LTV | LLA | LLT | ... |
| 62 | ... | LAA | LAT | LAL | LAV | LTA | LTT | LTL | LTV | LLA | LLT | LLL | ... |
| 63 | ... | LAT | LAL | LAV | LTA | LTT | LTL | LTV | LLA | LLT | LLL | LLV | ... |
| 64 | ... | LAL | LAV | LTA | LTT | LTL | LTV | LLA | LLT | LLL | LLV | LVA | ... |
| 65 | ... | LAV | LTA | LTT | LTL | LTV | LLA | LLT | LLL | LLV | LVA | LVT | ... |
| 66 | ... | LTA | LTT | LTL | LTV | LLA | LLT | LLL | LLV | LVA | LVT | LVL | ... |
| 67 | ... | LTT | LTL | LTV | LLA | LLT | LLL | LLV | LVA | LVT | LVL | LVV | ... |
| 70 | ... | LTL | LTV | LLA | LLT | LLL | LLV | LVA | LVT | LVL | LVV | VAA | ... |
| 71 | ... | LTV | LLA | LLT | LLL | LLV | LVA | LVT | LVL | LVV | VAA | VAT | ... |
| 72 | ... | LLA | LLT | LLL | LLV | LVA | LVT | LVL | LVV | VAA | VAT | VAL | ... |
| 73 | ... | LLT | LLL | LLV | LVA | LVT | LVL | LVV | VAA | VAT | VAL | VAV | ... |
| 74 | ... | LLL | LLV | LVA | LVT | LVL | LVV | VAA | VAT | VAL | VAV | VTA | ... |
| 75 | ... | LLV | LVA | LVT | LVL | LVV | VAA | VAT | VAL | VAV | VTA | VTT | ... |
| 76 | ... | LVA | LVT | LVL | LVV | VAA | VAT | VAL | VAV | VTA | VTT | VTL | ... |
| 77 | ... | LVT | LVL | LVV | VAA | VAT | VAL | VAV | VTA | VTT | VTL | VTV | ... |

FIG. 11N (cont'd)

| Symbols | | Previous symbols-to-amino-acids mapping | | | | | | | |
|---|---|---|---|---|---|---|---|---|---|
| | | VLA | VLT | VLL | VLV | VVA | VVT | VVL | VVV |
| 00 | ... | VLT | VLL | VLV | VVA | VVT | VVL | VVV | AAA |
| 01 | ... | VLL | VLV | VVA | VVT | VVL | VVV | AAA | AAT |
| 02 | ... | VLV | VVA | VVT | VVL | VVV | AAA | AAT | AAL |
| 03 | ... | VVA | VVT | VVL | VVV | AAA | AAT | AAL | AAV |
| 04 | ... | VVT | VVL | VVV | AAA | AAT | AAL | AAV | ATA |
| 05 | ... | VVL | VVV | AAA | AAT | AAL | AAV | ATA | ATT |
| 06 | ... | VVV | AAA | AAT | AAL | AAV | ATA | ATT | ATL |
| 07 | ... | AAA | AAT | AAL | AAV | ATA | ATT | ATL | ATV |
| 10 | ... | AAT | AAL | AAV | ATA | ATT | ATL | ATV | ALA |
| 11 | ... | AAL | AAV | ATA | ATT | ATL | ATV | ALA | ALT |
| 12 | ... | AAV | ATA | ATT | ATL | ATV | ALA | ALT | ALL |
| 13 | ... | ATA | ATT | ATL | ATV | ALA | ALT | ALL | ALV |
| 14 | ... | ATT | ATL | ATV | ALA | ALT | ALL | ALV | AVA |
| 15 | ... | ATL | ATV | ALA | ALT | ALL | ALV | AVA | AVT |
| 16 | ... | ATV | ALA | ALT | ALL | ALV | AVA | AVT | AVL |
| 17 | ... | ALA | ALT | ALL | ALV | AVA | AVT | AVL | AVV |
| 20 | ... | ALT | ALL | ALV | AVA | AVT | AVL | AVV | TAA |
| 21 | ... | ALL | ALV | AVA | AVT | AVL | AVV | TAA | TAT |
| 22 | ... | ALV | AVA | AVT | AVL | AVV | TAA | TAT | TAL |
| 23 | ... | AVA | AVT | AVL | AVV | TAA | TAT | TAL | TAV |
| 24 | ... | AVT | AVL | AVV | TAA | TAT | TAL | TAV | TTA |
| 25 | ... | AVL | AVV | TAA | TAT | TAL | TAV | TTA | TTT |
| 26 | ... | AVV | TAA | TAT | TAL | TAV | TTA | TTT | TTL |
| 27 | ... | TAA | TAT | TAL | TAV | TTA | TTT | TTL | TTV |
| 30 | ... | TAT | TAL | TAV | TTA | TTT | TTL | TTV | TLA |
| 31 | ... | TAL | TAV | TTA | TTT | TTL | TTV | TLA | TLT |
| 32 | ... | TAV | TTA | TTT | TTL | TTV | TLA | TLT | TLL |
| 33 | ... | TTA | TTT | TTL | TTV | TLA | TLT | TLL | TLV |
| 34 | ... | TTT | TTL | TTV | TLA | TLT | TLL | TLV | TVA |
| 35 | ... | TTL | TTV | TLA | TLT | TLL | TLV | TVA | TVT |
| 36 | ... | TTV | TLA | TLT | TLL | TLV | TVA | TVT | TVL |
| 37 | ... | TLA | TLT | TLL | TLV | TVA | TVT | TVL | TVV |
| 40 | ... | TLT | TLL | TLV | TVA | TVT | TVL | TVV | LAA |
| 41 | ... | TLL | TLV | TVA | TVT | TVL | TVV | LAA | LAT |
| 42 | ... | TLV | TVA | TVT | TVL | TVV | LAA | LAT | LAL |
| 43 | ... | TVA | TVT | TVL | TVV | LAA | LAT | LAL | LAV |
| 44 | ... | TVT | TVL | TVV | LAA | LAT | LAL | LAV | LTA |
| 45 | ... | TVL | TVV | LAA | LAT | LAL | LAV | LTA | LTT |
| 46 | ... | TVV | LAA | LAT | LAL | LAV | LTA | LTT | LTL |
| 47 | ... | LAA | LAT | LAL | LAV | LTA | LTT | LTL | LTV |
| 50 | ... | LAT | LAL | LAV | LTA | LTT | LTL | LTV | LLA |
| 51 | ... | LAL | LAV | LTA | LTT | LTL | LTV | LLA | LLT |
| 52 | ... | LAV | LTA | LTT | LTL | LTV | LLA | LLT | LLL |
| 53 | ... | LTA | LTT | LTL | LTV | LLA | LLT | LLL | LLV |
| 54 | ... | LTT | LTL | LTV | LLA | LLT | LLL | LLV | LVA |
| 55 | ... | LTL | LTV | LLA | LLT | LLL | LLV | LVA | LVT |
| 56 | ... | LTV | LLA | LLT | LLL | LLV | LVA | LVT | LVL |
| 57 | ... | LLA | LLT | LLL | LLV | LVA | LVT | LVL | LVV |
| 60 | ... | LLT | LLL | LLV | LVA | LVT | LVL | LVV | VAA |
| 61 | ... | LLL | LLV | LVA | LVT | LVL | LVV | VAA | VAT |
| 62 | ... | LLV | LVA | LVT | LVL | LVV | VAA | VAT | VAL |
| 63 | ... | LVA | LVT | LVL | LVV | VAA | VAT | VAL | VAV |
| 64 | ... | LVT | LVL | LVV | VAA | VAT | VAL | VAV | VTA |
| 65 | ... | LVL | LVV | VAA | VAT | VAL | VAV | VTA | VTT |
| 66 | ... | LVV | VAA | VAT | VAL | VAV | VTA | VTT | VTL |
| 67 | ... | VAA | VAT | VAL | VAV | VTA | VTT | VTL | VTV |
| 70 | ... | VAT | VAL | VAV | VTA | VTT | VTL | VTV | VLA |
| 71 | ... | VAL | VAV | VTA | VTT | VTL | VTV | VLA | VLT |
| 72 | ... | VAV | VTA | VTT | VTL | VTV | VLA | VLT | VLL |
| 73 | ... | VTA | VTT | VTL | VTV | VLA | VLT | VLL | VLV |
| 74 | ... | VTT | VTL | VTV | VLA | VLT | VLL | VLV | VVA |
| 75 | ... | VTL | VTV | VLA | VLT | VLL | VLV | VVA | VVT |
| 76 | ... | VTV | VLA | VLT | VLL | VLV | VVA | VVT | VVL |
| 77 | ... | VLA | VLT | VLL | VLV | VVA | VVT | VVL | VVV |

FIG. 11N (cont'd)

| Bit | Amino acid mapping | |
|---|---|---|
| 0 | A or T or L or V | A, T, L and V can be selected with equal or unequal probabilities |
| 1 | E or H or Y or F | E, H, Y and F can be selected with equal or unequal probabilities |

FIG. 11O

| Symbol | Amino acid mapping | |
|---|---|---|
| 0 | A or T | A and T can be selected with equal or unequal probabilities |
| 1 | L or V | L and V can be selected with equal or unequal probabilities |
| 2 | E or H | E and H can be selected with equal or unequal probabilities |
| 3 | Y or F | Y and F can be selected with equal or unequal probabilities |

FIG. 11P

| Symbol | Amino acids mapping | |
|---|---|---|
| 0 | AAA or AAT | AAA and AAT can be selected with equal or unequal probabilities |
| 1 | ATA or ATT | ATA and ATT can be selected with equal or unequal probabilities |
| 2 | TAA or TAT | TAA and TAT can be selected with equal or unequal probabilities |
| 3 | TTA or TTT | TTA and TTT can be selected with equal or unequal probabilities |

FIG. 11Q

| Symbols | Amino acid mapping | |
|---|---|---|
| 00 | A or T | A and T can be selected with equal or unequal probabilities |
| 01 | L or V | L and V can be selected with equal or unequal probabilities |
| 02 | E or H | E and H can be selected with equal or unequal probabilities |
| 10 | Y or F | Y and F can be selected with equal or unequal probabilities |
| 11 | D or K | D and K can be selected with equal or unequal probabilities |
| 12 | R or P | R and P can be selected with equal or unequal probabilities |
| 20 | W or C | W and C can be selected with equal or unequal probabilities |
| 21 | G or S | G and S can be selected with equal or unequal probabilities |
| 22 | N or Q | N and Q can be selected with equal or unequal probabilities |

FIG. 11R

| Symbols | Amino acids mapping | |
|---|---|---|
| 00 | AA or AT or AL or AV | AA, AT, AL and AV can be selected with equal or unequal probabilities |
| 01 | TA or TT or TL or TV | TA, TT, TL and TV can be selected with equal or unequal probabilities |
| 02 | LA or LT or LL or LV | LA, LT, LL and LV can be selected with equal or unequal probabilities |
| 10 | VA or VT or VL or VV | VA, VT, VL and VV can be selected with equal or unequal probabilities |
| 11 | EA or ET or EL or EV | EA, ET, EL and EV can be selected with equal or unequal probabilities |
| 12 | HA or HT or HL or HV | HA, HT, HL and HV can be selected with equal or unequal probabilities |
| 20 | YA or YT or YL or YV | YA, YT, YL and YV can be selected with equal or unequal probabilities |
| 21 | FA or FT or FL or FV | FA, FT, FL and FV can be selected with equal or unequal probabilities |
| 22 | DA or DT or DL or DV | DA, DT, DL and DV can be selected with equal or unequal probabilities |

| Name | Sequence | MS1 TIC intensity | charge of the most intense ion | charges observed | solvent | Can be sequenced using HCD for fragmentation |
|---|---|---|---|---|---|---|
| 20 | FYEVTVFAEVLYFEYETR SEQ ID NO: 1 | 3.00E+07 | 2 | 2 | 1:3 water:AcN | OK |
| 20-C2R | FYEVTVFAEVLYFEYETRR SEQ ID NO: 2 | 5.65E+07 | 3 | 2,3 | 1:3:6 water:AcN:DMSO | FAIL |
| 20-C3R | FYEVTVFAEVLYFEYETRRR SEQ ID NO: 3 | 5.41E+07 | 3 | 2,3,4 | 1:1 water:AcN | FAIL |
| 20-C4R | FYEVTVFAEVLYFEYETRRRR SEQ ID NO: 4 | 2.30E+07 | 4 | 3,4,5 | water | FAIL |
| 63 | FYFLVALSEATSVAELAR SEQ ID NO: 5 | 2.73E+08 | 2 | 2 | 1:1 water:AcN | OK |
| 63-C2R | FYFLVALSEATSVAELARR SEQ ID NO: 6 | 5.55E+07 | 3 | 2,3 | 1:1 water:AcN | FAIL |
| 63-C3R | FYFLVALSEATSVAELARRR SEQ ID NO: 7 | 1.06E+08 | 3 | 2,3,4 | 1:1 water:AcN | FAIL |
| 63-C4R | FYFLVALSEATSVAELARRRR SEQ ID NO: 8 | 7.15E+08 | 4 | 3,4,5 | water | FAIL |

FIG. 16

SEQUENCE LISTING

```
<160> NUMBER OF SEQ ID NOS: 12

<210> SEQ ID NO 1
<211> LENGTH: 18
<212> TYPE: PRT
<213> ORGANISM: Artificial Sequence
<220> FEATURE:
<223> OTHER INFORMATION: Synthetic peptide. Prepared in the lab.

<400> SEQUENCE: 1

Phe Tyr Glu Val Thr Val Phe Ala Glu Val Leu Tyr Phe Glu Tyr Glu
1               5                   10                  15

Thr Arg

<210> SEQ ID NO 2
<211> LENGTH: 19
<212> TYPE: PRT
<213> ORGANISM: Artificial Sequence
<220> FEATURE:
<223> OTHER INFORMATION: Synthetic peptide. Prepared in the lab.

<400> SEQUENCE: 2

Phe Tyr Glu Val Thr Val Phe Ala Glu Val Leu Tyr Phe Glu Tyr Glu
1               5                   10                  15

Thr Arg Arg

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide. Prepared in the lab.

<400> SEQUENCE: 3

Phe Tyr Glu Val Thr Val Phe Ala Glu Val Leu Tyr Phe Glu Tyr Glu
1               5                   10                  15

Thr Arg Arg Arg
            20

<210> SEQ ID NO 4
<211> LENGTH: 21
<212> TYPE: PRT
<213> ORGANISM: Artificial Sequence
<220> FEATURE:
<223> OTHER INFORMATION: Synthetic peptide. Prepared in the lab.

<400> SEQUENCE: 4
```

```
Phe Tyr Glu Val Thr Val Phe Ala Glu Val Leu Tyr Phe Glu Tyr Glu
1               5                   10                  15

Thr Arg Arg Arg Arg
            20
```

<210> SEQ ID NO 5
<211> LENGTH: 18
<212> TYPE: PRT
<213> ORGANISM: Artificial Sequence
<220> FEATURE:
<223> OTHER INFORMATION: Synthetic peptide. Prepared in the lab.

<400> SEQUENCE: 5

```
Phe Tyr Phe Leu Val Ala Leu Ser Glu Ala Thr Ser Val Ala Glu Leu
1               5                   10                  15

Ala Arg
```

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide. Prepared in the lab.

<400> SEQUENCE: 6

```
Phe Tyr Phe Leu Val Ala Leu Ser Glu Ala Thr Ser Val Ala Glu Leu
1               5                   10                  15

Ala Arg Arg
```

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide. Prepared in the lab.

<400> SEQUENCE: 7

```
Phe Tyr Phe Leu Val Ala Leu Ser Glu Ala Thr Ser Val Ala Glu Leu
1               5                   10                  15

Ala Arg Arg Arg
            20
```

<210> SEQ ID NO 8
<211> LENGTH: 21
<212> TYPE: PRT
<213> ORGANISM: Artificial Sequence
<220> FEATURE:
<223> OTHER INFORMATION: Synthetic peptide. Prepared in the lab.

<400> SEQUENCE: 8

```
Phe Tyr Phe Leu Val Ala Leu Ser Glu Ala Thr Ser Val Ala Glu Leu
1               5                   10                  15

Ala Arg Arg Arg Arg
            20
```

<210> SEQ ID NO 9
<211> LENGTH: 18
<212> TYPE: PRT
<213> ORGANISM: Artificial Sequence
<220> FEATURE:
<223> OTHER INFORMATION: Synthetic peptide. Prepared in the lab.

<400> SEQUENCE: 9

```
Arg Tyr Glu Val Thr Val Phe Ala Glu Val Leu Tyr Phe Glu Tyr Glu
```

-continued

```
1               5                   10                  15
Thr Arg

<210> SEQ ID NO 10
<211> LENGTH: 24
<212> TYPE: PRT
<213> ORGANISM: Artificial Sequence
<220> FEATURE:
<223> OTHER INFORMATION: Synthetic peptide. Prepared in the lab.

<400> SEQUENCE: 10

Phe Tyr Phe Leu Val Ala Leu Ser Glu Ala Thr Ser Val Ala Val Thr
1               5                   10                  15

Leu Phe Glu Ala Glu Leu Ala Arg
            20

<210> SEQ ID NO 11
<211> LENGTH: 17
<212> TYPE: PRT
<213> ORGANISM: Artificial Sequence
<220> FEATURE:
<223> OTHER INFORMATION: Synthetic peptide. Prepared in the lab.
<220> FEATURE:
<221> NAME/KEY: MISC_FEATURE
<222> LOCATION: (17)..(17)
<223> OTHER INFORMATION: Xaa at position 17 is N-(3-aminopropyl) alanine

<400> SEQUENCE: 11

Phe Tyr Phe Leu Val Ala Leu Ser Glu Ala Thr Ser Val Ala Glu Leu
1               5                   10                  15

Xaa

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide. Prepared in the lab.

<400> SEQUENCE: 12

Phe Ser Thr Tyr Tyr Glu Thr Phe Ser Ser Leu Val Tyr Val Leu Ala
1               5                   10                  15

Thr Arg
```

DATA STORAGE USING PEPTIDES

CROSS-REFERENCE TO RELATED APPLICATIONS

This application is a continuation-in-part of and claims the benefit of priority of U.S. Non-Provisional application Ser. No. 16/224,957, filed on Dec. 19, 2018, which claims the benefit of priority of U.S. Provisional Application No. 62/657,026, filed on Apr. 13, 2018, the contents of each of which being hereby incorporated by reference in their entirety for all purposes.

REFERENCE TO SEQUENCE LISTING

The specification further incorporates by reference the Substitute Sequence Listing submitted herewith via EFS-Web on Dec. 14, 2020. The Substitute Sequence Listing text file, identified as Sequence_Listing_034577-000063.txt, is 4,033 bytes and was created on Dec. 14, 2020. The Substitute Sequence Listing, electronically filed herewith does not contain new matter.

TECHNICAL FIELD

The present disclosure relates to data storage and retrieval, and more particularly, to methods and systems for data storage and retrieval using peptides with improved physical-chemical properties.

BACKGROUND

With digital data being generated at an exponential rate, storage of digital data becomes particularly important to the growth of information technology. These digital data are represented by bits of 0 and 1 and stored in media, such as hard drives and magnetic tapes. Many of rarely accessed data have been archived on reels of magnetic tapes. The physical limitations in the thickness of tapes and the size of magnetic domains pose a limitation to the maximum data density, which is expected to reach a plateau soon. In order to store the huge amount of data generated, huge storage space in specially built data centres is needed. Furthermore, the magnetic tapes are rated to last for several decades only, and copying data from old tapes into new tapes from time to time is required, which is both time-consuming and expensive.

One of the emerging technologies to fulfil this need is storing digital data in DNA, where the set of monomers (nucleotides) with different side chains represents the different combinations of 0 and 1 in digital data. To retrieve the data, the DNA strands are sequenced, and the sequence information of the monomers is converted back to combinations of 0 and 1. However, DNA has only 4 natural nucleotides, and unnatural nucleotides may not be used for data storage since they cannot be recognized by the enzymes for DNA sequencing. In addition, DNA is prone to degradation which makes it challenging for long-term data storage.

Hence, what is needed is an improved method and system for storing and retrieving digital data that seeks to address one or more of the above-mentioned problems. Furthermore, other desirable features and characteristics will become apparent from the subsequent detailed description and the appended claims, taken in conjunction with the accompanying drawings and this background of the disclosure.

SUMMARY

According to a first aspect, there is provided a method of storing digital data into peptide sequences.

In certain embodiments, the method of storing digital data into peptide sequences may comprise: encoding the digital data into a digital code; translating the digital code into the peptide sequences; and synthesizing the translated peptide sequences.

In certain embodiments, the translating of the digital code into peptide sequences may comprise mapping a bit pattern or a symbol pattern into one or more amino acids such that the digital code is represented by a sequence of amino acids in the peptide sequences.

In certain embodiments, the method of storing digital data into peptide sequences may further comprise forming a mixture of peptides based on the translated peptide sequences.

In certain embodiments, the method of storing digital data into peptide sequences may further comprise adding one or more order-checking bits into the digital code, wherein the one or more order-checking bits may be related to the order of the bits or symbols in the digital code.

In certain embodiments, the method of storing digital data into peptide sequences may further comprise adding one or more error-correction codes into the digital code, wherein the one or more error-correction codes may comprise any one or combination of repetition code, convolutional code, turbo code, fountain code, low-density parity-check (LDPC) code, Reed-Solomon (RS) code, Hadamard code, and Hamming code.

In certain embodiments, the one or more error-correction codes may be generated based on the digital code, or both the digital code and order-checking bits added into the digital code.

In certain embodiments, the peptide sequences may comprise distinct functional groups, isotope labels or affinity labels.

In certain embodiments, the peptide sequences may comprise digital data bearing amino acids and non-digital data bearing amino acids.

According to a second aspect, there is provided a method of retrieving digital data from peptide sequences.

In certain embodiments, the method of retrieving digital data from peptide sequences may comprise: sequencing and determining an order of the peptide sequences; converting the peptide sequences with the determined order into a digital code; and decoding the digital data from the digital code.

In certain embodiments, the converting of the peptide sequences with the determined order into the digital code may comprise mapping one or more amino acids in the peptide sequences into a bit pattern or a symbol pattern such that the digital code is obtained from a sequence of amino acids in the peptide sequences with the determined order.

In certain embodiments, the method of retrieving digital data from peptide sequences may further comprise separating peptide sequences from a mixture of peptides.

In certain embodiments, the digital code may comprise one or more order-checking bits, wherein the one or more order-checking bits may be related to the order of the bits or symbols in the digital code.

In certain embodiments, the digital code may comprise one or more error-correction codes, wherein the one or more error-correction codes may comprise any one or combination of repetition code, convolutional code, turbo code, fountain code, LDPC code, RS code, Hadamard code, and Hamming code.

In certain embodiments, decoding the digital data from digital code may use algorithms comprising belief-propagation algorithm, message-passing algorithm, and sum-product algorithm, and bit-flipping algorithm.

In certain embodiments, the method of retrieving digital data from peptide sequences may further comprise: encoding the orders of one or more bits or symbols in the digital code; comparing the order-checking bits with the encoded orders of the one or more bits or symbols in the digital code; and indicating a detected error if the order-checking bits do not match the encoded orders of the one or more bits or symbols in the digital code.

According to a third aspect, there is provided a system for storing digital data into peptide sequences, the system comprising: a synthesizer configured to synthesize peptide sequences; at least one processor in communication with the synthesizer; and at least one memory including computer program code, the at least one memory and the computer program code configured to, with the at least one processor, cause the system at least to: encode the digital data into a digital code; translate the digital code into peptide sequences; and synthesize the translated peptide sequences using the synthesizer.

In certain embodiments, when the system is caused to translate the digital code into peptide sequences, the at least one memory and the computer program code may be configured to, with the at least one processor, cause the system at least to map a bit pattern or a symbol pattern of the digital code into one or more amino acids such that the digital code is represented by a sequence of amino acids in the peptide sequences.

In certain embodiments, the system may be further configured to form a mixture of peptides based on the translated peptide sequences.

In certain embodiments, the at least one memory and the computer program code may be configured to, with the at least one processor, cause the system further to add one or more order-checking bits into the digital code, wherein the one or more order-checking bits may be related to the order of the bits or symbols in the digital code.

In certain embodiments, the at least one memory and the computer program code may be configured to, with the at least one processor, cause the system further to add one or more error-correction codes into the digital code, wherein the one or more error-correction codes may comprise any one or combination of repetition code, convolutional code, turbo code, fountain code, LDPC code, RS code, Hadamard code, and Hamming code.

In certain embodiments, the one or more error-correction codes may be generated based on the digital code, or both the digital code and order-checking bits added into the digital code.

In certain embodiments, the peptide sequences may comprise distinct functional groups, isotope labels or affinity labels.

In certain embodiments, the peptide sequences may comprise digital data bearing amino acids and non-digital data bearing amino acids.

According to a fourth aspect, there is provided a system for retrieving digital data from peptide sequences, the system comprising: a sequencer configured to sequence and determine an order of the peptide sequences; at least one processor in communication with the sequencer; and at least one memory including computer program code, the at least one memory and the computer program code configured to, with the at least one processor, cause the system at least to: sequence and determine the order of the peptide sequences using the sequencer; convert the peptide sequences with the determined order into a digital code; and decode the digital data from the digital code.

In certain embodiments, when the system is caused to convert the peptide sequences with the determined order into a digital code, the at least one memory and the computer program code may be configured to, with the at least one processor, cause the system at least to map one or more amino acids in the peptide sequences into a bit pattern or a symbol pattern such that the digital code is obtained from a sequence of amino acids in the peptide sequences with the determined order.

In certain embodiments, the sequencer may be further configured to separate peptide sequences from a mixture of peptides.

In certain embodiments, the digital code may comprise one or more order-checking bits, wherein the one or more order-checking bits may be related to the order of the bits or symbols in the digital code.

In certain embodiments, the digital code may comprise one or more error-correction codes, wherein the one or more error-correction codes may comprise any one or combination of repetition code, convolutional code, turbo code, fountain code, LDPC code, RS code, Hadamard code, and Hamming code.

In certain embodiments, decoding the digital data from digital code may use algorithms comprising belief-propagation algorithm, message-passing algorithm, and sum-product algorithm, and bit-flipping algorithm.

In certain embodiments, the at least one memory and the computer program code may be configured to, with the at least one processor, cause the system further to: encode the orders of one or more bits or symbols in the digital code; compare the order-checking bits with the encoded orders of the one or more bits or symbols in the digital code; and indicate a detected error if the order-checking bits do not match the encoded orders of the one or more bits or symbols in the digital code.

According to a fifth aspect, there is provided a computational method for assigning peptide sequences, wherein the method comprises an algorithm that recognizes and scores one or more features.

In certain embodiments, the one or more of the features may comprise: length of consecutive amino acids retrieved; isotope labels; number of amino acids retrieved; match error; intensity; and number of occurrences for different ion types with different offsets.

According to a sixth aspect, there is provided a method of storing digital data into one or more peptide sequences, the method comprising: encoding the digital data into a digital code; translating the digital code into the one or more peptide sequences, wherein translating the digital code comprises mapping a bit pattern or a symbol pattern into one or more amino acids such that the digital code is represented by a sequence of amino acids in the one or more peptide sequences; and wherein each of the one or more peptide sequences independently comprises a N-terminal amino acid covalently bonded via an internal amino acid sequence to a C-terminal amino acid; and providing the one or more translated peptide sequences, with the proviso that if the one or more peptide sequences comprise two or more amino acids with identical molecular weights, then the two or more amino acids have the same mapped bit pattern or symbol pattern.

In certain embodiments, the N-terminal amino acid of each of the one or more translated peptide sequences is the same; and the C-terminal amino acid of each of the one or more translated peptide sequences is the same.

In certain embodiments, each of the one or more translated peptide sequences independently consists of 8-30 amino acids.

In certain embodiments, each of the one or more translated peptide sequences contains no more than one basic amino acid.

In certain embodiments, each of the one or more translated peptide sequences contains no more than one basic amino acid independently selected from the group consisting of lysine, arginine, histidine, 1,2-diaminoethane, and 1,3-diaminopropane (DAP).

In certain embodiments, the N-terminal of each of the one or more translated peptide sequences is selected from the group consisting of serine, threonine, histidine, lysine, aspartic acid, and glutamic acid.

In certain embodiments, the C-terminal of each of the one or more translated peptide sequences is selected from the group consisting of lysine, arginine, histidine, 1,2-diaminoethane, and DAP.

In certain embodiments, each of the internal amino acid sequences do not comprise histidine, lysine, arginine, or aspartic acid.

In certain embodiments, each of the one or more translated peptide sequences do not comprises cysteine, tryptophan, methionine, asparagine, or glutamine.

In certain embodiments, the step of providing the translated peptide sequences comprises synthesizing the translated peptide sequences.

In certain embodiments, the translating of the digital code into peptide sequences comprises: mapping a bit pattern or a symbol pattern into one or more amino acids such that the digital code is represented by a sequence of amino acids in the one or more peptide sequences.

In certain embodiments, the method further comprises adding one or more order-checking bits into the digital code, wherein the one or more order-checking bits are related to the order of the bits or symbols in the digital code.

In certain embodiments, the translating of the digital code into peptide sequences comprises: mapping a bit pattern or a symbol pattern into one or more amino acids such that the digital code is represented by a sequence of amino acids in the one or more peptide sequences; each of the one or more peptide sequences independently consists of 17-24 amino acids; each of the one or more peptide sequences contains one basic amino acid located at the C-terminal of each of the one or more peptide sequences selected from the group consisting of DAP and arginine; the N-terminal of each of the one or more peptide sequences is selected from the group consisting of serine, threonine, aspartic acid, and glutamic acid; each of the internal amino acid sequences do not comprise histidine, lysine, arginine, or aspartic acid; and each of the one or more peptide sequences do not comprises cysteine, tryptophan, methionine, asparagine, or glutamine.

According to a seventh aspect, there is provided a method of retrieving digital data from one or more peptide sequences, wherein the retrieving digital data from the one or more peptide sequences comprises: sequencing and determining an order of the one or more peptide sequences, wherein each of the one or more peptide sequences independently comprises a N-terminal amino acid covalently bonded via an internal amino acid sequence to a C-terminal amino acid sequencing and wherein the step of sequencing and determining an order of the one or more peptide sequences comprises a mass spectroscopy method; converting the one or more peptide sequences with the determined order into a digital code wherein the converting of the peptide sequences with the determined order into the digital code comprises mapping one or more amino acids in the peptide sequences into a bit pattern or a symbol pattern such that the digital code is obtained from a sequence of amino acids in the peptide sequences with the determined order; and decoding the digital data from the digital code, with the proviso that if the one or more peptide sequences comprise two or more amino acids with identical molecular weights, then the two or more amino acids have the same mapped bit pattern or symbol pattern.

In certain embodiments, the step of sequencing the one or more peptide sequences comprises a sequencing method selected from the group consisting of a graph theory model and a highest-intensity tag based model.

In certain embodiments, the mass spectroscopy method comprises matrix assisted laser desorption ionization mass spectrometry or liquid chromatograph-mass spectrometry/mass spectrometry.

In certain embodiments, the N-terminal amino acid of each of the one or more translated peptide sequences is the same; and the C-terminal amino acid of each of the one or more translated peptide sequences is the same.

In certain embodiments, each of the one or more translated peptide sequences independently consists of 8-30 amino acids.

In certain embodiments, each of the one or more translated peptide sequences contains no more than one basic amino acid.

In certain embodiments, each of the one or more translated peptide sequences contains no more than one basic amino acid independently selected from the group consisting of lysine, arginine, histidine, 1,2-diaminoethane, and DAP.

In certain embodiments, the N-terminal of each of the one or more translated peptide sequences is selected from the group consisting of serine, threonine, histidine, lysine, aspartic acid, and glutamic acid.

In certain embodiments, the C-terminal of each of the one or more translated peptide sequences is selected from the group consisting of lysine, arginine, histidine, 1,2-diaminoethane, and DAP.

In certain embodiments, each of the internal amino acid sequences do not comprise histidine, lysine, arginine, or aspartic acid.

In certain embodiments, each of the one or more translated peptide sequences do not comprises cysteine, tryptophan, methionine, asparagine, or glutamine.

In certain embodiments, the digital code comprises one or more order-checking bits, wherein the one or more order-checking bits are related to the order of the bits or symbols in the digital code.

In certain embodiments, the step of sequencing the one or more peptide sequences comprises a sequencing method selected from the group consisting of a graph theory model and a highest-intensity tag based model; the mass spectroscopy method comprises matrix assisted laser desorption ionization mass spectrometry or liquid chromatograph-mass spectrometry/mass spectrometry; each of the one or more peptide sequences independently consists of 17-24 amino acids; each of the one or more peptide sequences contains one basic amino acid located at the C-terminal of each of the one or more peptide sequences selected from the group consisting of DAP and arginine; the N-terminal of each of the one or more peptide sequences is selected from the group consisting of serine, threonine, aspartic acid, and glutamic acid; each of the internal amino acid sequences do not comprise histidine, lysine, arginine, or aspartic acid; and each of the one or more peptide sequences do not comprises cysteine, tryptophan, methionine, asparagine, or glutamine.

According to an eighth aspect, there is provided a system for storing digital data into one or more peptide sequences, the system comprising: a synthesizer configured to synthesize the one or more peptide sequences; at least one processor in communication with the synthesizer; and at least one memory including computer program code, the at least one memory and the computer program code configured to, with the at least one processor, cause the system at least to: encode the digital data into a digital code; translate the digital code into one or more peptide sequences, wherein each of the one or more translated peptide sequences independently comprises a N-terminal amino acid covalently bonded via an internal amino acid sequence to a C-terminal amino acid; and synthesize the one or more translated peptide sequences using the synthesizer, with the proviso that the one or more translated peptide sequences do not comprise both leucine and isoleucine.

According to a ninth aspect, there is provided a system for retrieving digital data from one or more peptide sequences, the system comprising: a mass spectrometer configured to sequence and determine an order of the one or more peptide sequences, wherein the mass spectrometer is selected from the group consisting of matrix assisted laser desorption ionization mass spectrometry and liquid chromatography-mass spectrometry/mass spectrometry; at least one processor in communication with the sequencer; and at least one memory including computer program code, the at least one memory and the computer program code configured to, with the at least one processor, cause the system at least to: sequence and determine the order of the peptide sequences using the mass spectrometer, wherein the step of sequencing and determining the order of the one or more peptide sequences comprises a sequencing method selected from the group consisting of a graph theory model and a highest-intensity tag based model; convert the one or more peptide sequences with the determined order into a digital code; and decode the digital data from the digital code.

Embodiments of the present disclosure provide an efficient data storage method and system using peptide sequences. The storage of digital data is performed by mapping a pattern of bits/symbols of the digital data in one or more amino acids of the peptide sequences. Firstly, peptides can offer a much higher data density than DNA. In addition to the 20 natural amino acids, unnatural amino acids can be also incorporated for data storage since the peptide sequencing can be performed using tandem mass spectrometry (MS/MS) with no enzyme recognition involved. The increased set of possible monomers, together with the lower masses of amino acids than those of nucleotides, could endow peptides a much higher data density than DNA. Secondly, peptides are typically less prone to degradation than DNA and can be still detectable even after millions of years when DNA would have already degraded. Furthermore, the peptide synthesis industry has been well developed, and various peptides can be easily obtained at a reasonable price. With the development of proteomics, the hardware and software for separation, detection and sequencing of peptides have been well established. Sequencing thousands of peptides in a mixture at a very small amount has become routine and can be completed within a short time of period.

BRIEF DESCRIPTION OF DRAWINGS

Embodiments of the disclosure will be better understood and readily apparent to one of ordinary skill in the art from the following written description, by way of example only, and in conjunction with the drawings, in which:

FIGS. 9A-B depict illustrations of retrieving digital data from peptide sequences in accordance with embodiments of the disclosure.

FIG. 10 depicts an illustration of using an error-correction method to ensure data integrity in accordance with embodiments of the disclosure.

FIGS. 11A-S depict illustrations of examples of the mapping between bit(s)/symbol(s) to amino acid(s) in accordance with embodiments of the disclosure.

FIG. 16 depicts Table 5, which shows a comparison of the MS1 spectral characteristics, solubility properties, and mass spectrometry (MS) sequencing success, for peptides with one to four R at the C-terminal.

11) with various HCD energy. Lower HCD energy than R-terminated peptides can be used to produce good spectra.

Figure 21A:
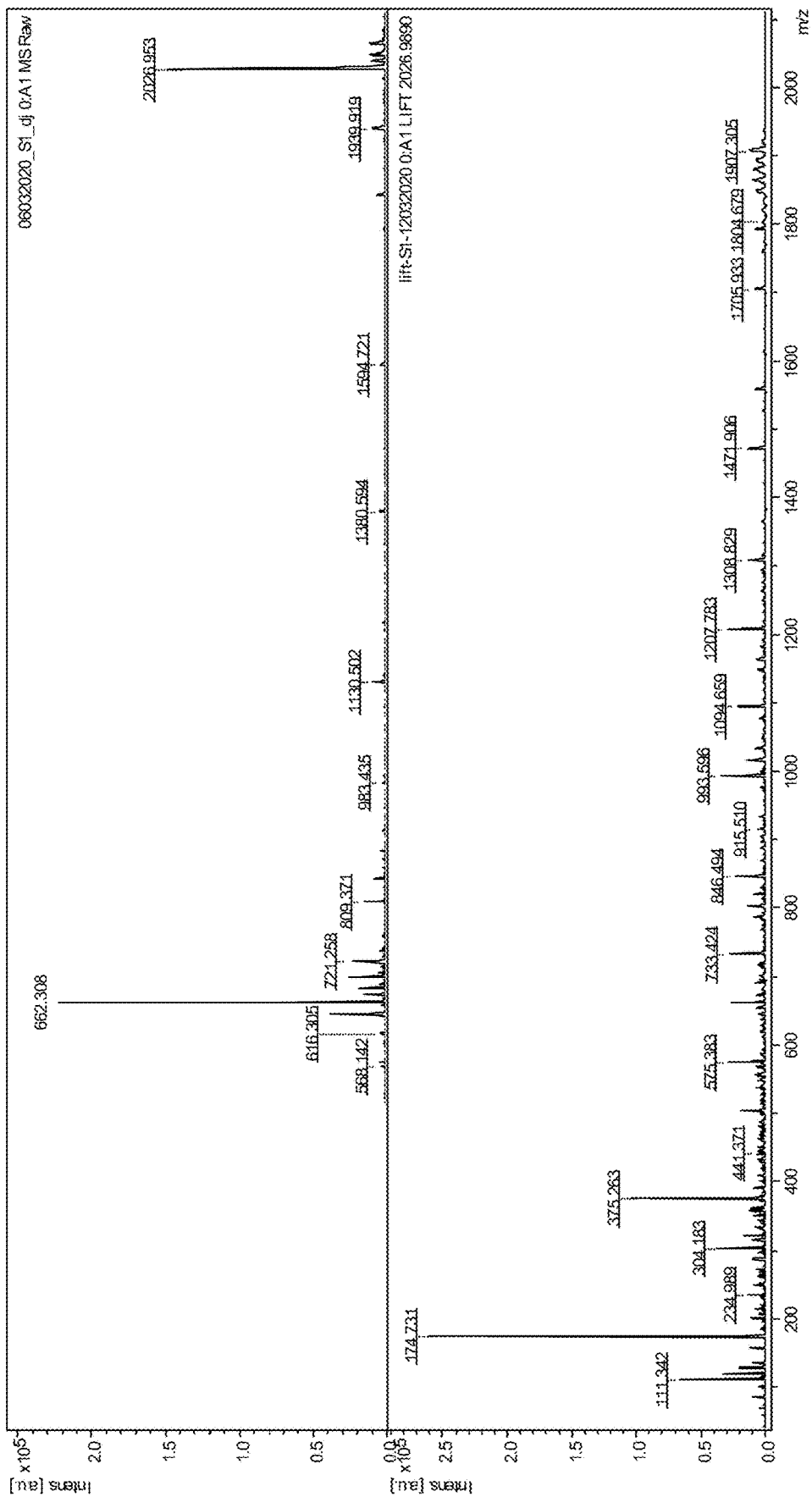

FIG. 21A depicts the Matrix-assisted laser desorption/ionization (MALDI) MS1 and MS2 spectra of the polypeptide sequence: FSSFSYTLTFLASAEAER (SEQ ID NO: 12).

Figure 21B:
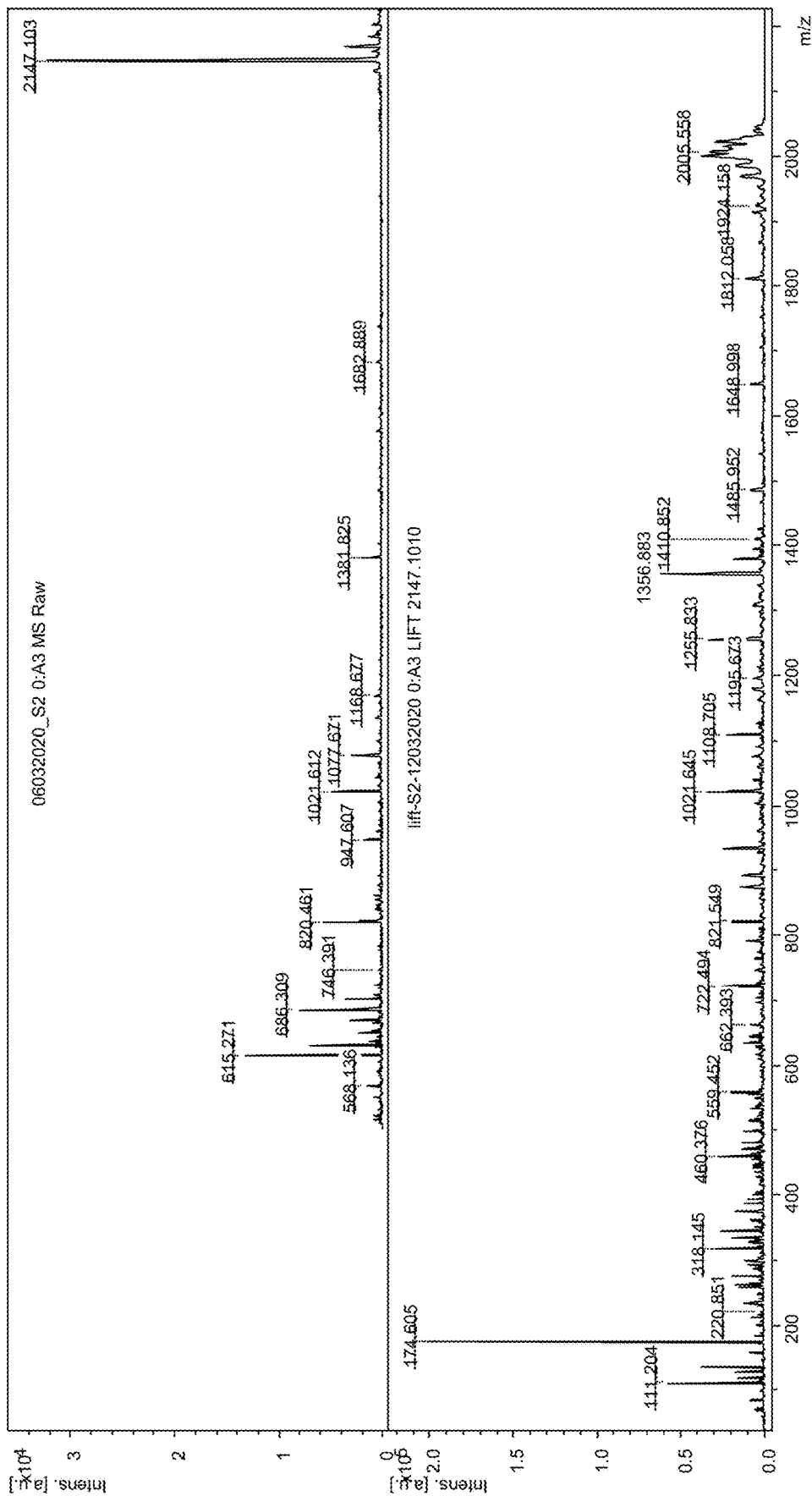

And FIG. 21B depicts the MALDI MS1 and MS2 spectra of the polypeptide sequence: FSTYYETFSSLVYVLATR (SEQ ID NO: 13).

Skilled artisans will appreciate that elements in the figures are illustrated for simplicity and clarity and have not necessarily been depicted to scale. For example, the dimensions of some of the elements in the illustrations, block diagrams or flowcharts may be exaggerated in respect to other elements to help to improve understanding of the present embodiments.

DETAILED DESCRIPTION

Embodiments of the present disclosure will be described, by way of example only, with reference to the drawings. Like reference numerals and characters in the drawings refer to like elements or equivalents.

Some portions of the description which follows are explicitly or implicitly presented in terms of algorithms and functional or symbolic representations of operations on data within a computer memory. These algorithms and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "storing", "retrieving", "encoding", "decoding", "translating", "converting", "mapping", "adding", "appending", "including", "generating", "comparing", "determining", "indicating", "detecting", "communicating", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may include a computer or other computing device selectively activated or reconfigured by a computer program stored therein. The algorithms and displays presented herein are not inherently related to any particular computer or other apparatus. Various machines may be used with programs in accordance with the teachings herein. Alternatively, the construction of more specialized apparatus to perform the required method steps may be appropriate. The structure of a computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the disclosure.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a computer. The computer readable medium may also include a hard-wired medium such as exemplified in the Internet system, or wireless medium such as exemplified in the GSM mobile telephone system. The computer program when loaded and executed on a computer effectively results in an apparatus that implements the steps of the preferred method.

In embodiments of the present disclosure, use of the term 'server' may mean a single computing device or at least a computer network of interconnected computing devices which operate together to perform a particular function. In other words, the server may be contained within a single hardware unit or be distributed among several or many different hardware units.

Term Definitions

As used herein, the terms "peptide" and "peptide sequence" refer to a string of the amino acid residues, wherein the order of the assembly of the amino acid is the peptide sequence in the peptide. As used herein, the term "amino acid" refers to an organic compound that comprises an amine group ($-NH_2$) and a carboxyl group ($-COOH$). Amino acids can be natural, unusual, unnatural or synthetic (e.g., an amino acid analog), wherein examples include, but are not limited to, D or L optical isomers, and amino acid analogs and peptidomimetics. Further examples of naturally occurring amino acids can be, but are not limited to, alanine, arginine, asparagine, aspartic acid, asparagine (or aspartic acid), cysteine, glutamic acid, glutamine, glycine, histidine, isoleucine, leucine, lysine, methionine, phenylalanine, proline, serine, threonine, tryptophan, tyrosine or valine. In another example, groups of unnatural amino acids can be, but are not limited to, beta-homo-amino acids, and N-alkyl amino acids, such as alpha-methyl and alpha-dimethyl amino acids. Further examples of unnatural, unusual occurring or synthetic amino acids include, but are not limited to, citrulline, hydroxyproline, norleucine, 3-nitrotyrosine, nitroarginine, ornithine, naphtylalanine, methionine sulfoxide, methionine sulfone, cyclohexylalanine, ring-substituted phenylalanine, tyrosine or tryptophan derivatives (including but not limited to, for example, cyano-phenylalanine, o-tyrosine, m-tyrosine, hydroxy-tryptophan, methoxy-tryptophan), or halogen-labelled amino acids derivatives (including but not limited to, for example, fluoro/chloro/bromo/iodo-phenylalanine, fluoro/chloro/bromo/iodo-tryptophan, fluoro/chloro/bromo/iodo-alanine).

Additional examples of unnatural amino acids include 3-(2-chlorophenyl)-alanine, 3-chloro-phenylalanine, 4-chloro-phenylalanine, 2-fluoro-phenylalanine, 3-fluoro-phenylalanine, 4-fluoro-phenylalanine, 2-bromo-phenylalanine, 3-bromo-phenylalanine, 4-bromo-phenylalanine, homophenylalanine, 2-methyl-phenylalanine, 3-methyl-phenylalanine, 4-methyl-phenylalanine, 2,4-dimethylphenylalanine, 2-nitro-phenylalanine, 3-nitro-phenylalanine, 4-nitro-phenylalanine, 2,4-dinitro-phenylalanine, 1,2,3,4-tetrahydroisoquinoline-3-carboxylic acid, 1,2,3,4-tetrahydronorharman-3-carboxylic acid, 1-naphthylalanine, 2-naphthylalanine, pentafluorophenyl-alanine, 2,4-dichloro-phenylalanine, 3,4-dichloro-phenyl-alanine, 3,4-difluoro-phenylalanine, 3,5-difluoro-phenylala-nine, 2,4,5-trifluoro-phenylalanine, 2-trifluoromethyl-phenylalanine, 3-trifluoromethyl-phenylalanine, 4-trifluoromethyl-phenylalanine, 2-cyano-phenylalanine, 3-cyano-phenylalanine, 4-cyano-phenylalanine, 2-iodo-phenylalanine, 3-iodo-phenylalanine, 4-iodo-phenylalanine, 4-methoxyphenylalanine, 2-aminomethyl-phenylalanine, 3-aminomethyl-phenylalanine, 4-aminomethyl-phenylala-nine, 2-carbamoyl-phenylalanine, 3-carbamoyl-phenylala-nine, 4-carbamoyl-phenylalanine, m-tyrosine, 4-amino-phe-nylalanine, styrylalanine, 2-amino-5-phenyl-pentanoic acid, 9-anthrylalanine, 4-t-butyl-phenylalanine, 3,3-diphenylala-nine, 4,4'-diphenylalanine, benzoylphenylalanine, α-methyl-phenylalanine, α-methyl-4-fluoro-phenylalanine, 4-thiazolylalanine, 3-benzothienylalanine, 2-thienylalanine, 2-(5-bromothienyl)-alanine, 3-thienylalanine, 2-furylala-nine, 2-pyridylalanine, 3-pyridylalanine, 4-pyridylalanine, 2,3-diaminopropionic acid, 2,4-diaminobutyric acid, ally-lglycine, 2-amino-4-bromo-4-pentenoic acid, propargylgly-cine, 4-aminocyclopent-2-enecarboxylic acid, 3-aminocy-clopentanecarboxylic acid, 7-amino-heptanoic acid, dipropylglycine, pipecolic acid, azetidine-3-carboxylic acid, cyclopropylglycine, cyclopropylalanine, 2-methoxy-phe-nylglycine, 2-thienylglycine, 3-thienylglycine, α-benzyl-proline, α-(2-fluoro-benzyl)-proline, α-(3-fluoro-benzyl)-proline, α-(4-fluoro-benzyl)-proline, α-(2-chloro-benzyl)-proline, α-(3-chloro-benzyl)-proline, α-(4-chloro-benzyl)-proline, α-(2-bromo-benzyl)-proline, α-(3-bromo-benzyl)-proline, α-(4-bromo-benzyl)-proline, α-phenethyl-proline, α-(2-methyl-benzyl)-proline, α-(3-methyl-benzyl)-proline, α-(4-methyl-benzyl)-proline, α-(2-nitro-benzyl)-proline, α-(3-nitro-benzyl)-proline, α-(4-nitro-benzyl)-proline, α-(1-naphthalenylmethyl)-proline, α-(2-naphthalenylm-ethyl)-proline, α-(2,4-dichloro-benzyl)-proline, α-(3,4-di-chloro-benzyl)-proline, α-(3,4-difluoro-benzyl-proline, α-(2-trifluoromethyl-benzyl)-proline, α-(3-trifluoromethyl-benzyl)-proline, α-(4-trifluoromethyl-benzyl)-proline, α-(2-cyano-benzyl)-proline, α-(3-cyano-benzyl)-proline, α-(4-cyano-benzyl)-proline, α-(2-iodo-benzyl)-proline, α-(3-iodo-benzyl)-proline, α-(4-iodo-benzyl)-proline, α-(3-phenyl-allyl)-proline, α-(3-phenyl-propyl)-proline, α-(4-t-butyl)-benzyl)-proline, α-benzhydryl-proline, α-(4-biphenylmethyl)-proline, α-(4-thiazolylmethyl)-proline, α-(2-thiophenylmethyl)-proline, α-(5-bromo-2-thiophenyl-methyl)-proline, α-(3-thiophenylmethyl)-proline, α-(2-fura-nylmethyl)-proline, α-(2-pyridinylmethyl)-proline, α-(3-pyridinylmethyl)-proline, α-(4-pyridinylmethyl)-proline, α-allyl-proline, α-propynyl-proline, γ-benzyl-proline, γ-(2-fluoro-benzyl)-proline, γ-(3-fluoro-benzyl)-proline, γ-(4-fluoro-benzyl)-proline, γ-(2-chloro-benzyl)-proline γ-(3-chloro-benzyl)-proline, γ-(4-chloro-benzyl)-proline, γ-(2-bromo-benzyl)-proline, γ-(3-bromo-benzyl)-proline, γ-(4-bromo-benzyl)-proline, γ-(2-methyl-benzyl)-proline, γ-(3-methyl-benzyl)-proline, γ-(4-methyl-benzyl)-proline, γ-(2-nitro-benzyl)-proline, γ-(3-nitro-benzyl)-proline, γ-(4-nitro-benzyl)-proline, γ-(1-naphthalenylmethyl)-proline, γ-(2-naphthalenylmethyl)-proline, γ-(2,4-dichloro-benzyl)-proline, γ-(3,4-dichloro-benzyl)-proline, γ-(3,4-difluoro-benzyl)-proline, γ-(2-trifluoromethyl-benzyl)-proline, γ-(3-trifluoromethyl-benzyl)-proline, γ-(4-trifluoromethyl-benzyl)-proline, γ-(2-cyano-benzyl)-proline, γ-(3-cyano-benzyl)-proline, γ-(4-cyano-benzyl)-proline, γ-(2-iodo-benzyl)-proline, γ-(3-iodo-benzyl)-proline, γ-(4-iodo-benzyl)-proline, γ-(3-phenyl-allyl-benzyl)-proline, γ-(3-phenyl-propyl-benzyl)-proline, γ-(4-t-butyl-benzyl)-proline, γ-benzhydryl-proline, γ-(4-biphenylmethyl)-proline, γ-(4-thiazolylmethyl)-proline, γ-(3-benzothienylmethyl)-proline, γ-(2-thienylmethyl)-proline, γ-(3-thienylmethyl)-proline, γ-(2-furanylmethyl)-proline, γ-(2-pyridinylmethyl)-proline, γ-(3-pyridinylmethyl)-proline, γ-(4-pyridinylmethyl)-pro-line, γ-allyl-proline, γ-propynyl-proline, trans-4-phenyl-pyrrolidine-3-Carboxylic acid, trans-4-(2-fluoro-phenyl)-pyrrolidine-3-carboxylic acid, trans-4-(3-fluoro-phenyl)-pyrrolidine-3-carboxylic acid, trans-4-(4-fluoro-Phenyl)-pyrrolidine-3-carboxylic acid, trans-4-(2-chloro-phenyl)-pyrrolidine-3-carboxylic acid, trans-4-(3-chloro-phenyl)-pyrrolidine-3-carboxylic acid, trans-4-(4-Chloro-phenyl)-pyrrolidine-3-carboxylic acid, trans-4-(2-bromo-phenyl)-pyrrolidine-3-carboxylic acid, trans-4-(3-bromo-phenyl)-pyrrolidine-3-carboxylic acid, trans-4-(4-bromo-phenyl)-pyrrolidine-3-carboxylic acid, trans-4-(2-methyl-phenyl)-pyrrolidine-3-carboxylic acid, trans-4-(3-methyl-phenyl)-pyrrolidine-3-carboxylic acid, trans-4-(4-methyl-phenyl)-pyrrolidine-3-carboxylic acid, trans-4-(2-nitro-phenyl)-pyrrolidine-3-carboxylic acid, trans-4-(3-nitro-phenyl)-pyrrolidine-3-carboxylic acid, trans-4-(4-nitro-phenyl)-pyrrolidine-3-carboxylic acid, trans-4-(1-naphthyl)-pyrrolidine-3-carboxylic acid, trans-4-(2-naphthyl)-pyrrolidine-3-carboxylic acid, trans-4-(2,5-dichloro-phenyl)-pyrrolidine-3-carboxylic acid, trans-4-(2,3-dichloro-phenyl)-pyrrolidine-3-carboxylic acid, trans-4-(2-trifluoromethyl-phenyl)-pyrrolidine-3-carboxylic acid, trans-4-(3-trifluoromethyl-phenyl)-pyrrolidine-3-carboxylic acid, trans-4-(4-trifluoro methyl-phenyl)-pyrrolidine-3-car-boxylic acid, trans-4-(2-cyano-phenyl)-pyrrolidine-3-car-boxylic acid, trans-4-(3-cyano-phenyl)-pyrrolidine-3-car-boxylic acid, trans-4-(4-cyano-phenyl)-pyrrolidine-3-carboxylic acid, trans-4-(3-methoxy-phenyl)-pyrrolidine-3-carboxylic acid, trans-4-(4-methoxy-phenyl)-pyrrolidine-3-carboxylic acid, trans-4-(2-hydroxy-phenyl)-pyrrolidine-3-carboxylic acid, trans-4-(3-hydroxy-phenyl)-pyrrolidine-3-carboxylic acid, trans-4-(4-hydroxy-phenyl)-pyrrolidine-3-carboxylic acid, trans-4-(2,3-dimethoxy-phenyl)-pyrrolidine-3-carboxylic acid, trans-4-(3,4-dimethoxy-phenyl)-pyrrolidine-3-carboxylic acid, trans-4-(3,5-dimethoxy-phenyl)-pyrrolidine-3-carboxylic acid, trans-4-(2-pyridinyl)-pyrrolidine-3-carboxylic acid, trans-4-(3-pyridinyl)-pyrrolidine-3-carboxylic acid, trans-4-(6-methoxy-3-pyridinyl)-pyrrolidine-3-carboxylic acid, trans-4-(4-pyridinyl)-pyrrolidine-3-carboxylic acid, trans-4-(2-thienyl)-pyrrolidine-3-carboxylic acid, trans-4-(3-thienyl)-pyrrolidine-3-carboxylic acid, trans-4-(2-furanyl)-pyrrolidine-3-carboxylic acid, trans-4-isopropyl-pyrrolidine-3-carboxylic acid, and 4-phosphonomethyl-phenylalanine.

As used herein the term "amino acid analogs" refers to synthetic or semi-synthetic analogs of naturally occurring and unnatural amino acids, which include one or more chemical modifications, including, but not limited to hydrolysis, hydroxylation, alkoxylation, alkylation, homo-analogs, nor-analogs, cyclic analogs, arylation, nitration, halogenation, N-, O-, or S-alkylation, N-, O-, or S-acylation, dehydrogenation, oxidation, reduction, and decarboxylation.

As used herein, the term "hydrophilic amino acids" refers to naturally occurring or unnatural amino acids having a hydrophilic side chain; such side chain may be uncharged, positively (cationic) or negatively charged (anionic) under normal physiological conditions, in particular at about pH 7.4. Uncharged hydrophilic amino acids can include, but are not limited to, serine, threonine, asparagine and glutamine; positively charged hydrophilic amino acids can be, but are not limited to, arginine, histidine and lysine, and the unnaturally occurring amino acid ornithine; negatively charged amino acids include aspartic acid and glutamic acid.

"Hydrophobic amino acids" refers to naturally occurring or unnatural amino acids having a hydrophobic and/or aromatic side chain, such as, but not limited to, alanine, valine, leucine, isoleucine, and the aromatic amino acids phenylalanine, tyrosine and tryptophan. Further included are unnaturally occurring amino acids such as, but not limited to, cyclohexylalanine.

As used herein, the term "peptide" refers to a polymer of 2 or more amino acids, amino acid analogs, peptidomimetics, or any combinations thereof. The subunits can be linked by peptide bonds. In another example, the subunits may be linked by other bonds such as, but not limiting to ester or ether bonds. Peptides also have a structure, wherein the structure can be generally understood to be linear or cyclic. In one example, a peptide can be, but is not limited to, dipeptides, tripeptides, oligopeptides or polypeptides. In another example, the peptide can be about 2 to 100 amino acids in length. In yet another example, the peptide can be about 2 to about 10 amino acids in length, about 5 to about 15 amino acids in length, about 10 to about 20 amino acids in length, about 15 to about 25 amino acids in length, about 20 to about 30 amino acids in length, about 25 to about 35 amino acids in length, about 30 to about 40 amino acids in length, about 35 to about 45 amino acids in length, about 40 to about 50 amino acids in length, about 45 to about 55 amino acids in length, about 50 to about 60 amino acids in length, about 55 to about 65 amino acids in length, about 60 to about 70 amino acids in length, about 65 to about 75 amino acids in length, about 70 to about 80 amino acids in length, about 75 to about 85 amino acids in length, about 80 to about 90 amino acids in length, about 85 to about 95 amino acids in length, about 90 to about 100 amino acids in length. In yet another example, the peptide can be 18 amino acids in length. Shorter peptides are cheaper to synthesize, and easier to be sequenced with reduced missed fragmentation, while longer peptides can store more data per peptide, reduce the number of peptides required for analysis, and reduce the address and error correction overhead.

As used herein, one or more amino acids in a peptide sequence represents a pattern of bits/symbols. A sequence of amino acids in a peptide sequence therefore represents a string of bits/symbols, which in turn represents part of the digital data. Therefore, the representation of digital data by peptide sequences is referred to herein as the digital data being stored in peptide sequences for simplicity sake. Since the digital data is expressed in a different form or system, the representation of digital data by peptide sequences can also be described as the digital data being encoded in peptide sequences. Therefore, the storing of digital data in peptide sequences is the same as the encoding of digital data in peptide sequences.

In the present disclosure, it is defined that $N'$ as the length of the codeword for a LDPC code;
$M'$ as the number of parity bits for a LDPC code;
$K'$ as the number of information bits for a LDPC code with $K'=N'-M'$;
$H$ as the $M' \times N'$ parity-check matrix for a LDPC code;
$h_{i,j}$ as the element in the ith row and the jth column of matrix H;
$G$ as the generator matrix for a LDPC code with $GH^T=0$;
$d=[d_1, d_2, \ldots, d_{K'}]$ as the vector of the information bits;
$p=[p_1, p_2, \ldots, p_{M'}]$ as the vector of the parity bits;
$c=[d\ p]=[d_1, d_2, \ldots, d_{K'}, p_1, p_2, \ldots, p_{M'}]$ as the codeword of a LDPC code;
partial sequence formed by consecutive amino acids as tag;
order-independent composition of amino acids as amino acid combination (AAC);
the number of amino acids used as K;
the set of the amino acids used as $A=\{a_1, a_2, \ldots, a_K\}$;
the mass set of the amino acid residues used as $g=\{g_1, g_2, \ldots, g_K\}$;
the length of the peptide sequence as N, which is the number of the amino acids in a peptide;
the peptide sequence as $P=\{P_1, P_2, \ldots, P_N\}$;
the mass set of the amino acid residues in peptide P as $m=\{m_1, m_2, \ldots, m_N\}$;
the mass of hydrogen or proton as $m_H$;
the mass of hydroxyl group as $m_{OH}$;
the 'head amino acid' is defined as the amino acid residue next to the N-terminal of the peptide that is fixed throughout all peptides;
the 'tail amino acid' is defined as the amino acid residue next to the C-terminal of the peptide that is fixed throughout all peptides;
the mass of the N-terminal functional group attached to the head amino acid as $m_{Ngroup}$, for peptides with unprotected N-terminal, this is equal to $m_H$;
the mass of the C-terminal functional group attached to the tail amino acid as $m_{Cgroup}$, for peptides with unprotected C-terminal, this is equal to $m_{OH}$;
the masses of the head and the tail amino acid residues in the sequence as $m_{head}$ and $m_{tail}$, respectively, they can be zero if there are no fixed amino acids;
the mass of the whole sequence as M, which is given by $M=\Sigma^N_{j=1} m_j + m_{Ngroup} + m_{Cgroup}$;
the mass set of the b-ions in peptide P as $m_b=\{m_{b,1}, m_{b,2}, \ldots m_{b,N+1}, m_{b,N+2}\}$, where $m_{b,i+1}=m_{b,i}+m_i$, i.e., $m_{b,1}=(m_{Ngroup}-m_H)$, $m_{b,2}=(m_{Ngroup}-m_H)+m_{head}, \ldots$ $m_{b,N}=M_H-m_{Cgroup}-m_{tail}$, $m_{b,N+1}=M-m_H-m_{Cgroup}$, $m_{b,N+2}=M$;
the mass set of the y-ions (complementary ions of b-ions) in peptide P as $m_y=\{m_{y,1}, m_{y,2}, \ldots, m_{y,N+1}, m_{y,N+2}\}$, where $m_y=M-m_b$, and $m_{y,i+1}=m_{y,i}-m_i$, i.e., $m_{y,1}=M-(m_{Ngroup}-m_H)$, $m_{y,2}=M-(m_{Ngroup}-m_H)-m_{head}, \ldots$, $m_{y,N}=m_H+M_{Cgroup}+m_{tail}$, $m_{y,N+1}=m_H+m_{Cgroup}$, $m_{y,N+2}=0$;
the mass difference set between the theoretical spectrum and the experimental spectrum as $\Delta=\{\Delta_1, \Delta_2, \ldots, \Delta_N\}$, where $\Delta_i \in [-\delta, +\delta]$, $i=1, 2, \ldots, N$, and $\delta$ is the tolerance value;
the theoretical spectrum generated by peptide P as $T(P)$;
the MS/MS spectrum obtained by tandem mass spectrometry as S;
the number of pairs of mass/charge ratio and intensity that representing the spectrum S as L;
the set of the charges for spectrum S as $z=\{z_1, z_2, \ldots, z_L\}$, usually $z_i=1, 2$, or 3;
the set of the mass/charge ratios for spectrum S as $(m/z)=\{(m/z)_1, (m/z)_2, \ldots, (m/z)_L\}$;
the number of subsets in the spectrum S as $\rho$, where in each subset, all (m/z) ratios are isotopes of a particular fragment, with a charge value equaling the inverse of difference between consecutive (m/z) ratios;
the ith subset as $G_i$, $i=1, 2, \ldots, \rho$;
the monoisotopic mass for subset $G_i$ as $m'_i$, $i=1, 2, \ldots, \rho$, which can be calculated by $m'_i=(m/z)_{i,0} z'_{i,0} - m_H z'_{i,0}$, where $(m/z)_{i,0}$ is the lowest value in subset $G_i$, and $z'_{i,0}$ is the corresponding charge for $(m/z)_{i,0}$;

the mass set of putative b-ions for spectrum S as $m'_b = \{m'_{b,1}, m'_{b,2}, \ldots, m'_{b,L}\}$, where $m'_{b,i} = (m/z)_i z_i - m_H z_i$, $i=1, 2, \ldots, L$;

the equivalent b-ion mass set of putative y-ions for spectrum S as $m'_y = \{m'_{y,1}, \ldots, m'_{y,L}\}$, where $m'_{y,i} = M - [(m/z)_i z_i - m_H z_i]$, $i=1, 2, \ldots, L$;

the set of the intensities for spectrum S as $I = \{I_1, I_2, \ldots, I_L\}$, where the intensity $I_i$ corresponds to the mass/charge ratio $(m/z)_i$ for each i, $i=1, 2, \ldots, L$;

the mass of the putative b-ion with the Jth highest intensity for spectrum S as $m'_{B,J}$;

the equivalent b-ion mass of the putative y-ion with the Jth highest intensity for spectrum S as $m'_{Y,J}$;

the number of candidate sequences as n;

the number of masses with higher ranking intensity used for the tag-finding scheme as W;

the (N−2) symbols of the peptide (excluding the head and tail) in the block as $S_1, S_2, \ldots S_{N-2}$, the order-checking bit used to protect the order of symbols $S_i$ and $S_j$ of a sequence as $Q_{i,j}$, where $\{i, j\} = \{1, 2\}, \{2, 3\}, \{15, 16\}$;

the number of information bit set asp;

the number of supplementary information bit set as γ;

the number of information bits in LDPC code or RS code as α;

the number of parity bits in LDPC code or RS code as β;

the information bit set as $b = \{b_1, b_2, \ldots, b_\mu\}$;

the supplementary information bit set as $b' = \{b'_1, b'_2, \ldots, b'_\gamma\}$;

the information bit set of the jth code as $b^{(j)} = \{b_1^{(j)}, b_2^{(j)}, \ldots, b_\alpha^{(j)}\}$, j=1, 2 and 3 for LDPC code, and j=1, 2, 3 and 4 for RS code;

the parity bit set of the jth code as $p^{(j)} = \{p_1^{(j)}, p_2^{(j)}, \ldots, p_\beta^{(j)}\}$, j=1, 2 and 3 for LDPC code, and j=1, 2, 3 and 4 for RS code;

the interleaved parity bit set of the jth code as $P^{(j)} = \{P_1^{(j)}, P_2^{(j)}, \ldots, P_\beta^{(j)}\}$, j=1, 2 and 3 for LDPC code;

the address pairs as $\{A_{i,1}, A_{i,2}, \ldots, A_{i,t}\}$, t=2 or 3, and i=1, 2, \ldots, 8^t$;

the overall code rate as R;

the code rate of the LDPC code as $R_{LDPC}$;

the code rate of the RS code as $R_{RS}$.

Storing Digital Data into Peptide Sequences

Figure 1:
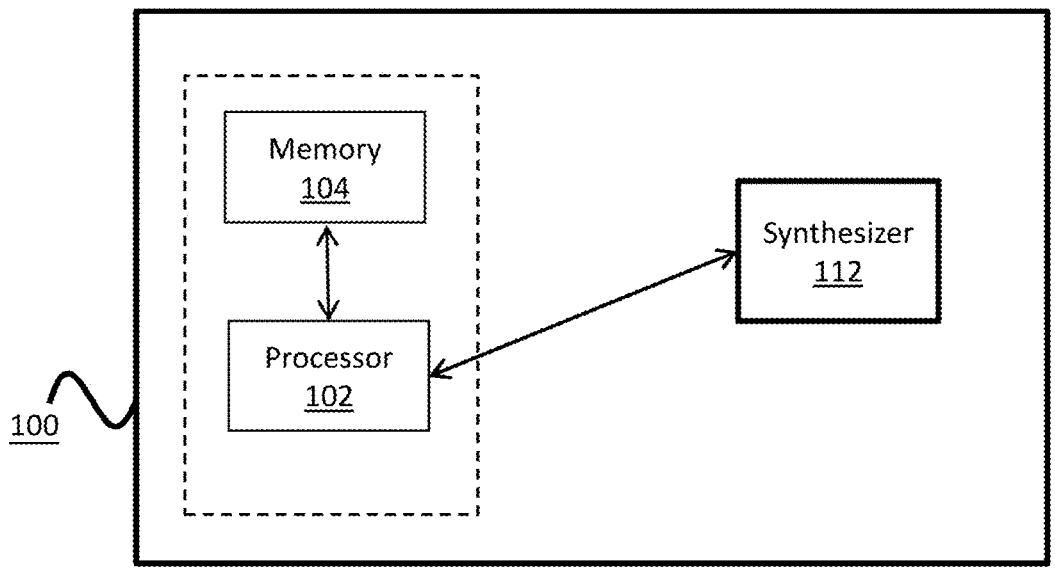
FIG. 1 depicts a schematic diagram of a system configured to store digital data into peptide sequences in accordance with embodiments of the disclosure.

Referring to FIG. 1, a schematic diagram of a system 100 configured to store digital data into peptide sequences is depicted. The system 100 includes a synthesizer 112 configured to synthesize peptide sequences, a processor 102 in communication with the synthesizer 112, and a memory 104 including computer program code. The memory 104 is in communication with the processor 102 such that the processor 102 can read the computer program code stored in the memory 104. The processor 102 can then execute the computer program code to encode digital data into peptide sequences. The processor 102 then transmits the peptide sequences to the synthesizer 112, so that the synthesizer 112 can synthesize the transmitted peptide sequences. These components can be integrated in one location or distributed among different locations, and the communications can be performed in real-time, in near-real-time, or in batches.

A synthesizer can be used to assemble amino acids into a peptide in a desired sequence. The synthesizer 112 can include, but not limited to, equipment/device for liquid-phase peptide synthesis, solid-phase peptide synthesis or microwave-assisted peptide synthesis. The synthesizer 112 can also be configured to include equipment/device for peptide purification methods, such as, but not limited to, reverse-phase chromatography, size-exclusion chromatography, ion exchange chromatography, partition chromatography, high-performance liquid chromatography, or any combinations thereof. The synthesizer 112 may be a single equipment/device or a series of equipment/devices in combination configured to synthesize the peptide sequences and/or form a mixture of peptides.

Figure 3:
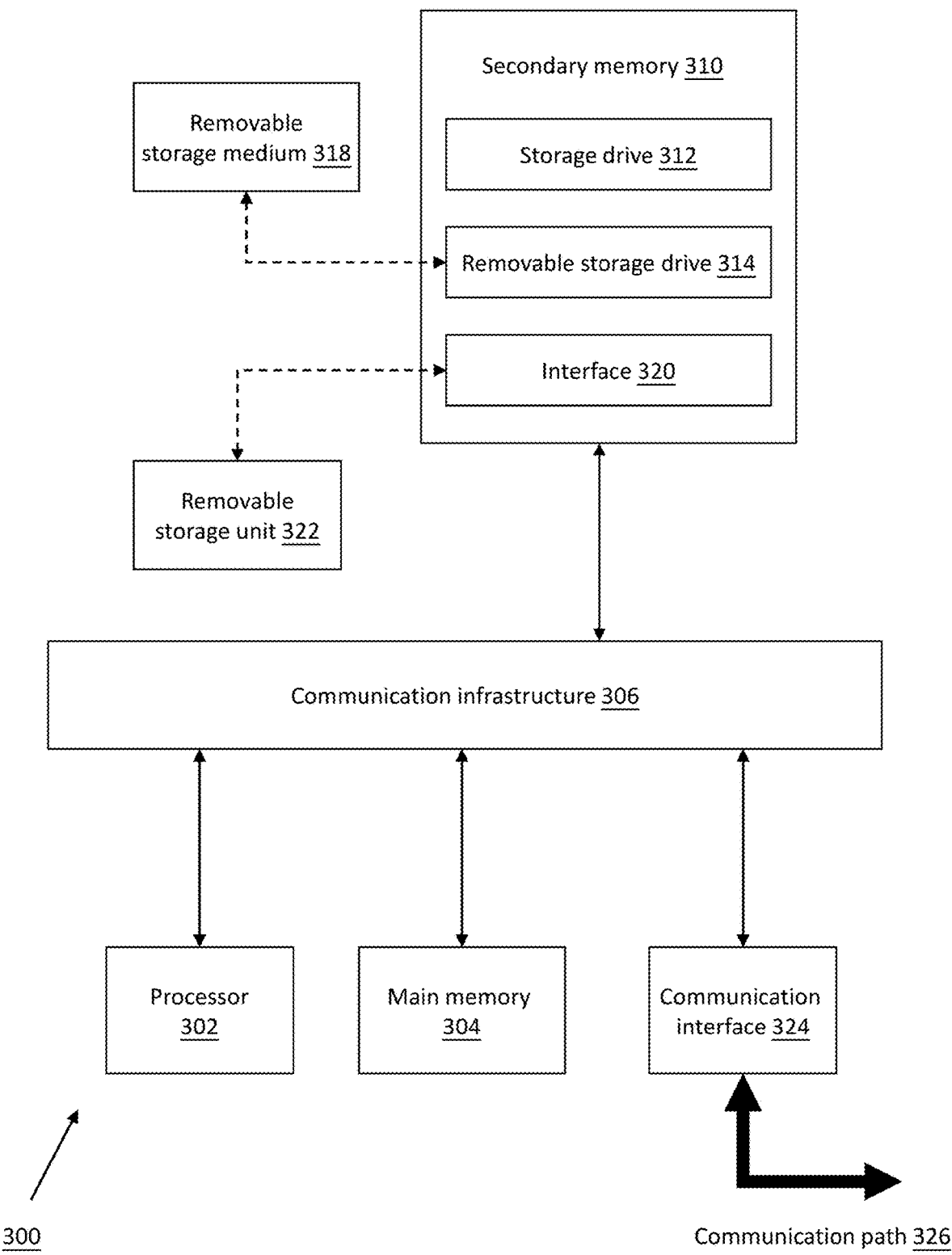
FIG. 3 depicts a schematic diagram of a computer system suitable for use in the system depicted in FIGS. 1 and 2 in accordance with embodiments of the disclosure.
Figure 4:
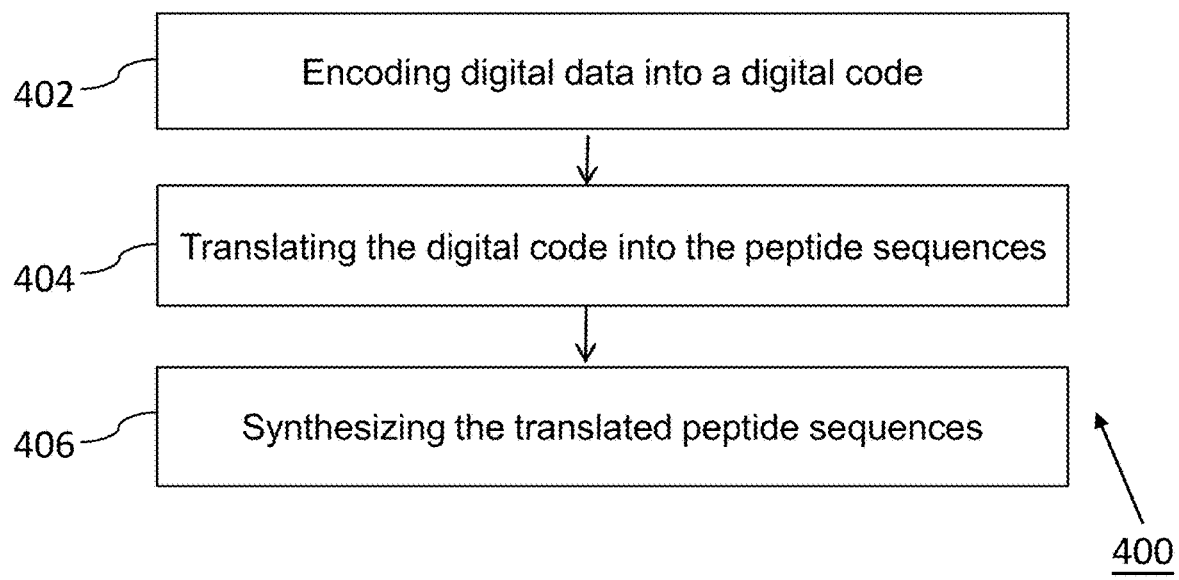
FIG. 4 depicts a flowchart illustrating a method of storing digital data into peptide sequences in accordance with embodiments of the disclosure.

The system 100 can be used to implement method 400 for storing digital data into peptide sequences as depicted in FIG. 4. The processor 102 and the memory 104 including computer program code in the system 100 can be parts of a general purpose computing device as depicted in FIG. 3, in which the processor 102 corresponds to processor 302, and the memory 104 corresponds to memory 304. The method 400 broadly includes:

step 402: encoding digital data into a digital code;

step 404: translating the digital code into peptide sequences; and step 406: synthesizing the translated peptide sequences.

At step 402, digital data can be encoded into a digital code by the processor 102. The digital data may be retrieved from the memory 104 or received from an external device (e.g., an external hard drive, an optical disc, etc.). The digital data may be in the form of video, image, audio, text, computer program, and the like. The digital data is then encoded in a digital code, for example, in a collection of bits (0s and 1s) or symbols (e.g. numbers, letters). The collection of digital code may be presented in, but not limited to, forms of strings, arrays, vectors, matrices, data blocks, and the like. In practical applications, the encoding schemes can be user-defined, and additional codes can be added during the encoding process for various purposes, such as labelling, address indication, accuracy enhancement, redundancy, and error correcting.

For data security purposes, the digital data can be scrambled or encrypted or ciphered before being encoded in a digital code, which at step 404 is translated to one or more amino acids in one or more peptides. Examples of encryption systems include Rivest-Shamir-Adleman (RSA), Elliptic Curve Cryptography (ECC), Advanced Encryption Standard (AES) and Data Encryption Standard (DES). The digital data and/or the encrypted data and/or the encoded digital code can be interleaved before being mapped to amino acids in part of a peptide, or one or more peptides.

At step 404, the digital code obtained at step 402 is translated into peptide sequences. In embodiments of the present disclosure, one or more amino acids represent a bit pattern or a symbol pattern in the digital code. For example, the amino acid serine ("S") may represent a bit pattern of 000, the amino acid threonine ("T") may represent a bit pattern of 001. A sequence of amino acids in a peptide therefore corresponds to a part of the digital code and carries part of the information of the digital data. Examples of mapping methods between amino acid(s) and bit/symbol patterns are listed below, with alanine ("A"), threonine ("T"), leucine ("L"), valine ("V"), glutamic acid ("E"), histidine ("H"), tyrosine ("Y"), phenylalanine ("F"), aspartic acid ("D"), lysine ("K"), arginine ("R"), proline ("P"), tryptophan ("W"), cysteine ("C"), glycine ("G"), serine ("S"), asparagine ("N"), and glutamine ("Q") as amino acid example representations. FIGS. 11A-S shows examples of the mapping between bit(s)/symbol(s) to amino acid(s).

Mapping method 1 Independent and fixed bit-to-amino-acid mapping, for example, Bit "0" is mapped to "A"; Bit "1" is mapped to "T" (FIG. 11A).

Mapping method 2 Independent and fixed bits-to-amino-acid mapping, for example, Bits "000" are mapped to "A"; Bits "001" are mapped to "T"; Bits "010" are mapped to "L"; Bits "011" are mapped to "V" (FIG. 11B).

Mapping method 3 Independent and fixed symbol-to-amino-acid mapping, for example, Symbols "0", "1", "2", "3", "4", "5", "6" and "7" are mapped to "A", "T", "L", "V", "E", "H", "Y" and "F", respectively (FIG. 11C).

Mapping method 4 Independent and fixed symbol-to-amino-acids mapping, for example, Symbol "0" is mapped to "AAA"; Symbol "1" is mapped to "AAT"; Symbol "7" is mapped to "TTT" (FIG. 11D).

Mapping method 5 Independent and fixed symbols-to-amino-acid mapping, for example, Symbols "00" are mapped to "A"; Symbols "01" are mapped to "T"; Symbols "22" are mapped to "D" (FIG. 11E).

Mapping method 6 Independent and fixed symbols-to-amino-acids mapping, for example, Symbols "00" are mapped to "AAA"; Symbols "01" are mapped to "AAT"; Symbols "77" are mapped to "VVV" (FIG. 11F).

Mapping method 7 Dependent and fixed bit-to-amino-acid mapping, where the current bit-to-amino-acid mapping depends on the previous amino acid, for example, if the previous amino acid is "A", then Bit "0" is mapped to "T" and Bit "1" is mapped to "A". If the previous amino acid is "T", then Bit "0" is mapped to "A" and Bit "1" is mapped to "T" (FIG. 11G) Other possible arrangements can also be used for dependent and fixed bit-to-amino-acid mapping (FIGS. 11H-J).

Mapping method 8 Dependent and fixed symbol-to-amino-acid mapping, where the current symbol-to-amino-acid mapping depends on the previous amino acid, for example, in FIG. 11K(a), if the previous amino acid is "A", then Symbols "0", "1", "2", "3", "4", "5", "6" and "7" are mapped to "T", "L", "V", "E", "H", "Y", "F" and "A", respectively; if the previous amino acid is "T", then Symbols "0", "1", "2", "3", "4", "5", "6" and "7" are mapped to "L", "V", "E", "H", "Y", "F", "A" and "T", respectively. In FIG. 11K(b), if the previous amino acid is "A", then the symbols cannot be mapped to "A" (FIGS. 11K(a), 11K(b)).

Mapping method 9 Dependent and fixed symbol-to-amino-acids mapping, where the current symbol-to-amino-acids mapping depends on the previous amino acids, for example, in FIG. 11L(a), if the previous amino acids are "AAA", then Symbols "0", "1", "2", "3", "4", "5", "6" and "7" are mapped to "AAT", "ATA", "ATT", "TAA", "TAT", "TTA", "TTT" and "AAA", respectively; if the previous amino acids are "AAT", then Symbols "0", "1", "2", "3", "4", "5", "6" and "7" are mapped to "ATA", "ATT", "TAA", "TAT", "TTA", "TTT", "AAA" and "AAT", respectively. In FIG. 11L(b), if the previous amino acids are "AAA", then the symbols cannot be mapped to "AAA" (FIGS. 11L(a), 11L(b)).

Mapping method 10 Dependent and fixed symbols-to-amino-acid mapping, where the current symbols-to-amino-acid mapping depends on the previous amino acid, for example, if the previous amino acid is "A", then Symbols "00", "01", "02", "10", "11", "12", "20", "21" and "22" are mapped to "T", "L", "V", "E", "H", "Y", "F", "D" and "A", respectively; if the previous amino acid is "T", then Symbols "00", "01", "02", "10", "11", "12", "20", "21" and "22" are mapped to "L", "V", "E", "H", "Y", "F", "D", "A" and "T", respectively (FIG. 11M).

Mapping method 11 Dependent and fixed symbols-to-amino-acids mapping, where the current symbols-to-amino-acids mapping depends on the previous amino acids, for example, if the previous amino acids are "AAA", then Symbols "00", "01", "02", "03", . . . , "76" and "77" are mapped to "AAT", "AAL", "AAV", "ATA", "VVV" and "AAA", respectively; if the previous amino acids are "AAT", then Symbols "00", "01", "02", "03", . . . , "76" and "77" are mapped to "AAL", "AAV", "ATA", "ATT", . . . , "AAA" and "AAT", respectively (FIG. 11N).

Mapping method 12 Independent and random bit-to-amino-acid mapping, where the current bit-to-amino-acid mapping is independent of the previous amino acids, for example, bit "0" is mapped to "A" or "T" or "L" or "V", where "A", "T", "L" and "V" can be selected with equal or unequal probabilities; bit "1" is mapped to "E" or "H" or "Y" or "F", where "E", "H", "Y" and "F" can be selected with equal or unequal probabilities (FIG. 11O).

Mapping method 13 Independent and random symbol-to-amino-acid mapping, where the current symbol-to-amino-acid mapping is independent of the previous amino acids, for example, symbol "0" is mapped to "A" or "T", where "A" and "T" can be selected with equal or unequal probabilities; symbol "3" is mapped to "Y" or "F", where "Y" and "F" can be selected with equal or unequal probabilities (FIG. 11P).

Mapping method 14 Independent and random symbol-to-amino-acids mapping, where the current symbol-to-amino-acids mapping is independent of the previous amino acids, for example, symbol "0" is mapped to "AAA" or "AAT", where "AAA" and "AAT" can be selected with equal or unequal probabilities; symbol "3" is mapped to "TTA" or "ITT", where "TTA" and "ITT" can be selected with equal or unequal probabilities (FIG. 11Q).

Mapping method 15 Independent and random symbols-to-amino-acid mapping, where the current symbols-to-amino-acid mapping is independent of the previous amino acids, for example, symbols "00" are mapped to "A" or "T", where "A" and "T" can be selected with equal or unequal probabilities; symbols "22" are mapped to "N" or "0", where "N" and "0" can be selected with equal or unequal probabilities (FIG. 11R).

Mapping method 16 Independent and random symbols-to-amino-acids mapping, the current symbols-to-amino-acids mapping is independent of the previous amino acids, for example, symbols "00" are mapped to "AA" or "AT" or "AL" or "AV", where "AA", "AT", "AL" and "AT" can be selected with equal or unequal probabilities; symbols "22" are mapped to "DA" or "DT" or "DL" or "DV", where "DA", "DT", "DL" and "DT" can be selected with equal or unequal probabilities (FIG. 11S).

It is to be appreciated that there can be other variations for the mapping methods, and a combination of mapping methods can be used for mapping the digital code to amino acids. It is also to be appreciated that there can be other translation methods, other than mapping, to translate the digital code to peptide sequences.

At step 406, the translated peptide sequences are synthesized into peptides. As the peptide sequences are translated from the digital code, the synthesized peptides bear digital data. In embodiments of the present disclosure, the digital data bearing peptides can be mixed to form a mixture of peptides as less space is required in comparison to storing the discrete peptides. Peptides can be synthesized by methods including, but not limited to, liquid-phase peptide synthesis, solid-phase peptide synthesis or microwave-assisted peptide synthesis. Peptides can also undergo peptide purification such that the peptides obtained are not in a mixture, wherein the peptide purification methods include, but are not limited to, reverse-phase chromatography, size-exclusion chromatography, ion exchange chromatography, partition chromatography, high-performance liquid chromatography, or any combinations thereof. Alternatively, the translated peptide sequences can be purchased commercially, isolated from a natural source directly or semi-synthetically.

The synthesized peptides and mixtures of peptides can be stored in different conditions. It would generally be understood that storage conditions are dependent on the properties of the peptides to be stored. In one example, the conditions can comprise, but not limited to, temperature or phases. In another example, peptides can be stored in the solid or liquid phase. In another example, the mixture of peptides can be kept in the dry room in a powder form or in a solution form and stored between −80° C. and −20° C.

Error-Correction Method

When performing step 402 of method 400, the digital data can be advantageously encoded to a digital code with error-correction codes. In one arrangement, the digital data is encoded in a digital code. Error-correction codes are then added to the digital code. Therefore, the error-correction codes are in addition to the digital code. Suitable error-correction methods provide the capability of recovering the original digital data when errors occur in the data storage and retrieval processes. Hereinafter, the term "starting digital code" is used to refer to the digital code generated from the original digital data. The starting digital code is a digital code without any error-correction codes.

FIG. 10 shows an example of an error-correction method. The example error-correction method adds two redundant bits to each bit in the starting digital code. Therefore, the error-correction method adds redundancy to the starting digital code. For example, bit 0 in the starting digital code is added with additional 0 bits, while bit 1 in the starting digital code is added with addition 1 bits. The digital code with the error-correction code in this example is transformed as (0, 1)→(000, 111). As used herein, the term "redundancy" refers to extra data that is generated for repetition of information or inclusion of additional information during the data storage/retrieval/transfer. By adding redundancy, error correction and detection can be advantageously achieved. In the example in FIG. 10, the error-correction method allows an error in any of the triplet of bits to be corrected by "majority vote" as demonstrated in the decoding table. The error-correction method also allows up to 2 bits of triplet omitted (not presented in the figure). It is worth noting that, although simple to implement, this triple modular redundancy is a relatively inefficient error-correction method. In the present disclosure, a more efficient error-correction method based on order-checking bits, and one or more LDPC codes or one or more RS codes is designed to correct errors during the synthesis, detection and sequencing of the peptides.

Figure 6:
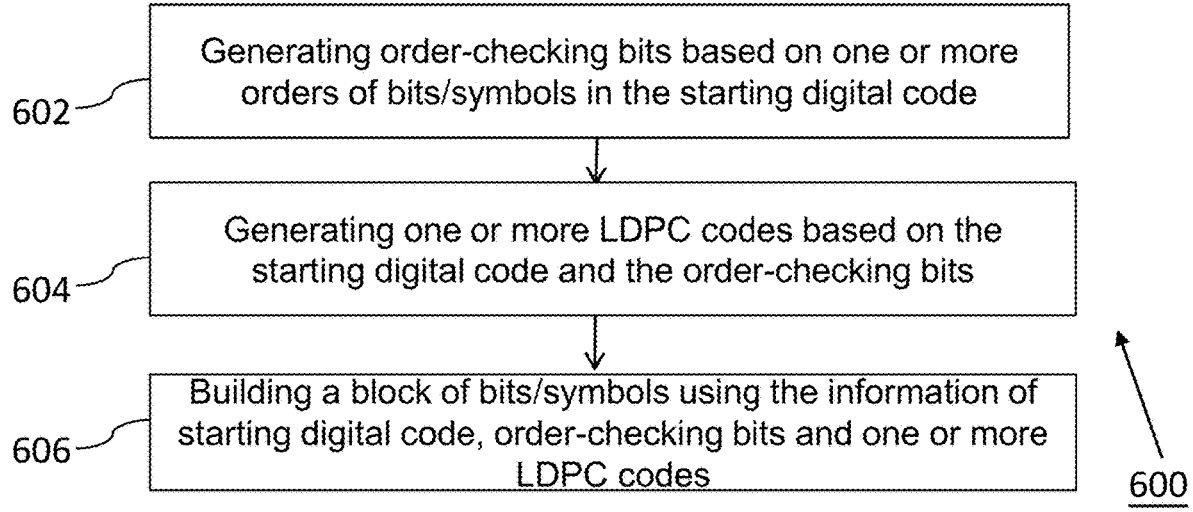
FIG. 6 depicts a flowchart illustrating a method of encoding digital data into a digital code, the digital code including order-checking bits and one or more low-density parity-check (LDPC) codes, in accordance with embodiments of the disclosure.

FIG. 6 shows a flowchart illustrating a method 600 of encoding digital data in a digital code, the digital code including order-checking bits and one or more LDPC codes. The order-checking bits and the one or more LDPC codes form an error-correction method. In one example, a digital code representing information of the digital data is provided as the starting digital code. At step 602, order-checking bits are generated based on one or more orders of bits/symbols, or segments of bits/symbols in the starting digital code. Order-checking bits have the function of protecting the correct order of bits/symbols in the starting digital code when the digital code is being processed during the data storage/retrieval/transfer.

In one arrangement, the order-checking bits are added into the starting digital code as redundant bits, which can contain information of the correct order of certain bits/symbols in the starting digital code. The value of the order-checking bits can be determined according to user-defined rules, for example, the order-checking bit of "1" is added to a symbol if the subsequent symbol has a lesser value. For example, a starting digital code has symbols of 32. An order-checking bit is then added according to the above example user-defined rules. As the first symbol has a greater value (i.e., "3" representing 3 bits "011") than the second symbol (i.e., "2" representing 3 bits "010"), a redundant bit "1" is added as an order-checking bit. The same process can be repeated for the second symbol to add an order-checking bit. Therefore, there can be one or more order-checking bits generated from the starting digital code. In one example, the generated order-checking bits can be added to the starting digital code and become part of the digital code before performing step 604.

At step 604, one or more LDPC codes are generated based on the digital code obtained from step 602. The digital code of step 602 includes the starting digital code and the order-checking bits. As such, the one or more LDPC codes are capable of correcting the starting digital code and the order-checking bits. LDPC code is a linear error-correction code constructed using a sparse bipartite graph. The encoding of LDPC codes into the digital code comprises: (1) constructing a sparse parity-check matrix, and (2) generating codewords with the matrix. A codeword contains information bits and parity bits, in which the parity bits are the redundant bits appended to the information bits. A parity bit is set to either 0 or 1 depending on the total number of the 1-bits in some of the information bits either even or odd, which can advantageously be used to detect and/or correct errors in the information bits. In alternative embodiments, error-correction codes can include any one or combination of repetition code, convolutional code, turbo code, fountain code, LDPC code, RS code, Hadamard code, and Hamming code.

At step 606, a block of bits or symbols is built using the information of the starting digital code (representing the original digital data), the order-checking bits (generated at step 602) and the one or more LDPC codes (generated at step 604). Although it is described that the digital data is encoded in a digital code having a block of bits or symbols, it is to be appreciated that the encoded digital code can be in any form determined by the user.

Example: Encoding Digital Data Using Order-Checking Bits and One or More LDPC Codes As an illustrative example of method 600, digital data is encoded in a starting digital code with 850 information bits, $b=\{b_1, b_2, \ldots, b_{850}\}$. The starting digital code is to be processed using error-correction methods and then stored into 40 16-mer peptide sequences. In other words, a starting digital code of 850 information bits together with its error-correction codes is to be translated to 40 peptide sequences, each sequence having 16 amino acids. In one arrangement, the starting digital code is encoded to 40 sequences of symbols (i.e., Seq #1, Seq #2, . . . , Seq #40), each peptide sequence having 16 symbols (i.e., $S_1, S_2, \ldots, S_{16}$) and each symbol represents a 3-bit pattern. Each symbol corresponds to an amino acid in the synthesized peptide sequence, and each sequence of symbols corresponds to a peptide sequence.

The starting digital code may be arranged in another format before adding error-correction codes. In this example, the starting digital code is reformatted into a matrix of sequences before adding the error-correction codes. Table 1 shows the sequences of symbols of this example. As shown in Table 1, each sequence (i.e., Seq #1, Seq #2, . . . , Seq #40) includes 16 symbols where 2 of the 16 symbols are used as an address pair (i.e., $\{I_{i,1}, A_{i,2}\}$, i=1, 2, . . . , 40), where i is the sequence number. In Table 1, the address pair occupies the first 2 symbols of each peptide sequence. In another arrangement, the address pair may occupy any 2 symbols of each peptide sequence.

The address pair of a peptide sequence (e.g., Seq #1) is used to indicate the position of the peptide sequence (e.g., Seq #1) in the order of the peptide sequences (e.g., Seq #1, Seq #2, etc.). For example, a peptide sequence Seq #j may have an address pair value of $A_{1,1}$ of 000 and $A_{1,2}$ of 001, which is combined to provide an address value of 000001. Further, the peptide sequence Seq #k may have an address pair value of $A_{2,1}$ of 000 and $A_{2,2}$ of 000, which is combined to provide an address value of 000000. Therefore, based on the address value, the peptide sequences of Table 1 commence with Seq #k followed by Seq #j. As such, when retrieving the data from the synthesized peptide by sequencing, the address pairs of the peptide sequences indicate the correct order of the peptide sequences, and in turn allow the digital code (inclusive of any error-correction codes) to be reconstructed based on order indicated by the address pairs. The addressing of the peptide sequences may also use more or less than 2 symbols of a peptide sequence.

Due to the 2-symbol address pairs, 14 symbols in a 16-mer peptide sequence are available to represent the information bits. Therefore, a total of 560 symbols are available in the 40 peptide sequences to represent the 850 information bits. In one arrangement, the information bits b are filled in the data block according to the following arrangements:

Bits $b_1$-$b_{400}$ are filled in the second and the third bits of Symbols $S_3$-$S_7$ of the peptide sequences Seq #1 to Seq #40;

Bits $b_{401}$-$b_{760}$ are filled in Symbols $S_{14}$-$S_{16}$ of the peptide sequences Seq #1 to Seq #40;

Bits $b_{761}$-$b_{850}$ are filled in Symbol $S_{13}$ of the peptide sequences Seq #11 to Seq #40; and Bits $b_{851}$-$b_{970}$ are filled in the first bit of Symbols $S_4$-$S_6$ and are set to be zero. These bits are set to zero so that there are at least three symbols in each sequence with values 0, 1, 2, 3. In some embodiments, the amino acids to be mapped to 3-bit symbols with values of 0, 1, 2, and 3 are hydrophilic amino acids.

As can be seen in Table 1, there are also order-checking bits Q and redundant bits $P_i^{(j)}$, i=1, 2, . . . , β, j=1, 2 and 3, of LDPC codes in the peptide sequences. The order-checking bits Q are added at step 602 and the redundant bits $P_i^{(j)}$ of LDPC codes are added at step 604.

Starting at step 602, order-checking bits are generated based on the digital code arranged in Table 1. For each of the 40 peptide sequences, two order-checking bits are generated to protect the order of (i) $S_1$ and $S_2$, and (ii) $S_{15}$ and $S_{16}$, respectively. The order of $S_1$ and $S_2$ is protected by symbol $S_3$ and the order of $S_{15}$ and $S_{16}$ is protected by symbol $S_7$. In one arrangement, the first bit of symbol $S_3$ ($Q_{1,2}$) is an order-checking bit that protects the order of $S_1$ and $S_2$. The order of $S_{15}$ and $S_{16}$ is protected by an order-checking bit in the first bit of symbol $S_7$ ($Q_{15,16}$). In other arrangements, the second or third bit in the 3-bit symbol $S_3$ or $S_7$ may be used as the order-checking bit.

Therefore, in this example, the first bit of $S_3$ ($Q_{1,2}$) checks the order of symbols $S_1$ and $S_2$, and the first bit of $S_7$ ($Q_{15,16}$) checks the order of symbols $S_{15}$ and $S_{16}$. In this example, the user-defined rule which determines the value of an order-checking bit is:

if the value of symbol $S_i$ is larger than or equal to the value of symbol $S_{i+1}$, the order-checking bit is assigned as "1"; and if the value of symbol $S_i$ is smaller than the value of symbol $S_{i+1}$, the order-checking bit is assigned as "0".

For example, if $S_{15}$=101 and $S_{16}$=001, the value of the order-checking bit ($Q_{15,16}$) in symbol $S_7$ is "1" according to the rule. Also, if $S_1$=110 and $S_2$=111, the value of the order-checking bit ($Q_{1,2}$) in symbol $S_3$ is "0" according to the rule. It is possible to generate the order-checking bits based on other user-defined rules that are not presented here. It is also possible to use different user-defined rules to generate different order-checking bits in the same digital code.

At step 604, one or more LDPC codes are generated based on the starting digital code and the order-checking bits. Three LDPC codes are used in the example shown in Table 1. In this example, symbols $S_8$ to $S_{12}$ (in peptide sequences Seq #1 to Seq #40) and symbol $S_{13}$ (in peptide sequences Seq #1 to Seq #10) are filled with the parity bits generated by the LDPC codes. The number of parity bits in the peptide sequences of Table 1 is 630, and the total number of bits to be encoded is 1050 (inclusive of 850 information bits b, 120 bits of zero bits, and 80 bits of order-checking bits). In this embodiment, the address pairs are not included in the 1050 bits for LDPC encoding purpose, which allows more amino acids to be used for storing digital data. In other words, the number of information bits/symbols corresponding to the digital data is increased in the 40×16 data block. During the decoding process, the address pairs are assumed to be correct, based on which the peptide sequences can be arranged. In some other embodiments, the address pairs can be included in the information bits and considered for LDPC encoding, or other error-correction codes. In particular, if the length of each peptide is much longer (e.g. 500-mer), it is more efficient to encode each peptide separately to protect its address and the digital data stored in the peptide. For this example with 1050 bits to be encoded by LDPC, if one LDPC code is generated, the LDPC code should have a codeword comprising 1680 bits, represented as (1680, 1050). Since there is a total of 850 information bits, the overall code rate R is R=850/1680=0.5060. In a preferred method, since there are 3 bits for each symbol, three (560, 350) LDPC codes are generated instead of one (1680, 1050) LDPC code, and the code rate of the LDPC code $R_{LDPC}$ is $R_{LDPC}$=350/560=0.625. In an alternative embodiment, since the bits of the 3-bit symbols can be divided into 3 sets, it is possible to use 3 different error-correction codes which may have dissimilar error-correcting capabilities, thereby in combination providing a more robust and efficient error-correction performance. In other words, the jth (j=1, 2 and 3) bits of all the symbols after step 602 (all 40 sequences of Symbols $S_3$-$S_7$ and $S_{14}$-$S_{16}$ and the last 30 sequences of $S_{13}$) are passed to the jth LDPC code as the information bits. The three (560, 350) LDPC codes are generated based on the encoding process below.

TABLE 1

40 × 16 block of 3-bit symbols including 850 information bits, 80 order-checking bits and 3 LDPC codes.

| Symbol | $S_1$ | $S_2$ | $S_3$ | $S_4$ | $S_5$ | $S_6$ | $S_7$ | $S_8$ | $S_9$ | $S_{10}$ | $S_{11}$ | $S_{12}$ | $S_{13}$ | $S_{14}$ | $S_{15}$ | $S_{16}$ |
|---|---|---|---|---|---|---|---|---|---|---|---|---|---|---|---|---|
| Seq #1 | $A_{1,1}$ | $A_{1,2}$ | $Q_{1,2}$ | $b_{851}$ | $b_{852}$ | $b_{853}$ | $Q_{15,16}$ | $P_1^{(1)}$ | $P_2^{(1)}$ | $P_3^{(1)}$ | $P_4^{(1)}$ | $P_5^{(1)}$ | $P_{201}^{(1)}$ | $b_{401}$ | $b_{402}$ | $b_{403}$ |
| | | | $b_1$ | $b_2$ | $b_3$ | $b_4$ | $b_5$ | $P_1^{(2)}$ | $P_2^{(2)}$ | $P_3^{(2)}$ | $P_4^{(2)}$ | $P_5^{(2)}$ | $P_{201}^{(2)}$ | $b_{404}$ | $b_{405}$ | $b_{406}$ |
| | | | $b_6$ | $b_7$ | $b_8$ | $b_9$ | $b_{10}$ | $P_1^{(3)}$ | $P_2^{(3)}$ | $P_3^{(3)}$ | $P_4^{(3)}$ | $P_5^{(3)}$ | $P_{201}^{(3)}$ | $b_{407}$ | $b_{408}$ | $b_{409}$ |
| Seq #2 | $A_{2,1}$ | $A_{2,2}$ | $Q_{1,2}$ | $b_{854}$ | $b_{854}$ | $b_{856}$ | $Q_{15,16}$ | $P_6^{(1)}$ | $P_7^{(1)}$ | $P_8^{(1)}$ | $P_9^{(1)}$ | $P_{10}^{(1)}$ | $P_{202}^{(1)}$ | $b_{410}$ | $b_{411}$ | $b_{412}$ |
| | | | $b_{11}$ | $b_{12}$ | $b_{13}$ | $b_{14}$ | $b_{15}$ | $P_6^{(2)}$ | $P_7^{(2)}$ | $P_8^{(2)}$ | $P_9^{(2)}$ | $P_{10}^{(2)}$ | $P_{202}^{(2)}$ | $b_{413}$ | $b_{414}$ | $b_{415}$ |
| | | | $b_{16}$ | $b_{17}$ | $b_{18}$ | $b_{19}$ | $b_{20}$ | $P_6^{(3)}$ | $P_7^{(3)}$ | $P_8^{(3)}$ | $P_9^{(3)}$ | $P_{10}^{(3)}$ | $P_{202}^{(3)}$ | $b_{416}$ | $b_{417}$ | $b_{418}$ |
| Seq #3 | $A_{3,1}$ | $A_{3,2}$ | $Q_{1,2}$ | $b_{857}$ | $b_{858}$ | $b_{859}$ | $Q_{15,16}$ | $P_{11}^{(1)}$ | $P_{12}^{(1)}$ | $P_{13}^{(1)}$ | $P_{14}^{(1)}$ | $P_{15}^{(1)}$ | $P_{203}^{(1)}$ | $b_{419}$ | $b_{420}$ | $b_{421}$ |
| | | | $b_{21}$ | $b_{22}$ | $b_{23}$ | $b_{24}$ | $b_{25}$ | $P_{11}^{(2)}$ | $P_{12}^{(2)}$ | $P_{13}^{(2)}$ | $P_{14}^{(2)}$ | $P_{15}^{(2)}$ | $P_{203}^{(2)}$ | $b_{422}$ | $b_{423}$ | $b_{424}$ |
| | | | $b_{26}$ | $b_{27}$ | $b_{28}$ | $b_{29}$ | $b_{30}$ | $P_{11}^{(3)}$ | $P_{12}^{(3)}$ | $P_{13}^{(3)}$ | $P_{14}^{(3)}$ | $P_{15}^{(3)}$ | $P_{203}^{(3)}$ | $b_{425}$ | $b_{426}$ | $b_{427}$ |
| Seq #10 | $A_{10,1}$ | $A_{10,2}$ | $Q_{1,2}$ | $b_{878}$ | $b_{879}$ | $b_{880}$ | $Q_{15,16}$ | $P_{46}^{(1)}$ | $P_{47}^{(1)}$ | $P_{48}^{(1)}$ | $P_{49}^{(1)}$ | $P_{50}^{(1)}$ | $P_{210}^{(1)}$ | $b_{482}$ | $b_{483}$ | $b_{484}$ |
| | | | $b_{91}$ | $b_{92}$ | $b_{93}$ | $b_{94}$ | $b_{95}$ | $P_{46}^{(2)}$ | $P_{47}^{(2)}$ | $P_{48}^{(2)}$ | $P_{49}^{(2)}$ | $P_{50}^{(2)}$ | $P_{210}^{(2)}$ | $b_{485}$ | $b_{486}$ | $b_{487}$ |
| | | | $b_{96}$ | $b_{97}$ | $b_{98}$ | $b_{99}$ | $b_{100}$ | $P_{46}^{(3)}$ | $P_{47}^{(3)}$ | $P_{48}^{(3)}$ | $P_{49}^{(3)}$ | $P_{50}^{(3)}$ | $P_{210}^{(3)}$ | $b_{488}$ | $b_{489}$ | $b_{490}$ |
| Seq #11 | $A_{11,1}$ | $A_{11,2}$ | $Q_{1,2}$ | $b_{881}$ | $b_{882}$ | $b_{883}$ | $Q_{15,16}$ | $P_{51}^{(1)}$ | $P_{52}^{(1)}$ | $P_{53}^{(1)}$ | $P_{54}^{(1)}$ | $P_{55}^{(1)}$ | $b_{761}$ | $b_{491}$ | $b_{492}$ | $b_{493}$ |
| | | | $b_{101}$ | $b_{102}$ | $b_{103}$ | $b_{104}$ | $b_{105}$ | $P_{51}^{(2)}$ | $P_{52}^{(2)}$ | $P_{53}^{(2)}$ | $P_{54}^{(2)}$ | $P_{55}^{(2)}$ | $b_{762}$ | $b_{494}$ | $b_{495}$ | $b_{496}$ |
| | | | $b_{106}$ | $b_{107}$ | $b_{108}$ | $b_{109}$ | $b_{110}$ | $P_{51}^{(3)}$ | $P_{52}^{(3)}$ | $P_{53}^{(3)}$ | $P_{54}^{(3)}$ | $P_{55}^{(3)}$ | $b_{763}$ | $b_{497}$ | $b_{498}$ | $b_{499}$ |
| Seq #39 | $A_{39,1}$ | $A_{39,2}$ | $Q_{1,2}$ | $b_{965}$ | $b_{966}$ | $b_{967}$ | $Q_{15,16}$ | $P_{191}^{(1)}$ | $P_{192}^{(1)}$ | $P_{193}^{(1)}$ | $P_{194}^{(1)}$ | $P_{195}^{(1)}$ | $b_{845}$ | $b_{743}$ | $b_{744}$ | $b_{745}$ |
| | | | $b_{381}$ | $b_{382}$ | $b_{383}$ | $b_{384}$ | $b_{385}$ | $P_{191}^{(2)}$ | $P_{192}^{(2)}$ | $P_{193}^{(2)}$ | $P_{194}^{(2)}$ | $P_{195}^{(2)}$ | $b_{846}$ | $b_{746}$ | $b_{747}$ | $b_{748}$ |
| | | | $b_{386}$ | $b_{387}$ | $b_{388}$ | $b_{389}$ | $b_{390}$ | $P_{191}^{(3)}$ | $P_{192}^{(3)}$ | $P_{193}^{(3)}$ | $P_{194}^{(3)}$ | $P_{195}^{(3)}$ | $b_{847}$ | $b_{749}$ | $b_{750}$ | $b_{751}$ |
| Seq #40 | $A_{40,1}$ | $A_{40,2}$ | $Q_{1,2}$ | $b_{968}$ | $b_{969}$ | $b_{970}$ | $Q_{15,16}$ | $P_{196}^{(1)}$ | $P_{197}^{(1)}$ | $P_{198}^{(1)}$ | $P_{199}^{(1)}$ | $P_{200}^{(1)}$ | $b_{848}$ | $b_{752}$ | $b_{753}$ | $b_{754}$ |
| | | | $b_{391}$ | $b_{392}$ | $b_{393}$ | $b_{394}$ | $b_{395}$ | $P_{196}^{(2)}$ | $P_{197}^{(2)}$ | $P_{198}^{(2)}$ | $P_{199}^{(2)}$ | $P_{200}^{(2)}$ | $b_{849}$ | $b_{755}$ | $b_{756}$ | $b_{757}$ |
| | | | $b_{396}$ | $b_{397}$ | $b_{398}$ | $b_{399}$ | $b_{400}$ | $P_{196}^{(3)}$ | $P_{197}^{(3)}$ | $P_{198}^{(3)}$ | $P_{199}^{(3)}$ | $P_{200}^{(3)}$ | $b_{850}$ | $b_{758}$ | $b_{759}$ | $b_{760}$ |

Given a M'×N' parity-check matrix H for the LDPC code of length N'. In theory, the information bits (d) are encoded by using $$c = dG \text{ with } GH^T = 0, \quad (1)$$

where the superscript $^T$ is the transpose operator, $c=[d\ p]=[d_1, d_2, \ldots, d_{K'}, p_1, p_2, \ldots, p_{M'}]$ represents a codeword, $d=[d_1, d_2, \ldots, d_{K'}]$ is the vector of the information bits with $K'=N'-M'$, and $p=[p_1, p_2, \ldots, p_{M'}]$ is the vector of the parity bits. G is the generator matrix and 0 is the all-zero matrix. Then the information bits can be decoded by $$cH^T = 0. \quad (2)$$

Based on Eq. (2), it can be obtained that $$\sum_{j=1}^{K'} h_{i,j} d_j + \sum_{l=1}^{M'} h_{i,K+l} p_l = 0 \bmod 2, i = 1, 2, \ldots, M' \quad (3)$$

where $h_{i,j}$ represents the element in the ith row and the jth column of matrix H.

Generally, the generator matrix G is difficult to be obtained when the code length is long. Hence, the structured code is used for easy encoding purpose. A simple example for the code with the dual-diagonal structure is shown in Table 2, the 6×16 parity-check matrix represents a LDPC code with length of 16. Then there are 10 information bits (i.e., $d_1$, $d_2, \ldots, d_{10}$) and 6 parity bits (i.e., $p_1, p_2, \ldots, p_6$). The parity bits can be evaluated by using the information bits as follows $$p_1 = d_1 + d_4 + d_8 \bmod 2; \quad (4)$$

$$p_2 = d_3 + d_6 + d_7 + p_1 \bmod 2; \quad (5)$$

$$p_3 = d_2 + d_5 + d_9 + p_2 \bmod 2; \quad (6)$$

$$p_4 = d_1 + d_6 + d_{10} + p_3 \bmod 2; \quad (7)$$

$$p_5 = d_2 + d_4 + d_7 + d_8 + p_4 \bmod 2; \quad (8)$$

$$p_6 = d_3 + d_5 + d_9 + d_{10} + p_5 \bmod 2. \quad (9)$$

Thus the codeword is formed by a set of 16 bits $\{d_1, d_2, \ldots, d_{10}, p_1, p_2, \ldots, p_6\}$.

The decoding is performed such that all information bits can fulfill all of the above equations. Suppose that the information bit $d_1$ is missing in the received sequence. Then $d_1$ can be estimated by applying Eq. (4) or (7)

$$d_1 = d_4 + d_8 + p_1 \bmod 2; \quad (10)$$

$$d_1 = d_6 + d_{10} + p_3 + p_4 \bmod 2. \quad (11)$$

Usually, the LDPC code can be decoded by using the iterative message-passing algorithms to find a codeword C such that $cH^T = 0$ (T. Richardson and R. Urbanke, "The capacity of low-density parity check codes under message-passing decoding," IEEE Trans. Inf. Theory, vol. 47, no. 2, pp. 599-618, 2001).

TABLE 2

Example of a parity-check matrix H for the LDPC code.

| $b_1$ | $b_2$ | $b_3$ | $b_4$ | $b_5$ | $b_6$ | $b_7$ | $b_8$ | $b_9$ | $b_{10}$ | $p_1$ | $p_2$ | $p_3$ | $p_4$ | $p_5$ | $p_6$ |
|---|---|---|---|---|---|---|---|---|---|---|---|---|---|---|---|
| 1 | 0 | 0 | 1 | 0 | 0 | 0 | 1 | 0 | 0 | 1 | 0 | 0 | 0 | 0 | 0 |
| 0 | 0 | 1 | 0 | 0 | 1 | 1 | 0 | 0 | 0 | 1 | 1 | 0 | 0 | 0 | 0 |
| 0 | 1 | 0 | 0 | 1 | 0 | 0 | 0 | 1 | 0 | 0 | 1 | 1 | 0 | 0 | 0 |
| 1 | 0 | 0 | 0 | 0 | 1 | 0 | 0 | 0 | 1 | 0 | 0 | 1 | 1 | 0 | 0 |
| 0 | 1 | 0 | 1 | 0 | 0 | 1 | 1 | 0 | 0 | 0 | 0 | 0 | 1 | 1 | 0 |
| 0 | 0 | 1 | 0 | 1 | 0 | 0 | 0 | 1 | 1 | 0 | 0 | 0 | 0 | 1 | 1 |

Proceeding to step 606, 630 parity bits of the three (560, 350) LDPC codes are filled in the available bits of the 40×16 data block. In a preferred embodiment, due to the dual-diagonal structure of parity check matrix and the peptide error pattern, a random interleaver can be added to the output of each LDPC code to disturb the orders of the parity bits before inputting the LDPC code into the peptide sequences. Interleaving is a process of arranging data in a non-contiguous manner. It is common that errors occur to a number of bits/symbols in a digital code during the data storage/retrieval/transfer. When interleaving is applied, the errors affect bits/symbols that are not in fact next to one another when the digital code was created. As a result, when the data is de-interleaved, the errors are spread throughout the digital code rather than being focused in a particular spot, which makes it easier for error detection and correction. As an example, at step 706 of the method 700 (see FIG.

7 and associated discussion below), if the orders of the estimated symbols do not match with the first bits of the estimated symbols $S_3$ and $S_7$ (the order-checking bits), the corresponding symbol sequences in the data block are erased. When this happens, the LDPC decoding process is needed to retrieve these erased bits/symbols. By using an interleaver, it can advantageously ensure that these erased bits/symbols are not consecutive bits/symbols of an LDPC code. Instead, the erased bits/symbols are uniformly or randomly distributed in the LDPC code, which makes the recovery process easier.

In this example, the output parity-bit set of the jth LDPC code is defined as $p^{(j)}=\{p_1^{(j)} p_2^{(j)}, \ldots, p_{210}^{(j)}\}$ (j=1, 2 and 3), and the interleaved parity-bit set for the jth LDPC code is defined as $P^{(j)}=\{P_1^{(j)}, P_2^{(j)}, \ldots, P_{210}^{(j)}\}$ (j=1, 2 and 3). The set $P^{(j)}$ corresponds to set $p^{(j)}$(j=1, 2 and 3). The set $P^{(j)}$(j=1, 2 and 3) is arranged in the jth bits of Symbols $S_8$, $S_9$, $S_{10}$, $S_{11}$ and $S_{12}$ for all sequences, and Symbol $S_{13}$ of the first 10 sequences. In the end, the output 40×16 data block has 40×16×3=1920 bit positions, with 850 information bits, 120 bits of zero bits, 240 bits of address pairs, 80 bits of order-checking bits and 630 parity bits in the LDPC code.

Other Error-Correction Method: Reed-Soloman Code

Reed-Soloman (RS) code can alternatively be used for the error-correction method for step 604. Assume that the requirements for the coding scheme are:

(i) 10% of the 3-symbol sequences $\{S_5S_6S_7\}$ and $\{S_8S_9S_{10}\}$ cannot be recovered correctly;
(ii) 15% of the 3-symbol sequences $\{S_{11}S_{12}S_{13}\}$ and $\{S_{14}S_{15}S_{16}\}$ cannot be recovered correctly; and
(iii) the order of symbols $S_1$ and $S_2$, the order of symbols $S_2$ and $S_3$, and the order of symbols $S_{15}$ and $S_{16}$ in a sequence may be exchanged.

The error-correction method includes: (i) three order-checking bits for each peptide sequence with the first order-checking bit to protect the order of the first two symbols, the second order-checking bit to protect the order of the second and the third symbols, and the third order-checking bit to protect the order of the last two symbols in each sequence; and (ii) four RS codes to recover the original data even when any arbitrary 10% 3-symbol sequences $\{S_5S_6S_7\}$, any arbitrary 10% 3-symbol sequences $\{S_8S_9S_{10}\}$, any arbitrary 15% 3-symbol sequences $\{S_{11}S_{12}S_{13}\}$, and any arbitrary 15% 3-symbol sequences $\{S_{14}S_{15}S_{16}\}$, cannot be recovered correctly.

Assuming the digital code is stored into 511 peptide sequences of length of 16 amino acids. Accordingly, a 511×16 block of symbols is constructed (Table 3), which comprises 511×16×3=24528 bits. The 3-symbol sets $\{A_{i,1}, A_{i,2}, A_{i,3}\}$, i=1, 2, ..., 511 are used for addressing, with Symbols $S_1$ to $S_3$ having the values of {0 0 0}, {0 0 1}, {0 0 2}, ..., {7 7 5}, {7 7 6}. The three bits of Symbol $S_4$ are the three order-checking bits used to protect the order of Symbols $S_1$ and $S_2$, the order of Symbols $S_2$ and $S_3$, and the order of Symbols $S_{15}$ and $S_{16}$, respectively. Then there are 511×12×3=18396 bit positions in Symbols $S_5$ to $S_{16}$ of the block to store the information and parity bits for the RS codes.

Due to different protection requirements for partial sequences $\{S_5S_6S_7S_8S_9S_{10}\}$ and $\{S_{11}S_{12}S_{13}S_{14}S_{15}S_{16}\}$, two (511, 409) RS codes are used for partial sequences $\{S_5S_6S_7\}$ and $\{S_8S_9S_{10}\}$, another two (511, 357) RS codes are used for partial sequences $\{S_{11}S_{12}S_{13}\}$ and $\{S_{14}S_{15}S_{16}\}$. Each symbol in RS code comprises 9 bits. The first 102 rows of $\{S_5S_6S_7S_8S_9S_{10}\}$ and the first 154 rows of $\{S_{11}S_{12}S_{13}S_{14}S_{15}S_{16}\}$ are used to record the parity symbols of the (511, 409) and (511, 357) RS codes, respectively. For example, the 9 bits $p_1^{(j)}, p_2^{(j)}, \ldots, p_9^{(j)}$ (j=1, 2, 3 and 4) of Sequence 1 represent the first parity symbol in the jth RS code. The remaining rows are used to store the information bits. For example, the 9 bits $b_1, b_2, \ldots, b_9$ in $\{S_5S_6S_7\}$ of Sequence 103, and the 9 bits $b_{19}, b_{20}, \ldots, b_{27}$ in $\{S_5S_6S_7\}$ of Sequence 104, are convert to two symbols of the first RS code. Similarly, the 9 bits $b_{10}, b_{11}, \ldots, b_{18}$ in $\{S_8S_9S_{10}\}$ of Sequence 103, and the 9 bits $b_{28}, b_{29}, \ldots, b_{36}$ in $\{S_8S_9S_{10}\}$ of Sequence 104, form two symbols of the second RS code. The (511, 409) RS and (511, 357) RS codes can correct up to 51 and 77 9-bit symbol errors, respectively. The code rates $R_{RS}$ of the (511, 409) and (511, 357) RS codes are given by $R_{RS}=409/511=0.8004$, and $R_{RS}=357/511=0.6986$, respectively. Moreover, the numbers of total information bits and total parity bits of all four RS codes are given by (409+357)×2×9=13788 and (102+154)×2×9=4608, respectively. Then the maximum overall code rate R of the block can be calculated by R=13788/24528=0.5621.

Assuming that there are two sets of information data, 13656 information bits in Set b and 96 information bits in Set b'. Then the overall code rate R of the block is given by R=13752/24528=0.5607. All 13752 information bits are filled in Symbols $\{S_5S_6S_7S_8S_9S_{10}\}$ of Sequences 103 to 511 and Symbols $\{S_{11}S_{12}S_{13}S_{14}S_{15}S_{16}\}$ of Sequences 155 to 511. The information set b' is arranged in the last 3 sequences. The remaining 13788−13752=36 information bit positions in the block are set to zeros because no more information needs to be sent. These zero-bit positions are located at the first bits in $S_{16}$ of Sequences 485 to 508, the first bits in $S_{15}$ of Sequences 509 to 511, and the 3 bits in Symbol $S_{16}$ of Sequences 509 to 511.

TABLE 3

511 × 16 block of 3-bit symbols including 13752 information bits, 1533 order-checking bits and 4 RS codes.

| Symbol | $S_1$ | $S_2$ | $S_3$ | $S_4$ | $S_5$ | $S_6$ | $S_7$ | $S_8$ | $S_9$ | $S_{10}$ | $S_{11}$ | $S_{12}$ | $S_{13}$ | $S_{14}$ | $S_{15}$ | $S_{16}$ |
|---|---|---|---|---|---|---|---|---|---|---|---|---|---|---|---|---|
| Seq #1 | $A_{1,1}$ | $A_{1,2}$ | $A_{1,3}$ | $Q_{1,2}$ | $p_1^{(1)}$ | $p_4^{(1)}$ | $p_7^{(1)}$ | $p_1^{(2)}$ | $p_4^{(2)}$ | $p_7^{(2)}$ | $p_1^{(3)}$ | $p_4^{(3)}$ | $p_7^{(3)}$ | $p_1^{(4)}$ | $p_4^{(2)}$ | $p_7^{(4)}$ |
| | | | | $Q_{2,3}$ | $p_2^{(1)}$ | $p_5^{(1)}$ | $p_8^{(1)}$ | $p_2^{(2)}$ | $p_5^{(2)}$ | $p_8^{(2)}$ | $p_2^{(3)}$ | $p_5^{(3)}$ | $p_8^{(3)}$ | $p_2^{(4)}$ | $p_5^{(4)}$ | $p_8^{(4)}$ |
| | | | | $Q_{15,16}$ | $p_3^{(1)}$ | $p_6^{(1)}$ | $p_9^{(1)}$ | $p_3^{(2)}$ | $p_6^{(2)}$ | $p_9^{(2)}$ | $p_3^{(3)}$ | $p_6^{(3)}$ | $p_9^{(3)}$ | $p_3^{(4)}$ | $p_6^{(4)}$ | $p_9^{(4)}$ |
| Seq #2 | $A_{2,1}$ | $A_{2,2}$ | $A_{2,3}$ | $Q_{1,2}$ | $p_{10}^{(1)}$ | $p_{13}^{(1)}$ | $p_{16}^{(1)}$ | $p_{10}^{(2)}$ | $p_{13}^{(2)}$ | $p_{16}^{(2)}$ | $p_{10}^{(3)}$ | $p_{13}^{(3)}$ | $p_{16}^{(3)}$ | $p_{10}^{(4)}$ | $p_{13}^{(4)}$ | $p_{16}^{(4)}$ |
| | | | | $Q_{2,3}$ | $p_{11}^{(1)}$ | $p_{14}^{(1)}$ | $p_{17}^{(1)}$ | $p_{11}^{(2)}$ | $p_{14}^{(2)}$ | $p_{17}^{(2)}$ | $p_{11}^{(3)}$ | $p_{14}^{(3)}$ | $p_{17}^{(3)}$ | $p_{11}^{(4)}$ | $p_{14}^{(4)}$ | $p_{17}^{(4)}$ |
| | | | | $Q_{15,16}$ | $p_{12}^{(1)}$ | $p_{15}^{(1)}$ | $p_{18}^{(1)}$ | $p_{12}^{(2)}$ | $p_{15}^{(2)}$ | $p_{18}^{(2)}$ | $p_{12}^{(3)}$ | $p_{15}^{(3)}$ | $p_{18}^{(3)}$ | $p_{12}^{(4)}$ | $p_{15}^{(4)}$ | $p_{18}^{(4)}$ |
| Seq #102 | $A_{102,1}$ | $A_{102,2}$ | $A_{102,3}$ | $Q_{1,2}$ | $p_{910}^{(1)}$ | $p_{913}^{(1)}$ | $p_{916}^{(1)}$ | $p_{910}^{(2)}$ | $p_{913}^{(2)}$ | $p_{916}^{(2)}$ | $p_{910}^{(3)}$ | $p_{913}^{(3)}$ | $p_{916}^{(3)}$ | $p_{910}^{(4)}$ | $p_{913}^{(4)}$ | $p_{916}^{(4)}$ |
| | | | | $Q_{2,3}$ | $p_{911}^{(1)}$ | $p_{914}^{(1)}$ | $p_{917}^{(1)}$ | $p_{911}^{(2)}$ | $p_{914}^{(2)}$ | $p_{917}^{(2)}$ | $p_{911}^{(3)}$ | $p_{914}^{(3)}$ | $p_{917}^{(3)}$ | $p_{911}^{(4)}$ | $p_{914}^{(4)}$ | $p_{917}^{(4)}$ |
| | | | | $Q_{15,16}$ | $p_{912}^{(1)}$ | $p_{915}^{(1)}$ | $p_{918}^{(1)}$ | $p_{912}^{(2)}$ | $p_{915}^{(2)}$ | $p_{918}^{(2)}$ | $p_{912}^{(3)}$ | $p_{915}^{(3)}$ | $p_{918}^{(3)}$ | $p_{912}^{(4)}$ | $p_{915}^{(4)}$ | $p_{918}^{(4)}$ |
| Seq #103 | $A_{103,1}$ | $A_{103,2}$ | $A_{103,3}$ | $Q_{1,2}$ | $b_1$ | $b_4$ | $b_7$ | $b_{10}$ | $b_{13}$ | $b_{16}$ | $p_{919}^{(3)}$ | $p_{922}^{(3)}$ | $p_{925}^{(3)}$ | $p_{919}^{(4)}$ | $p_{922}^{(4)}$ | $p_{925}^{(4)}$ |
| | | | | $Q_{2,3}$ | $b_2$ | $b_5$ | $b_8$ | $b_{11}$ | $b_{14}$ | $b_{17}$ | $p_{920}^{(3)}$ | $p_{923}^{(3)}$ | $p_{926}^{(3)}$ | $p_{920}^{(4)}$ | $p_{923}^{(4)}$ | $p_{926}^{(4)}$ |
| | | | | $Q_{15,16}$ | $b_3$ | $b_6$ | $b_9$ | $b_{12}$ | $b_{15}$ | $b_{18}b$ | $p_{921}^{(3)}$ | $p_{924}^{(3)}$ | $p_{927}^{(3)}$ | $p_{921}^{(4)}$ | $p_{924}^{(4)}$ | $p_{927}^{(4)}$ |

TABLE 3-continued

511 × 16 block of 3-bit symbols including 13752 information bits, 1533 order-checking bits and 4 RS codes.

| Symbol | $S_1$ | $S_2$ | $S_3$ | $S_4$ | $S_5$ | $S_6$ | $S_7$ | $S_8$ | $S_9$ | $S_{10}$ | $S_{11}$ | $S_{12}$ | $S_{13}$ | $S_{14}$ | $S_{15}$ | $S_{16}$ |
|---|---|---|---|---|---|---|---|---|---|---|---|---|---|---|---|---|
| Seq #104 | $A_{104,1}$ | $A_{104,2}$ | $A_{104,3}$ | $Q_{1,2}$ | $b_{19}$ | $b_{22}$ | $b_{25}$ | $b_{28}$ | $b_{31}$ | $b_{34}$ | $p_{928}^{(3)}$ | $p_{931}^{(3)}$ | $p_{934}^{(3)}$ | $p_{928}^{(4)}$ | $p_{931}^{(4)}$ | $p_{934}^{(4)}$ |
| | | | | $Q_{2,3}$ | $b_{20}$ | $b_{23}$ | $b_{26}$ | $b_{29}$ | $b_{32}$ | $b_{35}$ | $p_{929}^{(3)}$ | $p_{932}^{(3)}$ | $p_{935}^{(3)}$ | $p_{929}^{(4)}$ | $p_{932}^{(4)}$ | $p_{935}^{(4)}$ |
| | | | | $Q_{15,16}$ | $b_{21}$ | $b_{24}$ | $b_{27}$ | $b_{30}$ | $b_{33}$ | $b_{36}$ | $p_{930}^{(3)}$ | $p_{933}^{(3)}$ | $p_{936}^{(3)}$ | $p_{930}^{(4)}$ | $p_{933}^{(4)}$ | $p_{936}^{(4)}$ |
| Seq #154 | $A_{154,1}$ | $A_{154,2}$ | $A_{154,3}$ | $Q_{1,2}$ | $b_{919}$ | $b_{922}$ | $b_{925}$ | $b_{928}$ | $b_{931}$ | $b_{934}$ | $p_{1378}^{(3)}$ | $p_{1381}^{(3)}$ | $p_{1384}^{(3)}$ | $p_{1378}^{(4)}$ | $p_{1381}^{(4)}$ | $p_{1384}^{(4)}$ |
| | | | | $Q_{2,3}$ | $b_{920}$ | $b_{923}$ | $b_{926}$ | $b_{929}$ | $b_{932}$ | $b_{935}$ | $p_{1379}^{(3)}$ | $p_{1382}^{(3)}$ | $p_{1385}^{(3)}$ | $p_{1379}^{(4)}$ | $p_{1382}^{(4)}$ | $p_{1385}^{(4)}$ |
| | | | | $Q_{15,16}$ | $b_{921}$ | $b_{924}$ | $b_{927}$ | $b_{930}$ | $b_{933}$ | $b_{936}$ | $p_{1380}^{(3)}$ | $p_{1383}^{(3)}$ | $p_{1386}^{(3)}$ | $p_{1380}^{(4)}$ | $p_{1383}^{(4)}$ | $p_{1386}^{(4)}$ |
| Seq #155 | $A_{155,1}$ | $A_{156,2}$ | $A_{156,3}$ | $Q_{1,2}$ | $b_{937}$ | $b_{940}$ | $b_{943}$ | $b_{946}$ | $b_{949}$ | $b_{952}$ | $b_{97309}$ | $b_{7312}$ | $b_{7315}$ | $b_{7318}$ | $b_{7321}$ | $b_{7324}$ |
| | | | | $Q_{2,3}$ | $b_{938}$ | $b_{941}$ | $b_{944}$ | $b_{947}$ | $b_{950}$ | $b_{953}$ | $b_{7310}$ | $b_{7313}$ | $b_{7316}$ | $b_{7319}$ | $b_{7322}$ | $b_{7325}$ |
| | | | | $Q_{15,16}$ | $b_{939}$ | $b_{942}$ | $b_{945}$ | $b_{948}$ | $b_{951}$ | $b_{954}$ | $b_{7311}$ | $b_{7314}$ | $b_{7317}$ | $b_{7320}$ | $b_{7323}$ | $b_{7326}$ |
| Seq #156 | $A_{156,1}$ | $A_{156,2}$ | $A_{156,3}$ | $Q_{1,2}$ | $b_{955}$ | $b_{958}$ | $b_{961}$ | $b_{964}$ | $b_{967}$ | $b_{970}$ | $b_{7327}$ | $b_{7330}$ | $b_{7333}$ | $b_{7336}$ | $b_{7339}$ | $b_{7342}$ |
| | | | | $Q_{2,3}$ | $b_{956}$ | $b_{959}$ | $b_{962}$ | $b_{965}$ | $b_{968}$ | $b_{971}$ | $b_{7328}$ | $b_{7331}$ | $b_{7334}$ | $b_{7337}$ | $b_{7340}$ | $b_{7343}$ |
| | | | | $Q_{15,16}$ | $b_{957}$ | $b_{960}$ | $b_{963}$ | $b_{966}$ | $b_{969}$ | $b_{972}$ | $b_{9729}$ | $b_{7332}$ | $b_{7335}$ | $b_{7338}$ | $b_{7341}$ | $b_{7344}$ |
| Seq #485 | $A_{485,1}$ | $A_{485,2}$ | $A_{485,3}$ | $Q_{1,2}$ | $b_{6877}$ | $b_{6880}$ | $b_{6883}$ | $b_{6886}$ | $b_{6889}$ | $b_{6892}$ | $b_{13249}$ | $b_{13252}$ | $b_{13255}$ | $b_{13258}$ | $b_{13261}$ | 0 |
| | | | | $Q_{2,3}$ | $b_{6878}$ | $b_{6881}$ | $b_{6884}$ | $b_{6887}$ | $b_{6890}$ | $b_{6893}$ | $b_{13250}$ | $b_{13253}$ | $b_{13256}$ | $b_{13259}$ | $b_{13262}$ | $b_{13264}$ |
| | | | | $Q_{15,16}$ | $b_{6879}$ | $b_{6882}$ | $b_{6885}$ | $b_{6888}$ | $b_{6891}$ | $b_{6894}$ | $b_{13251}$ | $b_{13254}$ | $b_{13257}$ | $b_{13260}$ | $b_{13263}$ | $b_{13265}$ |
| Seq #508 | $A_{508,1}$ | $A_{508,2}$ | $A_{508,3}$ | $Q_{1,2}$ | $b_{7291}$ | $b_{7294}$ | $b_{7297}$ | $b_{7300}$ | $b_{7303}$ | $b_{7306}$ | $b_{13640}$ | $b_{13643}$ | $b_{13646}$ | $b_{13649}$ | $b_{13652}$ | 0 |
| | | | | $Q_{2,3}$ | $b_{7292}$ | $b_{7295}$ | $b_{7298}$ | $b_{7301}$ | $b_{7304}$ | $b_{7307}$ | $b_{13641}$ | $b_{13644}$ | $b_{13647}$ | $b_{13650}$ | $b_{13653}$ | $b_{13655}$ |
| | | | | $Q_{15,16}$ | $b_{7293}$ | $b_{7296}$ | $b_{7299}$ | $b_{7302}$ | $b_{7305}$ | $b_{7308}$ | $b_{13642}$ | $b_{13645}$ | $b_{13648}$ | $b_{13651}$ | $b_{13654}$ | $b_{13656}$ |
| Seq #509 | $A_{509,1}$ | $A_{509,2}$ | $A_{509,3}$ | $Q_{1,2}$ | $b'_1$ | $b'_4$ | $b'_7$ | $b'_{10}$ | $b'_{13}$ | $b'_{16}$ | $b'_{55}$ | $b'_{58}$ | $b'_{61}$ | $b'_{64}$ | 0 | 0 |
| | | | | $Q_{2,3}$ | $b'_2$ | $b'_5$ | $b'_8$ | $b'_{11}$ | $b'_{14}$ | $b'_{17}$ | $b'_{56}$ | $b'_{59}$ | $b'_{62}$ | $b'_{65}$ | $b'_{67}$ | 0 |
| | | | | $Q_{15,16}$ | $b'_3$ | $b'_6$ | $b'_9$ | $b'_{12}$ | $b'_{15}$ | $b'_{18}$ | $b'_{57}$ | $b'_{60}$ | $b'_{63}$ | $b'_{66}$ | $b'_{68}$ | 0 |
| Seq #510 | $A_{510,1}$ | $A_{510,2}$ | $A_{510,3}$ | $Q_{1,2}$ | $b'_{19}$ | $b'_{22}$ | $b'_{25}$ | $b'_{28}$ | $b'_{31}$ | $b'_{34}$ | $b'_{69}$ | $b'_{72}$ | $b'_{75}$ | $b'_{78}$ | 0 | 0 |
| | | | | $Q_{2,3}$ | $b'_{20}$ | $b'_{23}$ | $b'_{26}$ | $b'_{29}$ | $b'_{32}$ | $b'_{35}$ | $b'_{70}$ | $b'_{73}$ | $b'_{76}$ | $b'_{79}$ | $b'_{81}$ | 0 |
| | | | | $Q_{15,16}$ | $b'_{21}$ | $b'_{24}$ | $b'_{27}$ | $b'_{30}$ | $b'_{33}$ | $b'_{36}$ | $b'_{71}$ | $b'_{74}$ | $b'_{77}$ | $b'_{80}$ | $b'_{82}$ | 0 |
| Seq #511 | $A_{511,1}$ | $A_{511,2}$ | $A_{511,3}$ | $Q_{1,2}$ | $b'_{37}$ | $b'_{40}$ | $b'_{43}$ | $b'_{46}$ | $b'_{49}$ | $b'_{52}$ | $b'_{83}$ | $b'_{86}$ | $b'_{89}$ | $b'_{92}$ | 0 | 0 |
| | | | | $Q_{2,3}$ | $b'_{38}$ | $b'_{41}$ | $b'_{44}$ | $b'_{47}$ | $b'_{50}$ | $b'_{53}$ | $b'_{84}$ | $b'_{87}$ | $b'_{90}$ | $b'_{93}$ | $b'_{95}$ | 0 |
| | | | | $Q_{15,16}$ | $b'_{39}$ | $b'_{42}$ | $b'_{45}$ | $b'_{48}$ | $b'_{51}$ | $b'_{54}$ | $b'_{85}$ | $b'_{88}$ | $b'_{91}$ | $b'_{94}$ | $b'_{96}$ | 0 |

Example: Storing Texts into Peptide Sequences

Figure 8:
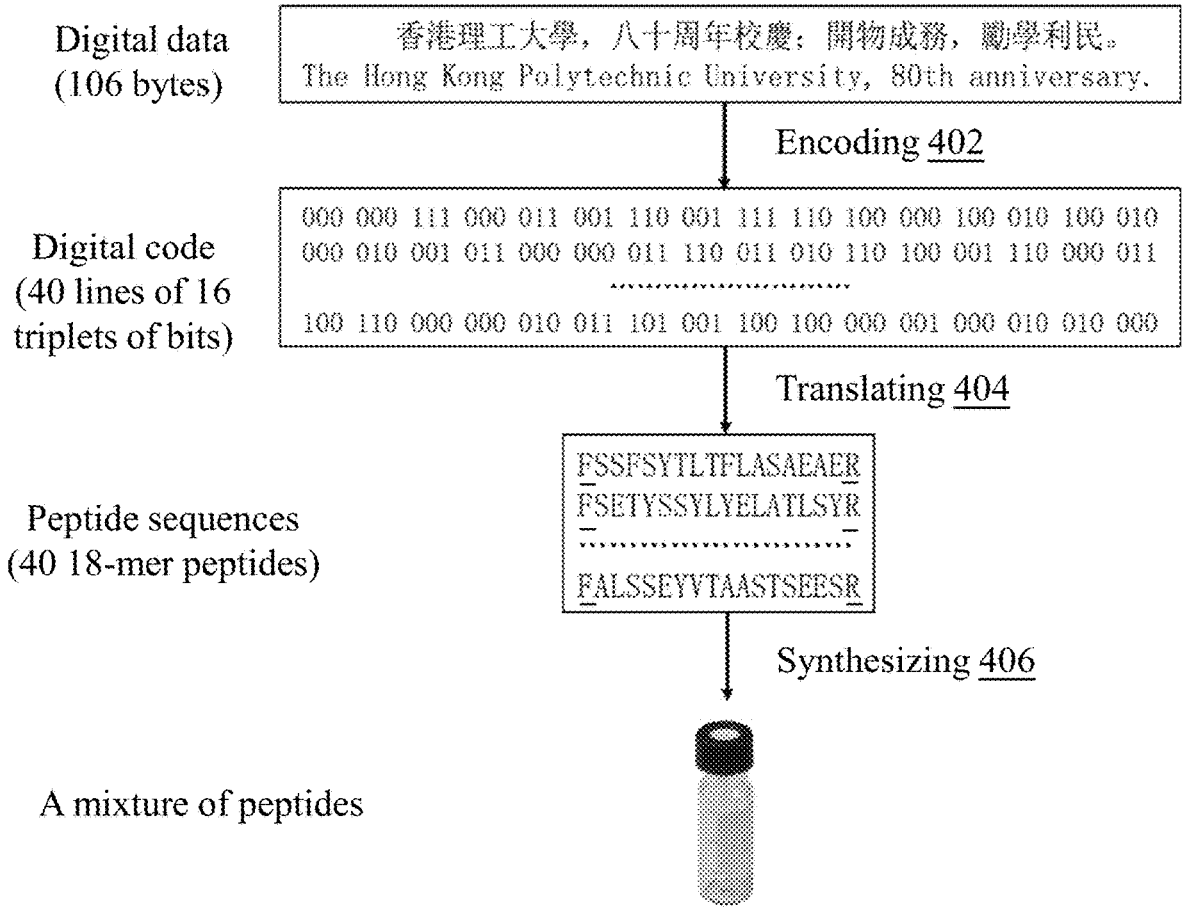
FIG. 8 depicts an illustration of storing digital data into peptide sequences in accordance with embodiments of the disclosure.

Referring to FIG. 8, an illustration 800 of storing digital data into peptide sequences in accordance with embodiments of the disclosure is depicted. Performing step 402 of method 400, the 848 bits long text symbol for "The Hong Kong Polytechnic University, 80th anniversary." in both Chinese and English and the motto of The Hong Kong Polytechnic University (PolyU) in Chinese, in BIG5 encoding, is encoded in a digital code having 40 lines of 16 triplets of bits. An error-correction method with LDPC code as described in method 600 is used at the encoding step 402. Performing step 602 of method 600, order-checking bits are added. The order-checking bits are generated to protect the order of the first and second symbols and the order of the first and second last symbols in a peptide sequence. Performing step 604 of method 600, 3 LDPC codes are used to encode the 848 bits long text symbol and the order-checking bits to 40 lines of data, each line with 16 triplets of bits. The LDPC codes are designed with the aim to recover the raw digital data when any arbitrary 10% of peptides cannot be retrieved, in case of insufficient signals in MS/MS spectra.

Performing step 404 of method 400, the digital code are then translated into 40 18-mer peptide sequences using an independent and fixed bits-to-amino-acid mapping. As discussed in the present disclosure, amino acid in the peptide sequence can be digital data bearing or non-digital data bearing. The peptides in the example are of the format of F-[16 residues]-R, in which: (i) there are 18 amino acids in each peptide; (ii) the amino acids at the N-terminal and C-terminal of each peptide are known (F and R) and do not carry any information (non-digital data bearing), and only 16 amino acids are taken into account for each peptide in the coding scheme; and (iii) 8 different amino acids (S, T, E, Y, A, V, L, and F) are used for translating the digital code (000, 001, 010, 011, 100, 101, 110, and 111). Performing step 406 of method 400, the 40 translated peptide sequences are synthesized into peptide sequences by the synthesizer 112, mixed into a mixture of peptides, and stored in a suitable condition.

As described above, by adopting error-correction methods for encoding or by using non-digital data bearing amino acids for synthesis purpose, the amount of amino acids in the peptides that can carry digital data is reduced. It is desirable to have efficient error-correction methods that enable a minimal amount of redundancy but still can protect the integrity of the digital data stored in the peptide sequences. One or more amino acids in a peptide sequence can be used to represent the identity (e.g. the address and version) of the peptide, and one or more amino acids in a peptide sequence can be used for identifying errors and/or checking the integrity of the peptide.

In consideration of the various factors such as cost of synthesis, the amino acids are selected and length of the peptides is optimized to minimize the sequencing error while maximizing data storage. Shorter peptides are cheaper to synthesize and easier to be sequenced with reduced missed cleavage, but longer peptides can store more data per peptide, reduce the number of peptides required for analysis, and reduce the address and error correction overhead. In an embodiment, 8 natural amino acids are selected, and the length of peptide is 18 amino acids long. In alternative embodiments, the length of the peptide can be varied, the set of amino acids can be expanded by incorporating unnatural amino acids, and distinct functional groups, or affinity labels, together with enrichment strategy or selection strategy during MS/MS (such as precursor ion scan or neutral loss scan), can be incorporated to allow selective retrieval of specific peptides to increase signal-to-noise ratios.

For detection and identification purposes, peptides can be labelled. In one example, the label can be at the N- or C-terminal of the peptide. In yet another example, the label can be, but is not limited to, amino acids, affinity labels, solubilisation labels, chromatography labels, epitope labels, fluorescence labels, radioisotope labels, or combinations thereof. In yet another example, the label can be bromine or chlorine labelled amino acids attached to either N-terminal or C-terminal of peptides such that the digital data bearing peptides can be identified in MS spectra and the direction of peptides can be identified in MS/MS spectra. The bromine or chlorine may also be labelled to an unnatural amino acid. In yet another example, the label can be an isotope labelled molecule bound to the N-terminal or side-chain of the peptide, such that when the digital data bearing peptides are fragmented, the appearance of the specific peaks related to the labelled molecule on MS/MS spectra indicates the presence of digital data bearing peptides. In yet another example, the label can be non-digital data bearing amino acids.

In the present disclosure, the peptide sequence determines the physicochemical properties of the peptide, which can be critical to achieve optimal peptide structures to store digital data and to retrieve digital data by sequencing. In one example, the physicochemical property can be, but is not limited to, physical, chemical and molecular properties. In another example, the physicochemical property comprises, but is not limited to, hydrophobicity, solubility, charge, stability, 3-dimensional peptide structure, signal strength, mass, polarizability, freezing point, boiling point, melting point, infrared spectrum, viscosity, density or combinations thereof.

The physicochemical properties of the peptide can be influenced by a multitude of properties such as, but not limited to, peptide length, amino acid charge, amino acid stability, amino acid polarity, amino acid pKa, amino acid hydrophilicity, amino acid hydrophobicity, amino acid order/position, or any combinations thereof, which can be modified to achieve an optimal peptide structure having improved properties, such as improved water solubility, peptide stability and digital data retrieval.

Retrieving Digital Data from Peptide Sequences

Figure 2:
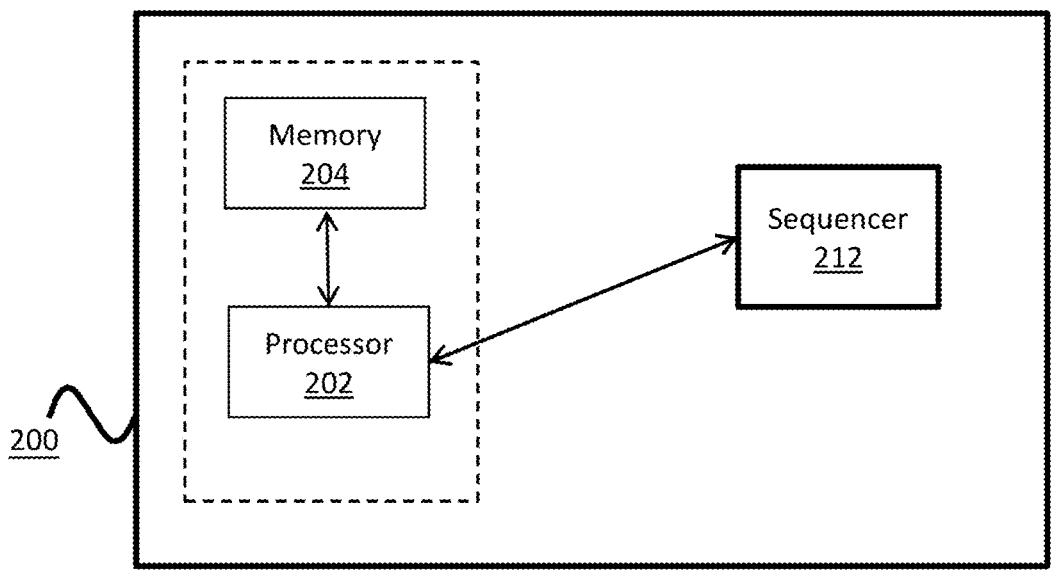
FIG. 2 depicts a schematic diagram of a system configured to retrieve digital data from peptide sequences in accordance with embodiments of the disclosure.

Referring to FIG. 2, a schematic diagram of a system 200 configured to retrieve digital data from peptide sequences is depicted. The system 200 includes a sequencer 212 configured to sequence and determine an order of the peptide sequences, a processor 202 in communication with the sequencer 212, and a memory 204 including computer program code. The memory 204 is in communication with the processor 202 such that the processor 202 can read the computer program code stored in the memory 204. The processor 202 can then execute the computer program code to decode peptide sequences received from the sequencer 212 to digital data. The processor 202 receives the peptide sequences from the sequencer 212, which determines stored peptide sequences. These components can be integrated in one location or distributed among different locations, and the communications can be performed in real-time, in near-real-time, or in batches.

The sequencer 212 can include equipment/device such as, but not limited to, gel electrophoresis apparatus, high performance liquid chromatography (HPLC) machine, capillary electrophoresis apparatus, ionizer, and mass spectrometer. The sequencer 212 may be single equipment/device or a series of equipment/devices in combination configured to sequence and determine an order of the peptide sequences and/or separate peptide sequences from a mixture of peptides. Peptide sequencing is expected to be continuously performed for research purposes, as peptides are important for all living organisms. Consequently, equipment/devices and methods to retrieve digital data from digital data bearing peptides will be available. This can be advantageous over storage devices such as optical disks, in which case, once they became obsolete, it is very difficult to find the drives to retrieve data from these media, similar to the fate of obsolete Iomega Zip and floppy disks.

Figure 5:
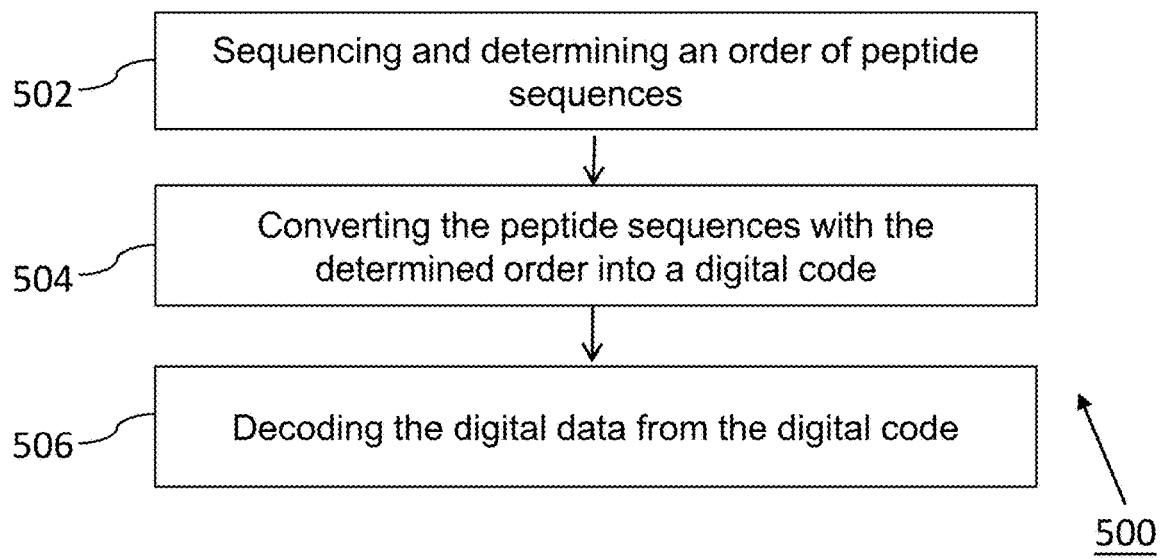
FIG. 5 depicts a flowchart illustrating a method of retrieving digital data from peptide sequences in accordance with embodiments of the disclosure.

The system 200 can be used to implement method 500 for retrieving digital data from peptide sequences as depicted in FIG. 5. The processor 202 and the memory 204 including computer program code in the system 200 can be parts of a general purpose computing device as depicted in FIG. 3, in which the processor 202 corresponds to processor 302, and the memory 204 corresponds to memory 304. The processor 202 and the memory 204 in the system 200 can be the same as or different from the processor 102 and the memory 104 used in the system 100. The method 500 broadly includes:

step 502: sequencing and determining an order of the peptide sequences;

step 504: converting the peptide sequences with the determined order into a digital code; and step 506: decoding the digital data from the digital code.

At step 502, the digital data bearing peptides are sequenced and an order of the peptide sequences is determined by the sequencer 212. The sequencing can be based on enzymatic digestion, mass spectrometry (MS), Edman Degradation, nanopore sequencing, or any combinations thereof. Sequencing comprises multiple steps including, but are not limited to, peptide separation, ionization, ion selection, fragmentation, sequencing, or any combinations thereof. In one example, individual peptides can be separated from a mixture of peptides using methods such as, but are not limited to, electrophoresis, liquid chromatography (LC), ion mobility, cationic exchange (SCX), high performance liquid chromatography (HPLC), ultrahigh pressure liquid chromatography (UPLC), nano-liquid chromatography or any combinations thereof. In yet another example, peptides can be sequenced using a mass spectrometry methods such as, but not limited to, mass spectrometry (MS), tandem mass spectrometry (MS/MS), matrix-assisted laser desorption/ionization (MALDI) spectrometry, Matrix-Assisted Laser Desorption/Ionization Time-of-Flight (MALDI-TOF) spectrometry, or any combinations thereof. In another example, peptides are converted to charged ions using ionization methods such as, but not limited to, electrospray ionization, matrix-assisted laser desorption/ionization, surface-assisted laser desorption/ionization, atmospheric-pressure ionization, direct ionization, or any combinations thereof for mass spectrometry analysis. In yet another example, peptides that are ionized can undergo ion selection using methods such as, but are not limited to, data-independent-acquisition (DIA), data-dependent-acquisition (DDA), non-targeted, targeted, or any combinations thereof, for MS/MS analysis. In another example, peptides that are ionized can be fragmented based on methods such as, but are not limited to, collision-induced dissociation (CID), high-energy collisional dissociation (HCD), electron-capture dissociation (ECD), electron-transfer dissociation (ETD), or any combinations thereof to elucidate the amino acid sequences. In certain embodiments, mass spectrometry method is selected from the group consisting of LC-MS/MS and MALDI-MS. The conditions of the sequencer 212 can optimized for separation, detection and sequencing of peptides in the mixtures. In an embodiment of the present disclosure, a LC-MS/MS protocol has been developed and successfully applied to analysis of a mixture containing 40 data-bearing 18-mer peptides, each with two fixed amino acids at the two ends.

By appropriate design of the peptides, the performance of the systems and methods described can be enhanced. For example, peptide length, peptide stability, peptide water solubility, and other parameters can be improved in accordance with the methods described herein, which can result in an increase data storage, increased storage stability, reduced processing and analysis time and the peptide sequencing costs.

In instances in which the step of sequencing and determining an order of the one or more peptide sequences comprises a mass spectroscopy method, the ionization and fragmentation properties of the peptides can be critical to successful peptide sequencing. It has been discovered, that the placement and number of basic amino acids in the peptides can be determine, in part, whether the peptide sequence can be successfully sequenced using a mass spectrometry method. The signal of the MS1 parent ion and MS2 fragment ions can be increased by careful design of the peptide. If a basic amino acid is placed at the C-terminal of the peptide it is very likely to sequester a proton at that site. Therefore after fragmentation, the charge is likely to be found in the C-terminal fragment, thus the y-ions would be much more intense than b-ions. With only clear y-ions present in the spectra, the spectra can be more straightforward to analyze resulting an increase in sequencing success rates and accuracy.

Figure 17:
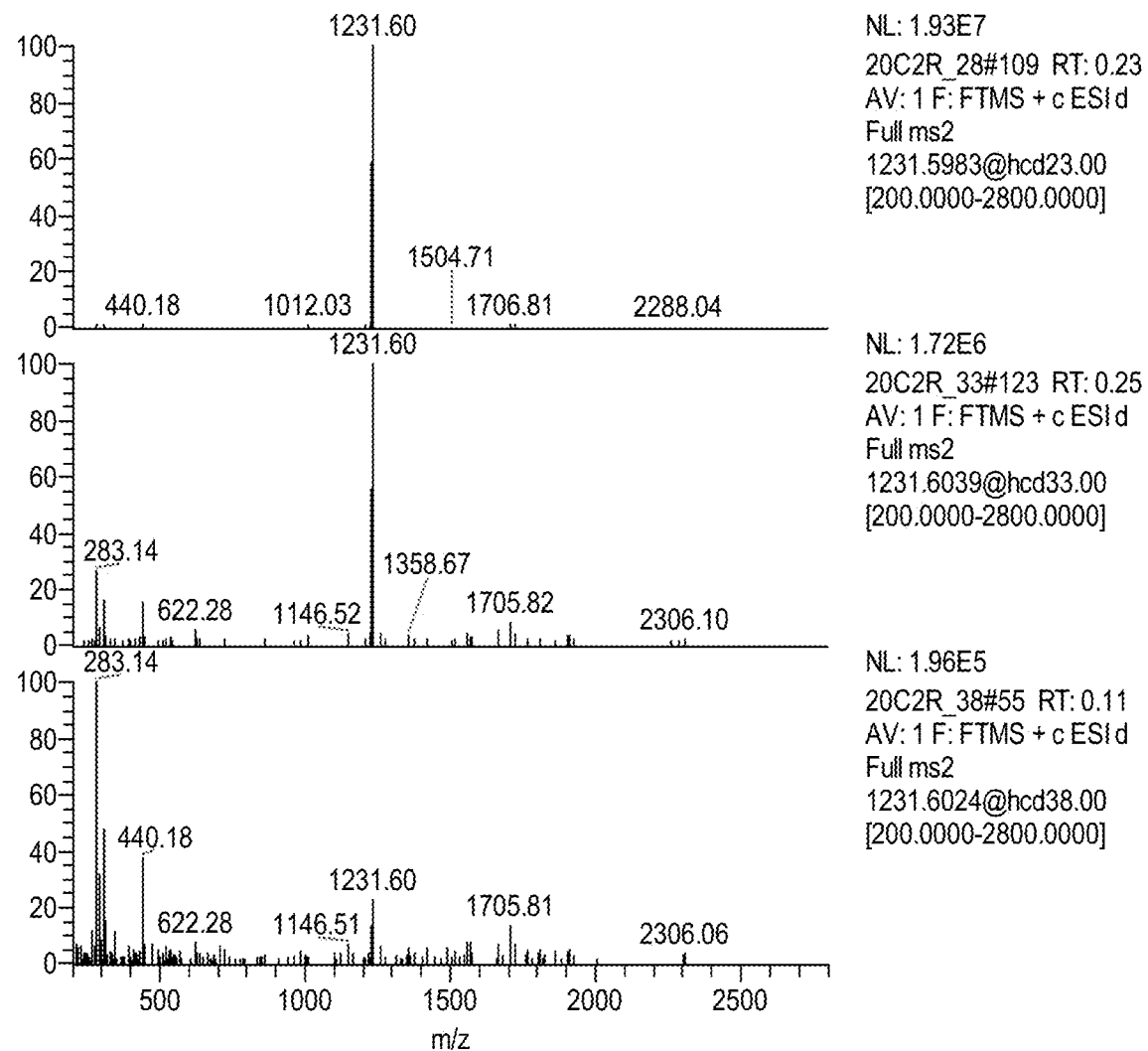
FIG. 17 depicts the MS2 spectra of the polypeptide sequence: FYEVTVFAEVLYFEYETRR (SEQ ID NO: 2) with various HCD energies.

FIG. 16 summarizes the results of peptide optimization experiments, wherein one, two, three, or four basic amino acids are positioned at the C-terminal of the polypeptide. As expected, the water solubility of the peptides increases as the number of arginine residues placed at the C-terminal increases. When subjected to tandem MS analysis, peptides with one arginine at the C-terminal (SEQ ID NO: 1 and 5) produce sufficient MS1 and MS2 fragment ions to sequence the peptide using the methods described herein. However, while peptides having more than one arginine at the C-terminal generate intense MS1 parent ions, they produce an insufficient amount of MS2 fragment ions to successfully sequence the peptide (See, e.g., SEQ ID NO: 2-4 and 6-8). FIG. 17 shows the MS2 mass spectrum of SEQ ID NO: 2 at different HCD energy levels, which includes two arginine residues at the C-terminal. At all HCD levels tested, the collected MS2 fragment ion data was insufficient to sequence the peptide sequence of SEQ ID NO: 2.

In certain embodiments, each of the peptides have no more than one basic amino acid comprising a side chain having a basic residue with a pKb less than 8, less than 7, less than 6, less than 5, less than 4, less than 3, less than 2, less than 1, or less than 0.5. In certain embodiments, each of the peptides have no more than one basic amino acid comprising a side chain having a basic residue with a pKb less than 4; and the basic amino acid comprises a side chain having a basic residue with a pKb 0.5 to 3.4, 0.5 to 3, or 0.5 to 2. In certain embodiments, each of the peptides have no more than one basic amino acid comprising a side chain having a basic residue with a pKb less than 4; the basic amino acid comprises a side chain having a basic residue with a pKb of 0.5 to 2; and the basic amino acid is located at the C-terminal of the peptide.

In certain embodiments, each of the peptides have no more than one basic amino acid located at the C-terminal of each peptide, wherein the basic amino located at the C-terminal comprises a side chain having a basic residue with a pKb less than 8, less than 7, less than 6, less than 5, less than 4, less than 3, less than 2, less than 1, or less than 0.5. In certain embodiments, the basic residue located at the C-terminal has a pKb of 0.5 to 3.4, 0.5 to 3, or 0.5 to 2. In certain embodiments, the basic residue located at the C-terminal amino acid has a pKb of 0.5 to 3.4, 0.5 to 3, or 0.5 to 2.

The basic amino acid can be any naturally occurring basic amino acid, unnatural basic amino acid, or basic amino acid analog. Exemplary basic amino acids include, but are not limited to arginine, lysine, histidine, homoarginine, norarginine, homolysine, norlysine, aminoalanine, aminoproline, guanidinoproline, amino-phenylalanine (e.g., 2-aminomethyl-phenylalanine, 3-aminomethyl-phenylalanine, 4-aminomethyl-phenylalanine, and 4-amino-phenylalanine), 6-aminohexanoic acid, aminoalkyl-phenylalanine, guanidine-phenylalanine, aminomethyl-N-alkyl-phenylalanine, pyridyl alanine (e.g., 2-pyridylalanine, 3-pyridylalanine, 4-pyridylalanine), aminomethylcyclohexyl-alanine, piperidinyl-alanine, quinolyl-alanine, 2,3-diaminopropionic acid, 2,4-diaminobutyric acid, 2,3-diaminobutyric acid, ornithine, 1,3-diaminopropane, 1,2-diaminopropane, 1,2-diaminoethane, α-(2-pyridinylmethyl)-proline, α-(3-pyridinylmethyl)-proline, α-(4-pyridinylmethyl)-proline, γ-(2-pyridinylmethyl)-proline, γ-(3-pyridinylmethyl)-proline, γ-(4-pyridinylmethyl)-proline, and analogs thereof; or a basic amino acid analog having the formula: $(R^1)_2N(CR^2{}_2)_m N(R^3)_2$, wherein m is a whole number selected from 2-6, 2-5, 2-4, or 2-3; $R^1$ for each occurrence is independently hydrogen or alkyl; $R^2$ for each occurrence is independently hydrogen or alkyl; and $R^3$ for each occurrence is independently hydrogen or alkyl. Exemplary basic amino acid analogs include, but are not limited to 1,3-diaminopropane, 1,2-diaminopropane and 1,2-diaminoethane. In certain embodiments, each of the peptides can have no more than one basic amino acid at the C-terminal selected from the group consisting of arginine, 1,2-diaminopropane and 1,3-diaminopropane.

Advantageously, if a basic amino acid, such as arginine, is positioned at the C-terminal of the peptide, the peptide can also be successfully sequenced using MALDI-MS instead of LC-MS/MS. FIGS. 21A and 21B depict the mass spectra of SEQ ID NO: 12 and 13, which permits direct solid state sequencing the peptides described herein. Solid state sequencing of the peptides reduces processing and analysis time and the cost of sequencing the peptides.

Figure 20:
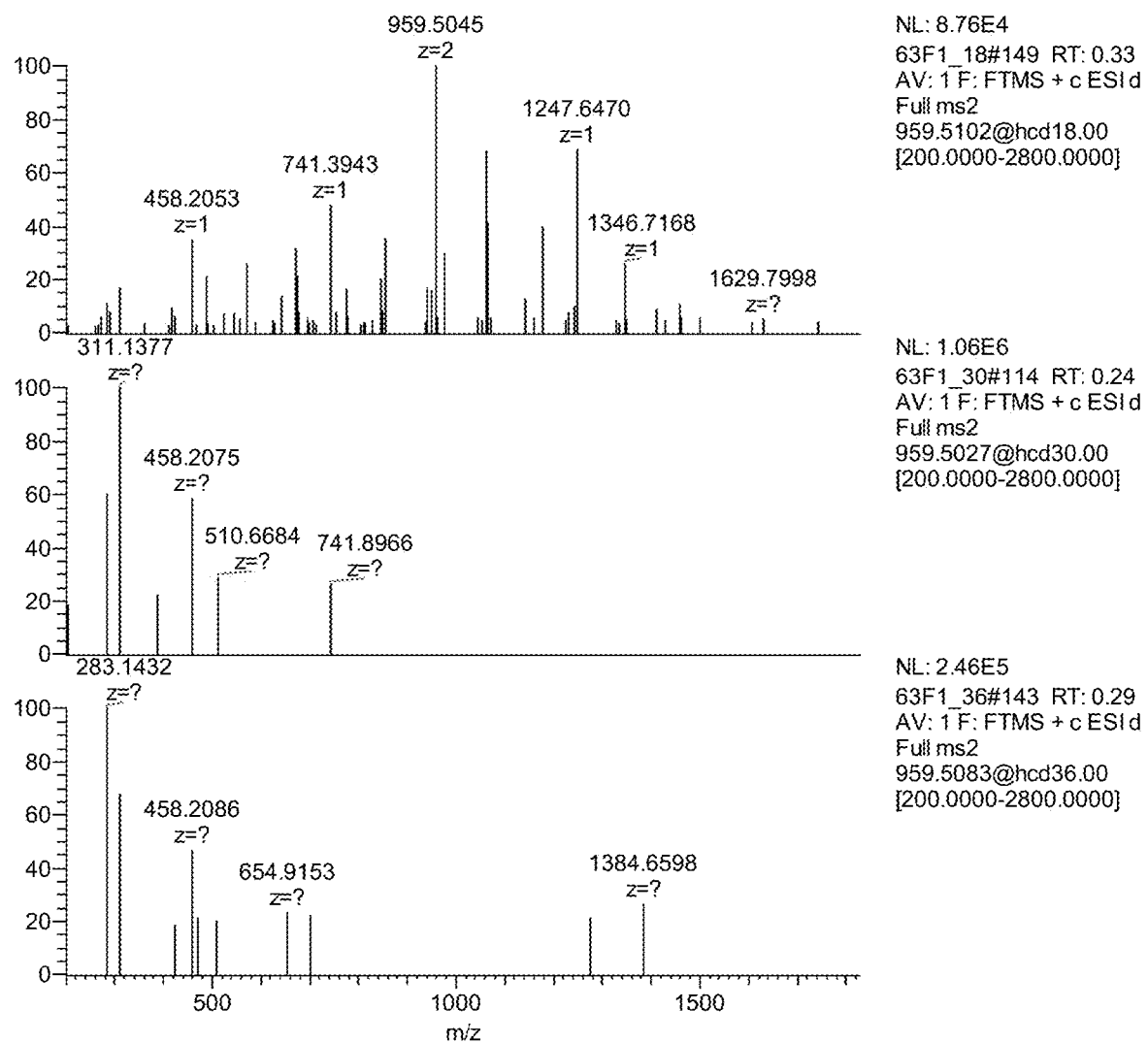
FIG. 20 depicts the MS2 spectra of the polypeptide sequence: FYFLVALSEATSVAELA{dap} (SEQ ID NO.

In instances in which 1,3-diaminopropane is positioned at the C-terminal of the peptide, lower HCD energy can be used to sequence the peptide using a mass spectrometry method. FIG. 20 shows ion fragments that were produced from mass spectrometry analysis of SEQ ID NO: 11 at different HCD levels. The number of ion fragments were sufficient to correctly sequence SEQ ID NO: 11.

Placement of a basic amino acid in the internal amino acid sequence may result in poor MS2 ion fragmentation, which can cause peptide sequencing failure and a loss in data retrieval. Accordingly, in certain embodiments, each of the peptides do not contain a basic amino acid in the internal amino acid sequence. In certain embodiments, each of the peptides do not contain a basic amino acid having a side chain comprising a basic residue having a pKb less than 8, less than 7, less than 6, less than 5, less than 4, less than 3 in the internal amino acid sequence. In certain embodiments, each of the peptides do not contain a basic amino acid having a side chain comprising a basic residue having a pKb less than 8, less than 7, or less than 6.

Figure 18:
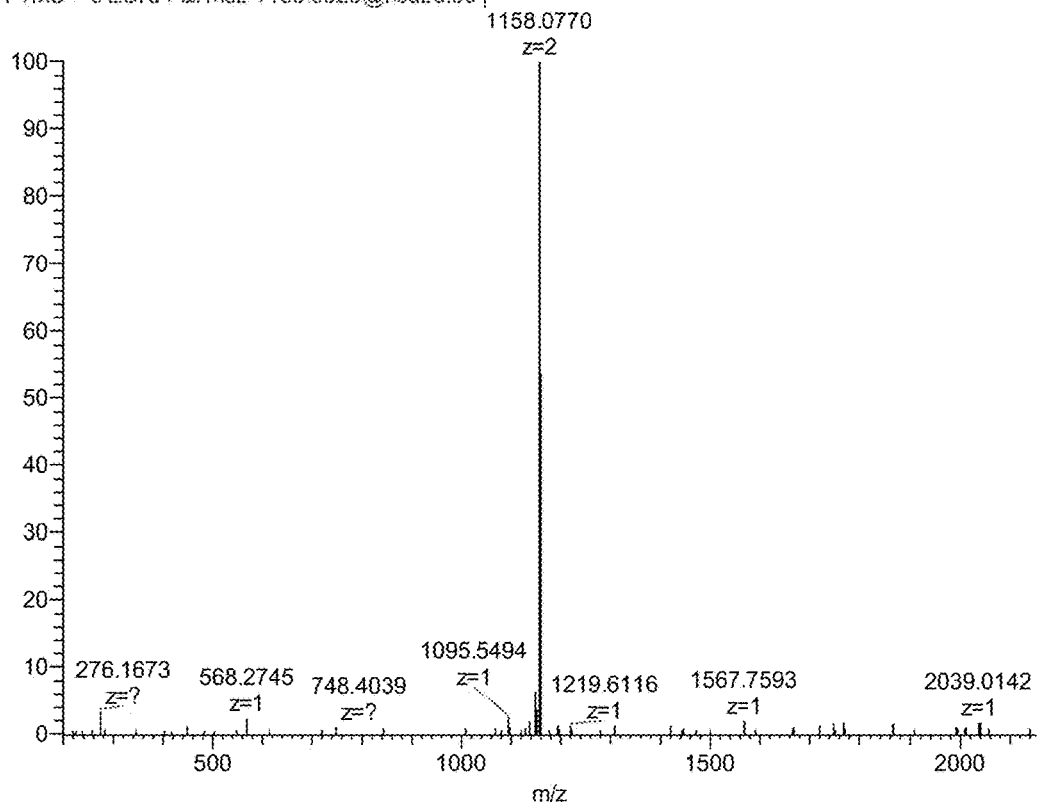
FIG. 18 depicts the MS2 spectrum of the polypeptide sequence: RYEVTVFAEVLYFEYETR (SEQ ID NO: 9).

FIG. 18 depicts the MS2 spectrum of exemplary peptide SEQ ID NO: 9 having arginine at both the C-terminal and the N-terminal. As shown in FIG. 18, placement of strongly basic amino acids, such as arginine, at both the N-terminal of the peptide may also result in poor MS2 ion fragmentation, which may result in peptide sequencing failure. Accordingly, in certain embodiments, each of the peptides do not contain a strongly basic amino acid having a side chain comprising a basic residue having a pKb less than 3, less than 2, less than 1, or less than 0.5 at the N-terminal. In certain embodiments, each of the peptides do not contain an arginine at the N-terminal.

The water solubility of the peptides can be improved by the incorporation of one or more hydrophilic amino acids. Preferably, the peptides are at least partially soluble in water, as water is less toxic than organic solvents, and organic solvents (e.g., DMSO or acetonitrile) may cause peak broadening in liquid chromatography (LC), which can result in poor peptide separation during LC and consequently the potential for poorer separation of similar peptides.

Hydrophilic amino acids that can be placed in the internal amino acid sequence include those amino acids that include hydrophilic side chains. Hydrophilic amino acids may include amino acids having Wimley-White whole-residue hydrophobicity interface scale $\Delta G$ (water to octanol) between −2 to 0.6 kcal/mol. Exemplary hydrophilic amino acids include, but are not limited to aspartic acid, serine, homoserine, threonine, homothreonine, β-homothreonine, glutamic acid, hydroxyproline, hydroxyleucine, hydroxyisoleucine, hydroxyalanine, and the like. In order to enhance water solubility, hydrophilic amino acids may be in placed in the internal amino acid sequence together with other amino acids, such as alanine, glycine, leucine, isoleucine, valine, and the like.

Water solubility of the peptides can be further improved by excluding or limiting the proportion of highly hydrophobic amino acids, such as phenylalanine, tryptophan, and optionally tyrosine, from the internal sequence. Accordingly, in certain embodiments, the internal amino acid sequence of each of the peptides include no more than 2, no more than 1, or zero highly hydrophobic peptides selected from the group consisting of phenylalanine, tryptophan, and optionally tyrosine.

Hydrophilic amino acids, such as serine, threonine, aspartic acid, glutamic, and weakly basic amino acids, such as histidine and lysine, may also be placed at the N-terminal (in place of the N-terminal phenylalanine) to improve the solubility of the peptide.

The water solubility of the peptides can be further improved by conjugation of polyethylene glycol (PEG) or Me-PEG to the peptide. The PEG may be attached using conventional synthetic methods at the N-terminal amine, C-terminal carboxylic acid, or on a side chain containing the appropriate functionality.

The inclusion of certain amino acids in the peptides may result in increased decomposition of the peptides during storage. For example, the incorporation of amino acids that are prone to oxidation during storage may decrease the stability of the peptides of storage. The formation of impurities can result in the loss of data stored in the peptides and/or increase complications during peptide sequencing. For example, cysteine, tryptophan, and methionine are known to be prone to oxidative decomposition e.g., by reaction with oxygen to form e.g., disulfide, quinone, and $RSO_x$ oxidation products. Accordingly, in certain embodiments, the peptides do not include one or more amino acids selected from the group consisting of cysteine, tryptophan, and methionine.

Certain amino acids may lead to complications during peptide sequencing using a mass spectrometry method due, e.g., highly favored fragmentation patterns that may result in additional MS1 parent and/or MS2 fragment ion peaks that interfere mass spectra analysis and sequencing. For example, glutamine and asparagine are known to readily lose amine during fragmentation, which results in a −17 Da peak, which can lead to mass spectra analysis complications. Accordingly, in certain embodiments, the peptides do not include one or more amino acids selected from the group consisting of glutamine and asparagine.

Figure 19A:
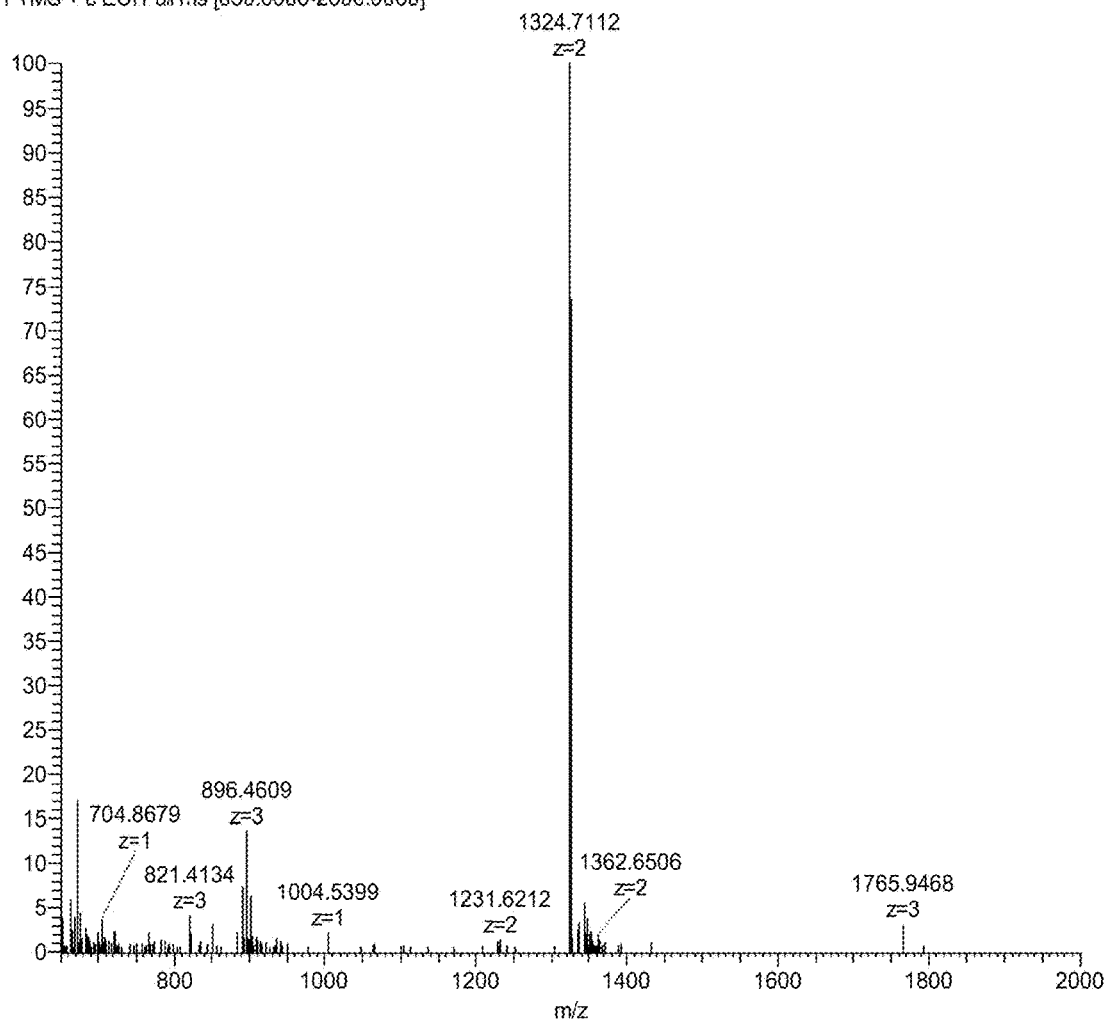
FIG. 19A depicts the MS1 spectrum of the polypeptide sequence: FYFLVALSEATSVAVTLFEAELAR (SEQ ID NO: 10).
Figure 19B:
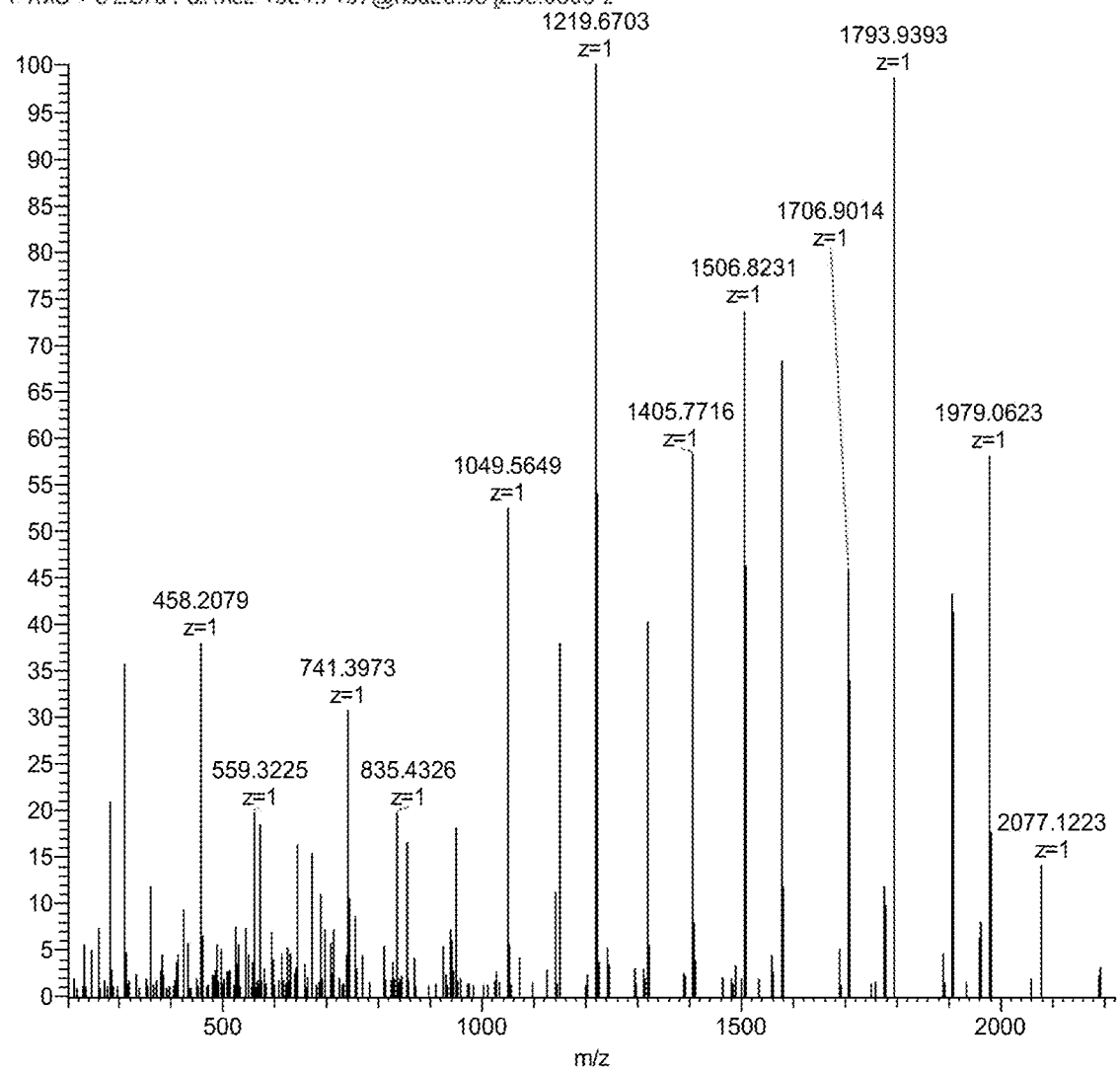
FIG. 19B depicts the MS2 spectrum of the polypeptide sequence: FYFLVALSEATSVAVTLFEAELAR (SEQ ID NO: 10).

The improvements to the design of the peptides described herein enable the use of longer peptides and even mixtures of different peptide lengths. In certain embodiments, the peptides can range from 16-30, 16-28, 16-24, and combinations thereof. FIGS. 19A and 19B show the MS1 and MS2 spectra of an exemplary 24 mer peptide (SEQ ID NO: 10) in accordance with certain embodiments described herein, which provides sufficient ion fragmentation information to successfully sequence the peptide. Longer peptides can hold more information and can reduce the addressing and error-correction overhead.

Analysis of the peptide sequence can be accomplished by methods including, but not limited to, database search or de novo sequencing. "Database search" refers to a simple version wherein the mass spectral data of the unknown peptide is submitted and checked against the mass spectral data in the database to find a match with a known peptide sequence, with the drawback that database searching cannot identify novel proteins and modified proteins which are not contained in the database. For digital data storage, the peptides are used to carry random information bits with "0"s and "1" s. The peptides are therefore unnatural peptides and no database is available for searching and identifying these peptides. In contrast to database search method, de novo sequencing method expands the search space to all combinations of the amino acids.

"De novo sequencing" refers to the process of assigning fragment ions directly from a mass spectrum, wherein different parameters and algorithms can be selected and used for interpretation, without referring to established databases. As such, the determination of the peptide sequence requires a computational method that is able to utilize the readout generated by the sequencing step, for example from a mass spectrum, and to identify the order of the amino acids based on the sequencing method disclosed herein. A number of algorithms have been developed by use of the graph theory model together with the dynamic programming algorithms, including, but are not limited to, Lutefisk, Sherenga algorithm, PepNovo, MSNovo, pNovo, UniNovo, NovoHCD, and Novor.

A constraint for the dynamic algorithm is that no training spectra are provided for the sequencing of the digital data bearing peptides. Accordingly, de novo sequencing based on the graph model is utilized for determining the peptide sequences. In the graph model, the MS/MS spectrum is represented by a directed acyclic graph (DAG), called spectrum graph. The peaks of the spectrum can be taken as vertices, while an edge is added between two vertices when the mass gap between two peaks is equal to the mass of an amino acid. The objective of the dynamic programming is to find the longest path (or best path) in the graph starting from the head vertex to the tail vertex. An alternative approach to identify the sequence is to start with the middle part of the MS/MS spectrum. For example, the sequence tagging method first infers a partial sequence called tag, and then finds the whole sequence that can match the tag. In the tag-based method, the tags are first found from the MS/MS spectrum based on some scoring schemes. The inference of the sequence then relies on peptide comparison using the database search method or on extending the valid path of the tag in the middle position of the path using the de novo sequencing.

The peptide sequencing problem is outlined in Table 4, with knowledge of the information of the amino acids used, the spectrum S, the mass of the whole sequence, and the head and tail amino acids. The sequencing problem is to find the peptide P, whose theoretical spectrum T(P) best matches the experimental spectrum S. In some embodiments, it is assumed that the length N of the peptide sequence is fixed and known. Thus, the candidate peptides without length N are discarded. Two sequencing methods, namely two-stage sequencing method and highest-intensity-tag based sequencing method, are proposed. For both methods, the sequences are estimated in a manner that first infers a partial sequence with a small amount of reliable information and then finds the missing part of the sequence with less reliable data or the raw data. The purpose is to improve the speed of sequencing by generating fewer candidates. Moreover, due to the introduction of the tag, the highest-intensity-tag based sequencing method is more effective in rejecting the unlikely candidates.

TABLE 4

Description of the peptide sequencing problem.

| | Peptide sequencing problem |
|---|---|
| Input: | set A of amino acids; |
| | mass set g for the amino acids in set A; |
| | experimental spectrum S; |
| | set (m/z) of mass/charge ratio of spectrum S; |
| | set I of intensity of spectrum S; |
| | length N of the peptide sequence; |
| | head and tail amino acids used for the peptide; |
| | mass M of the whole sequence. |
| Output: | Peptide P of length N. |
| Problem: | find peptide P, which most likely generates the experimental spectrum S. |

Peptide Sequencing: Two-Stage Sequencing Method

Figure 12:
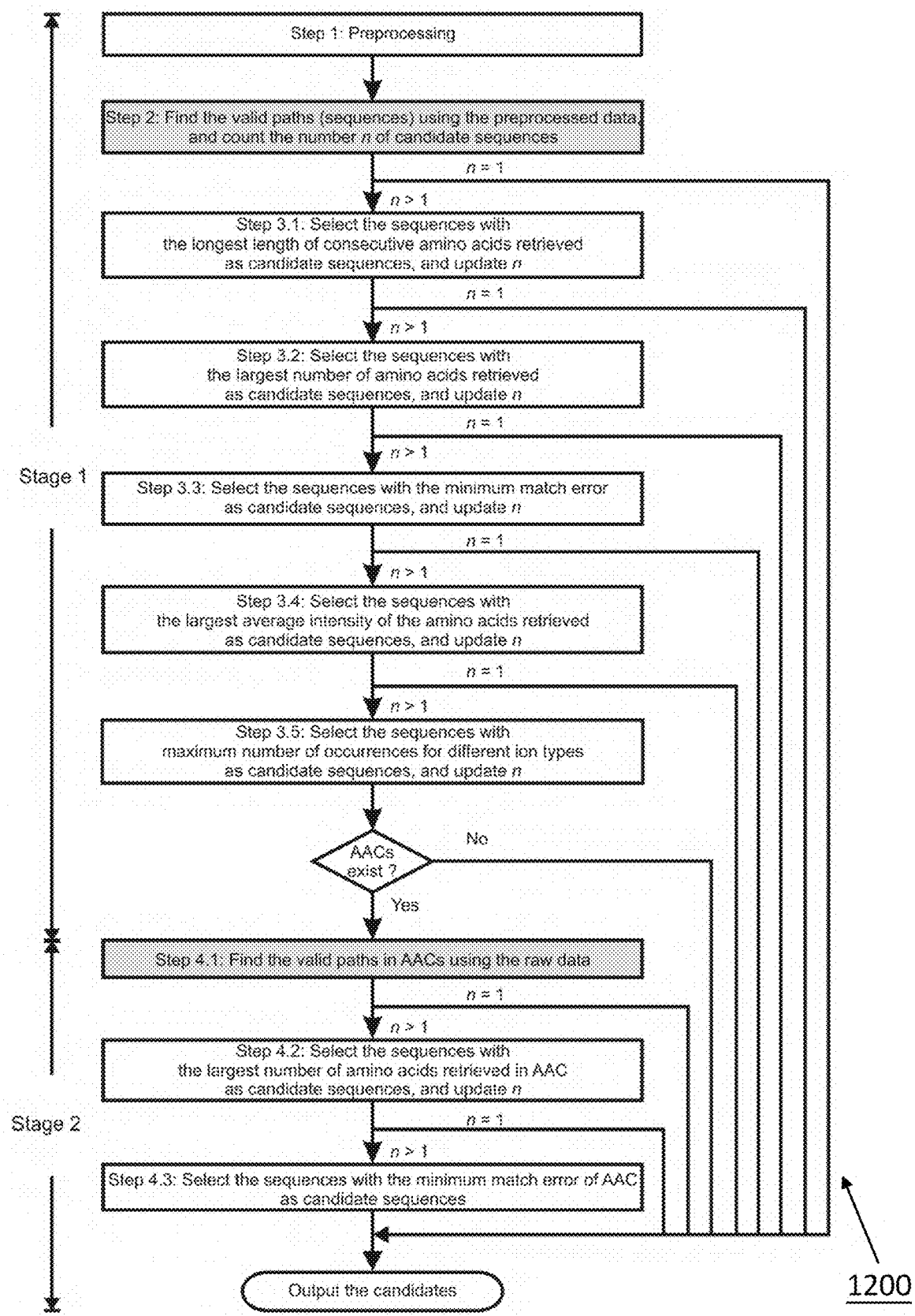
FIG. 12 depicts a flowchart illustrating a method of two-stage sequencing in accordance with embodiments of the disclosure.

FIG. 12 shows a flowchart illustrating a method 1200 of two-stage sequencing. Four steps are involved in the two-stage sequencing method 1200: (1) preprocessing, (2) candidate sequence generation, (3) sequence selection, and (4) candidate refining. As shown in FIG. 12, Steps 1-3 belong to the first stage (Stage 1), while Step 4 is processed in the second stage (Stage 2). In Stage 1 of the two-stage sequencing method 1200, partial sequence is inferred using the preprocessed data after Step 1. In Stage 2, the remaining part of the sequence is determined using the raw data.

At Step 1, preprocessing is performed. The goal of the preprocessing is twofold. Firstly, the goal is to remove some uninterpretable masses caused by noise and uncertainty. Secondly, the goal is to convert the mass/charge ratio set (m/z) to the corresponding mass sets $m'_b$ and $m'_y$. Given a set of mass/charge (m/z) ratios, these ratios are grouped into p subsets $G_1, G_2, \ldots, G_p$, where in each subset $G_i$, $i=1, 2, \ldots, \rho$, all (m/z) ratios are isotopes of a particular fragment, with a charge of value 1, 2, or 3 equaling the inverse of difference between consecutive (m/z) ratios in this subset. For each subset $G_i$, a monoisotopic mass $m'_i$ is calculated by $m'_i=(m/z)_{i,0} z'_{i,0}-m_H z'_{i,0}$, $i=1, 2, \ldots, \rho$, where $(m/z)_{i,0}$ is the lowest value in this subset, and $z'_{i,0}$ is the corresponding charge for $(m/z)_{i,0}$. These $m'_i$ values are then distributed among the mass sets $m'_b$ and $m'_y$. In some embodiments, one of the criteria of distribution is based on the intensities corresponding to the $m'_i$ values. In some embodiments, one of the criteria of distribution is the isotopic pattern of the (m/z) ratios in G. In some embodiments, one of the criteria of distribution is based on the fact that if $m'_i$ is in $m'_{b,j}$, then there is a corresponding $m'_j$ in $m'_{y,j}$, where $m'_j=M-m'_i$. In some embodiments, the distribution is determined real-time in Step 2 as described later in paragraphs [0114]-[0115]. In some embodiments of the preprocessing, only those with typical property of charges are reserved as the preprocessed data such that the preprocessed data may be more reliable than the raw data. However, in the event of the incomplete or ambiguous data (e.g., data lacking charge property), some useful mass values may be discarded in the preprocessing based on the abovementioned criteria. Hence, in the case when missing/uncertain elements of the sequence exist in Stage 1, the raw data may be considered in Stage 2.

Figure 13:
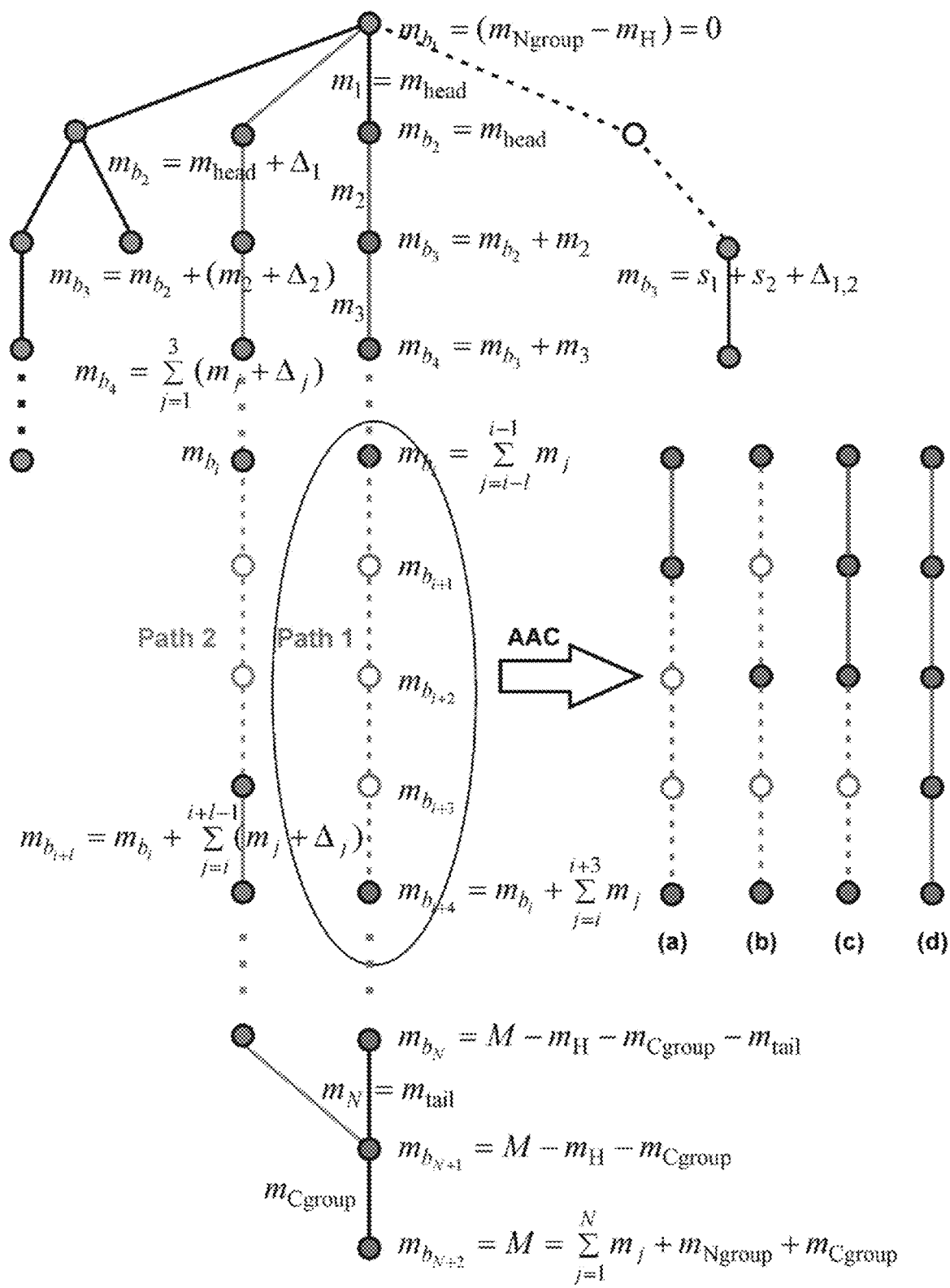
FIG. 13 depicts an illustration of path finding in graph theory model in accordance with embodiments of the disclosure.

At Step 2, the preprocessed data from step 1 is used to find the valid paths (sequences), and the number n of candidate sequences is counted. In FIG. 13, suppose that $m_{Ngroup}=m_H$ and $M_{Cgroup}=m_{OH}$. The graph theory model is used to find the candidate paths (valid paths) which start with head mass $m_{head}$ and end with mass $M-m_H-m_{Cgroup}-m_{tail}$ in a directed acyclic graph (DAG). Since the masses obtained by mass/charge ratio set (m/z) are likely created by b-ion, y-ion, or both b-ion and y-ion. The mass set $m'_{b,i}$, $m'_{y,i}$, or both sets $m'_{b,i}$ and $m'_{y,i}$ can be considered in the path finding algorithm. In the graph model, the mass of the fragment ion can be represented by a vertex. If the mass gap between two fragment ions equals the mass of any amino acid, then an edge is added between these two vertices. As shown in FIG. 13, the tree can be expanded edge by edge. If the set of vertices is complete for the correct path, the sequencing problem can be reduced to finding the longest path in the graph. The path should include both the head and the tail vertices. Moreover, only those paths ending with mass M are taken as the candidates. For the example shown in FIG. 13, only Path 1 and Path 2 are the candidate paths.

Due to the imperfect fragmentation in MS/MS characterizations, two and three missing ions are often observed in a sequence. In the model disclosed herein, in order to ensure that the paths from the head can be extended to the tail, the number of missing amino acids is considered to be up to 4 in Stage 1. Starting from the mass with $m_{b,1}=0$, firstly, attempt is made to find the mass of the head amino acid, $m_{b,2}=m_{head}+\Delta_1$. Next, the mass $m_{b,i+1}$ is found by using the preprocessed data such that the mass gap between the current and the next vertices is approximate to mass $s_i$ or mass summation $$\sum_{v=i}^{i+l-1} s_v (l \leq 4)$$

of up to 4 amino acids with mass $s_v \in g$ (v=1, 2, ..., N), i.e., $m_{b,i+1}=m_{b,i}+(s_i+\Delta_i)$ for two consecutive vertices i and (i+1), or $$m_{b,i+l} = m_{b,i} + \left( \sum_{v=i}^{i+l-1} s_v + \Delta_{i,i+l} \right)$$

(where $\Delta_{i,i+l} \in [-l\delta, +l\delta]$ for a length-l tag from Vertex i to Vertex (i+1). As shown in FIG. 13, suppose that Path 2 is the correct path but with experimental masses, $m_{b,1}=0$, $m_{b,i+1}=m_{b,i}+(m_t+\Delta_i)$ for two consecutive $$m_{b,i+l} = m_{b,i} + \sum_{j=i}^{i+l-1} (m_j + \Delta_j)$$

for a length-l tag. If Path 1 is the correct path with theoretical masses, then $m_{b,i+1}=m_{b,i}+m_i$ with $m_{b,1}=(m_{Ngroup}-m_H)$, $m_{b,2}=(m_{Ngroup}-m_H)+m_{head}, \ldots, m_{b,N}=M-m_H-m_{Cgroup}-m_{tail}$, $m_{b,N+1}=M-m_H-m_{Cgroup}$, $m_{b,N+2}=M$. Referring to FIG. 13, if the mass gap between two vertices equals the mass of an amino acid, then a solid edge is added. On the other hand, if the mass gap equals the mass summation of two or more amino acids, then the dashed edges are added with hollow circles representing the missing vertices.

At Step 3, the effects of the following five factors are jointly considered when arriving at the score of a sequence candidate from Step 3.1 to Step 3.5: length of consecutive amino acids retrieved, number of amino acids retrieved, match error, average intensity of amino acids retrieved, and number of occurrences for different ion types with different offsets. The sequences with the longest length of consecutive amino acids retrieved are first selected (Step 3.1). Among the selected sequences, the sequences with the largest number of amino acids retrieved are then selected (Step 3.2). For the sequences with equal length of consecutive amino acids retrieved together with equal number of amino acids retrieved, the match error is evaluated, which is the mean square error between the observed mass values for the amino acids retrieved from the experimental spectrum and the actual mass values of the amino acids (Step 3.3). If there is more than one sequence with identical match errors, the average intensity of amino acids retrieved is further calculated and a higher score is given to a sequence with a larger average intensity value (Step 3.4). In addition, multiple ion types are usually considered as the important factors in inferring an amino acid, which means that a mass value may correspond to different types of ions in the spectrum. Generally, the more the number of occurrences for different ion-types of an amino acid is, the more likely the amino acid is correct. Therefore, for the sequences with equal score after the aforementioned evaluations of Steps 3.1-3.4, the number of occurrences for different ion-types is counted to determine the sequence (Step 3.5). The mass offset sets for the N-terminal a-ion, b-ion and c-ion type sets, i.e., $\{a, a-H_2O, a-NH_3, a-NH_3-H_2O\}$, $\{b, b-H_2O, b-H_2O-H_2O, b-NH_3, b-NH_3\pm H_2O\}$, and $\{c, c-H_2O, c-H_2O-H_2O, c-NH_3, c-NH_3-H_2O\}$ are $\{-27, -45, -44, -62\}$, $\{+1, -17, -35, -16, -34\}$, and $\{+18, 0, -18, +1, -17\}$, respectively. The mass offset sets for the C-terminal x-ion and y-ion type sets can be calculated by shifting the masses of the c-ion and b-ion type sets by +27 and +18, respectively. According to the fragmentation method and the property of the data, all or some of the above ion types can be used flexibly.

Since the candidate sequences obtained at Step 2 are found by using the preprocessed data, which aim to provide more reliable information to generate the partial sequence, amino acid combinations (AACs) may present in the sequence due to insufficient data provided by preprocessing. At Step 4, if selected sequences with missing mass values exist, which means that the corresponding mass gaps are equal to the summation of at least two amino acids, the raw data may be used to find as many vertices as possible for the path in Stage 2. For the raw data, suppose that all (m/z) ratios have opportunity to be created by the singly, doubly or triply charged ions. Then the set with q mass/charge ratios $(m/z)_i$ ($i=1, 2, \ldots, q$) can be converted to the mass set $m'_b$ of putative b-ion and the equivalent b-ion mass set $m'_y$ of putative y-ion, each of sets $m'_b$ and $m'_y$ has 3q elements. Although the number of mass values increases, only the range between the head mass and the tail mass of the AAC is considered, which is relatively smaller when compared to that for the whole sequence. As shown in FIG. 13, a gap being the mass summation of 4 amino acids is shown in Path 1. With more information provided by the raw data, the following cases can be found for the gap: (a) composition of amino acid and AAC, (b) composition of two AACs, (c) composition of tag and AAC, and (d) one tag. Note that a gap being the mass summation of more amino acids is effective to ensure that the valid paths can be formed. However, more candidate sequences may be generated and thus longer time is required for the sequencing.

As shown in FIG. 12, after finding the missing amino acids of AACs at Step 4.1, the sequences with the longest length of consecutive amino acids retrieved in AACs are selected as candidate sequences (Step 4.2). If there still remain at least two candidate sequences after selection, a final decision is made based on the match error of the amino acids retrieved in AACs for each sequence (Step 4.3).

Peptide Sequencing: Highest-Intensity-Tag Based Sequencing Method

The mass/charge (m/z) ratio corresponding to the first or second highest intensity is first recognized to further infer the tag or the path. In highest-intensity-tag based sequencing method, short tags with three amino acids are used in the tag-based methods, such as GutenTag, DirecTag, and NovoHCD. Although tags with shorter length can avoid introducing the wrong amino acids, the number of candidate tags is relatively larger and sometimes it is hard to infer the sequences due to insufficient information provided by the tag. As disclosed herein, the length of the tag is not fixed and can be up to the length of the peptide if the data is complete, which helps to reduce the search space. When a tag contains wrong amino acids, usually, it cannot be extended with valid prefix and suffix parts. In this case, the length of the tag is shortened by adaptively reducing the number of the higher-intensity data points used for the tag-finding algorithm. In addition, the vertex with the highest intensity may not definitely present in the correct path due to the uncertainty of the data. When valid paths cannot be found, it may be possible to infer the tag with the second highest intensity.

Figure 14:
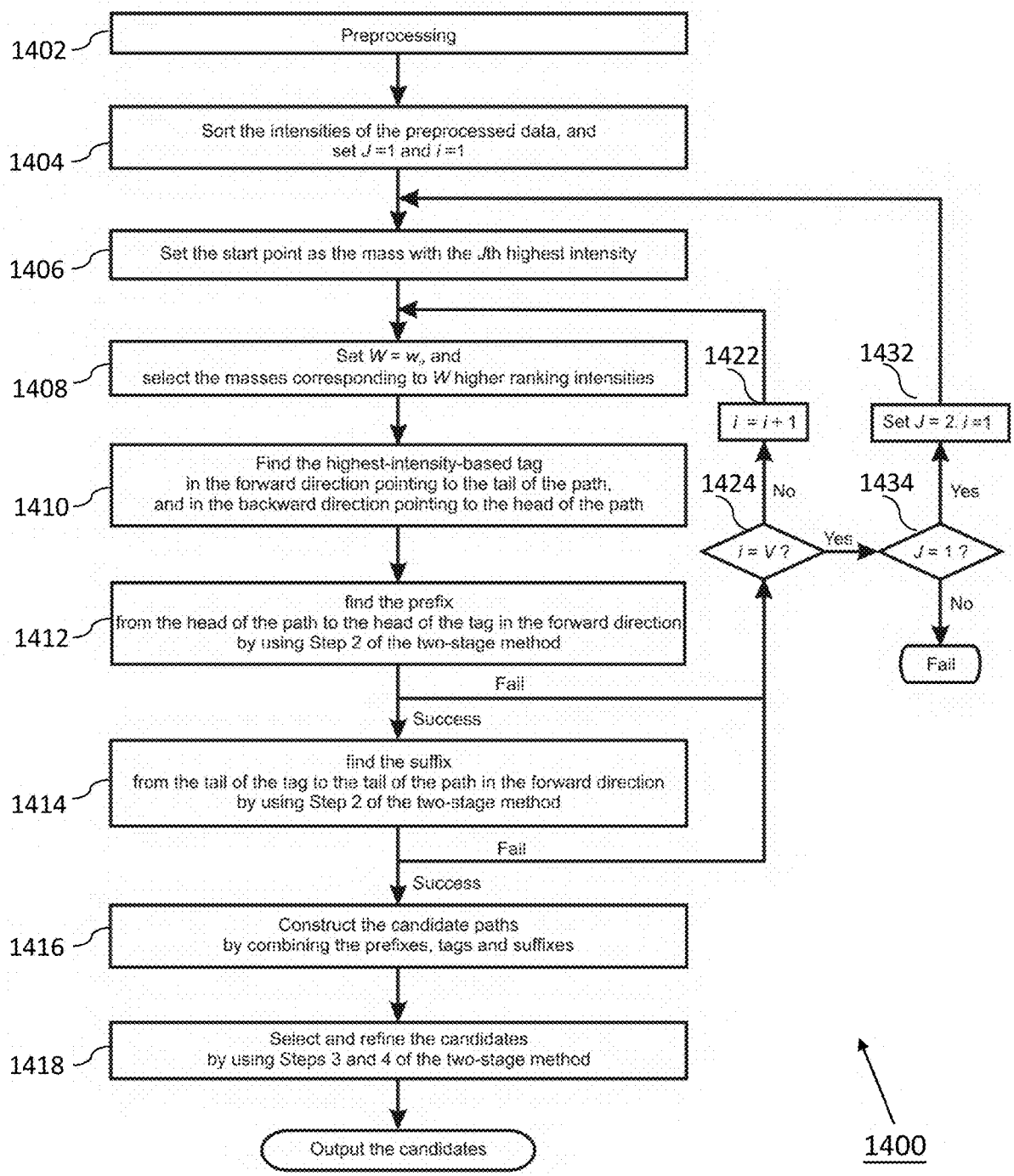
FIG. 14 depicts a flowchart illustrating a method of highest-intensity-tag based sequencing in accordance with embodiments of the disclosure.

FIG. 14 shows a flowchart illustrating a method 1400 of highest-intensity-tag based sequencing. The method 1400 commences at step 1402 for preprocessing of the raw data. Step 1402 is the same as step 1 of the two-stage sequencing method 1200. The method 1400 then proceeds from step 1402 to steps 1404, 1406, and 1408.

At steps 1404, 1406 and 1408, the intensities of the preprocessed data are sorted from the largest to the smallest and values with J denoting the ranking of intensity. The mass/charge ratio with the highest intensity is then identified and the mass/charge ratio is converted to the corresponding mass of a b-ion. As a start, it is set as J=1 and i=1, and using only $W=w_i$ ($N \geq w_1 > w_2 > \ldots > w_V$) masses with the higher ranking in the tag-finding processing.

Figure 15:
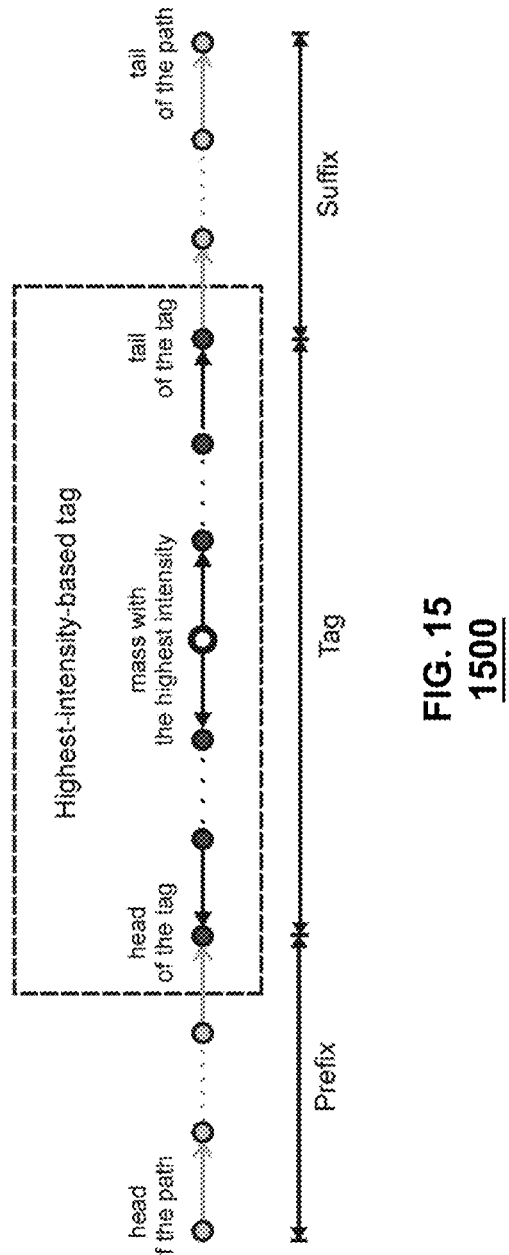
FIG. 15 depicts an illustration of highest-intensity-tag based sequencing method in accordance with embodiments of the disclosure.

The method 1400 then proceeds to step 1410 to find the highest-intensity-based tag. Starting from the mass $m'_{B,J}$ of the b-ion or $m'_{Y,J}$ of the y-ion with the highest intensity, the highest-intensity-based tag is found by simultaneously connecting the vertices in the forward direction pointing to the tail vertex of the path, and connecting the vertices in the backward direction pointing to the head vertex of the path, where the vertices have mass gap being the mass $g_k$ ($k=1, 2, \ldots, K$) of any amino acid and preferably the length of the tag is as long as possible (see FIG. 15). The tags containing the amino acid with the highest intensity are obtained subsequently, which are called highest-intensity-based tags. With knowledge of the masses of the head and the tail amino acids of a highest-intensity-based tag, the method proceeds to step 1412 to find the prefixes that can connect the head of the path to the head of the tags in the forward direction by using the method described at Step 2 of the two-stage sequencing method 1200. For the tags with valid prefixes, at step 1414, the suffix parts of the sequences can be further found by linking the tail of the tags to the tail of the path in the forward direction using the similar method.

At step 1416, the candidate paths can be constructed by combining the three parts: prefix, tag, and suffix. At step 1418, one can follow Steps 3 and 4 of the two-stage sequencing method 1200 to select and refine the sequences. Note that a larger value for W sometimes introduces one or more wrong amino acids in the head and/or tail parts of a tag, while a smaller value for W may give more reliable tag but the length of the tag may be limited. Therefore, at steps 1422 and 1424, if no valid candidate can be found, one may attempt to reduce the value of W with $W=w_i$ by increasing i by 1, i.e., i=i+1, and repeat the tag-prefix-suffix finding procedure until the candidate sequence can be found or i=V.

At steps 1432 and 1434, for the special case when the experimental mass with the highest intensity gives an unreliable message due to noise and uncertainty, a highest-intensity-based tag or a valid path with the highest-intensity-based tag cannot be found. In this case, the mass with the second highest intensity is used by setting J=2 and i=1 to find the second highest-intensity-based tag and the candidates.

The computational method for the rapid and correct assignment of peptide sequences from the large number of MS/MS spectra presented in this disclosure has the following features: (i) assigning the peptide sequences based on the length, amino acids and sequence format that are determined at step 502; (ii) following the general rules of fragmentation of peptide ions for the sequence assignment; (iii) distinguishing isotope labels, so that if such labels, e.g. chlorine or bromine, are incorporated in the peptides, the method could identify the isotopic pattern and assign the correct ion type; and (iv) assigning the gaps when some of the b or y ion peaks in the MS/MS spectra are of low abundances or missing. In an embodiment, the method implemented in a software is developed. The method gives scores to sequence candidates based on the following five factors: the length of consecutive amino acids retrieved, the number of amino acids retrieved, match error, intensity, and the number of occurrences for different ion types with difference offsets. The higher the score is, the more likely that the sequence is correct. The computational method implemented in the software can be further optimized for better and faster sequence assignment.

Sequence Grouping

Referring to the example in FIG. 8, a mixture of peptides are synthesized from 40 peptide sequences. In one embodiment, a set of 90 spectra is obtained for the 40 peptide sequences after MS/MS analysis, each with different mass M of the whole sequences. If the data is sufficient for estimating the peptide sequences, one or more candidate sequences for each spectrum can be obtained using the peptide sequencing methods 1200 and/or 1400. Moreover, there are about 2 spectra per peptide sequence on average after ignoring the failed spectra, which means that two or more candidate sequences may correspond to one address pair. Thus, it is necessary to further select only one sequence for each address pair, which can involve the steps of: (1) finding and selecting the sequences based on Steps 1-3, 4.1-4.3 of the two-stage sequencing method 1200; (2) checking the length of the candidate sequences and discarding those without length of (N−2); (3) for the remaining candidate sequences, checking the order of Symbols $S_1$ and $S_2$, and the order of Symbols $S_{15}$ and $S_{16}$ according to the first bits of Symbols $S_3$ and $S_7$, respectively; and (4) removing the duplicate candidate sequences in each spectrum.

As a result, a set of candidate sequences regardless of the generating spectra can be obtained. The candidate sequences are then grouped according to 40 address pairs $\{A_{i,1}, A_{i,2}\}$, i=1, 2, . . . , 40. For each group, there are following cases possible:

Case 1: There is only one sequence.
Case 2: There are two or more sequences, some of which are the same, where:
2a. there is only one result with two or more sequences; or
2b. there are at least two different results, each with two or more sequences.
Case 3: All sequences in the group are different, where:
3a. different sequences belong to the same spectrum; or
3b. different sequences belong to two spectra; or
3c. different sequences belong to more than two spectra.

For Case 1, the only sequence can be assigned for the group. For Case 2a, the result with two or more sequences is selected. For Case 2b, the results with two or more sequences can be selected as candidate sequences. Among the candidate sequences, the sequence with the highest score according to Steps 3.1-3.5, 4.2, and 4.3 of method 1200 can be further selected. For Case 3a, the sequence with the highest score according to Steps 4.2 and 4.3 of method 1200 can be selected. For Case 3b, the sequences obtained by Steps 3.1, 3.2, and 4.1 of method 1200 are examined for duplicate sequences. If there are duplicate sequences, the output is the result with duplicate sequences. If not, the sequence with the highest score according to Steps 3.1-3.5, 4.2, and 4.3 of method 1200 is selected. For Case 3c, the sequence with the highest score according to Steps 3.1-3.5, 4.2, and 4.3 of method 1200 is selected. To reduce the number of candidates more efficiently, it is possible to first find the groups belonging to Cases 1 and 2 and record the spectra of sequences in these groups. Subsequently, find the sequences created by these spectra but presented in other groups, and mark them as the presented sequences. For Case 3, the presented sequences in the grouping can be discarded.

Upon performing peptide sequencing and/or sequence grouping using the computational methods described above, at step 504 of the method 500, the obtained peptide sequences with the determined order can be converted into a digital code by the processor 202. The peptide sequences with the determined order are obtained by sequencing the peptides or the mixture of peptides at step 502. The methods for converting the peptide sequences into the digital code should correspond to the methods for translating the digital code into peptide sequences in the data storage process (step 404 of method 400). In embodiments of the present disclosure, each peptide sequence is formed by amino acids. One or more amino acids are used to represent a bit pattern or symbol pattern in the data storage process. Therefore, in order to convert the peptide sequence into a digital code, one or more amino acids in the peptide sequence are represented by the corresponding bit pattern or symbol pattern. For example, when one symbol in a digital code is mapped to three amino acids to form a peptide sequence at step 404, three amino acids in the peptide sequence shall be reversely mapped to the one symbol to convert the peptide sequences into the digital code at step 504.

At step 506, the digital data can be decoded from the digital code by the processor 202. When error-correction method is used for encoding the digital data, one or more error-correction technique(s) is/are applied to recover the starting digital code. In an example, when a LDPC code is used for encoding the digital data into a digital code, the converted digital code obtained from step 504 is decoded based on LDPC code. The converted digital code contains estimated information bits and estimated parity bits. The estimated parity bits are used to detect and correct errors in the estimated information bits. The correct information bits can therefore be retrieved from the converted digital code. In another example, when order-checking bits are used for encoding the digital data into a digital code, the converted digital code obtained from step 504 is decoded based on the pre-defined rules of generating the order-checking bits. The converted digital code contains redundancy of order-checking bits. The order-checking bits are used to check if certain bit(s)/symbol(s) are in the right order, therefore correcting the wrong orders of bit(s)/symbol(s) to retrieve the correct digital data from the converted digital code. Decoding the digital data from the digital code can use algorithms such as belief-propagation algorithm, message-passing algorithm, sum-product algorithm and bit-flipping algorithm.

In the case when the digital data is encrypted or ciphered before being stored, one or more decryption technique(s) is/are applied to the reverse-mapped bits/symbols to recover the original digital data. In the case when the digital data and/or the encoded digital code are interleaved before being stored, one or more deinterleaved technique(s) is/are applied to the reverse-mapped bits/symbols to recover the original digital data.

Figure 7:
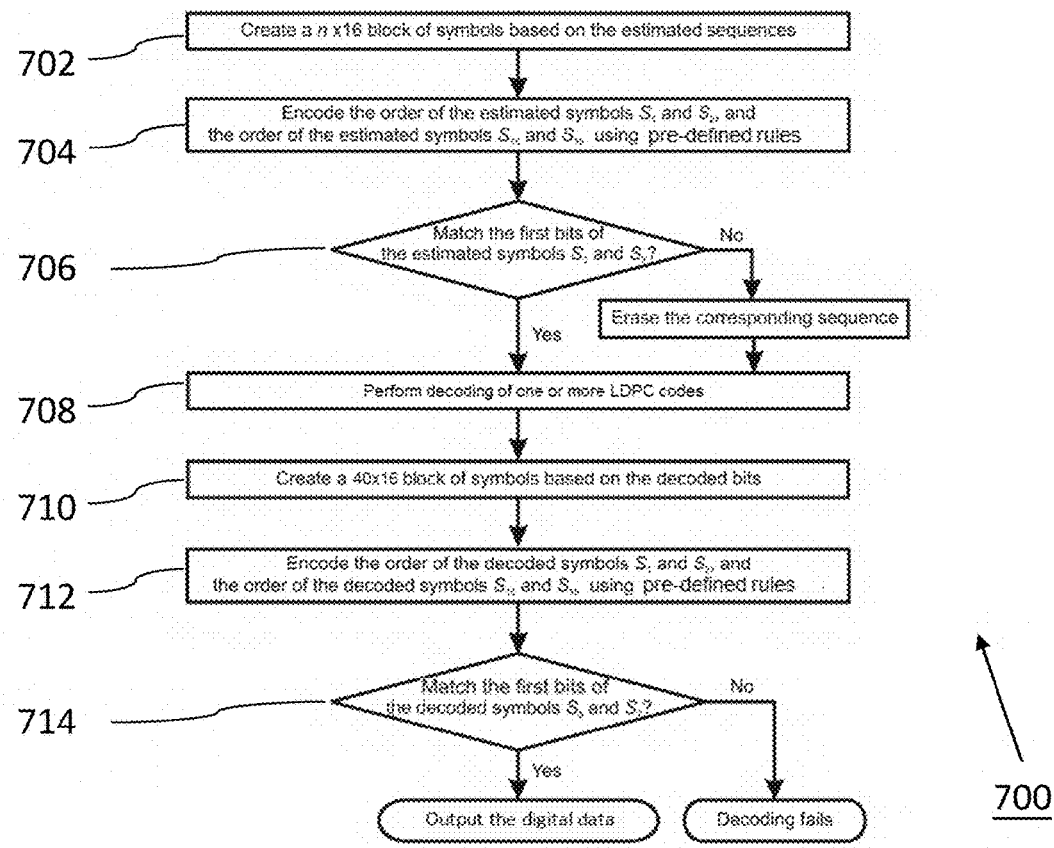
FIG. 7 depicts a flowchart illustrating a method of decoding digital data from a digital code, the digital code including order-checking bits and one or more LDPC codes, in accordance with embodiments of the disclosure.

FIG. 7 shows a flowchart illustrating a method 700 for decoding digital data from a digital code used at step 506. The digital code includes order-checking bits and one or more LDPC codes. After performing step 502 and 504, the system 200 obtains a digital code converted from an order of estimated peptide sequences. At step 702, the system 200 creates a n×16 block of symbols based on the estimated sequences. In some embodiments, the converted digital code contains bit(s)/symbol(s) that indicate the addresses or positions of the estimated peptide sequences in the block of symbols. The information relating to the addresses or positions of the estimated peptide sequences is used to arrange the estimated peptide sequences in a right order in the block of symbols. The 16 symbols in each sequence are denoted as $S_1, S_2, \ldots, S_{16}$. At step 704, according to the orders of the estimated symbol pairs $\{S_1, S_2\}$ and $\{S_{15}, S_{16}\}$, the order-checking bits are generated based on pre-defined rules. At step 706, the order-checking bits are compared against the corresponding first bits of the estimated symbols $S_3$ and $S_7$ to see if they are identical. As an example, if there is no error in the orders of $S_1$ and $S_2$, the generated order-checking bit for $\{S_1, S_2\}$ should match the first bit of the estimated symbol $S_3$. If the generated order-checking bits do not match the first bit of $S_3$ and/or $S_7$ in an estimated sequence, the estimated sequence in the block should be erased.

On the condition that the generated order-checking bits match the first bits of the estimated symbols $S_3$ and $S_7$, method 700 proceeds from step 706 to step 708. At step 708, the bits in the estimated symbols $S_3$-$S_{16}$ of the block are passed to the decoders of the LDPC codes to perform decoding of LDPC code. At step 710, the system 200 outputs a 40×16 block of symbols using the decoded bits of the LDPC codes. Similarly to step 704, order-checking bits are generated based on pre-defined rules at step 712 according to the decoded symbols pairs $\{S_1, S_2\}$ and $\{S_{15}, S_{16}\}$. At step 714, the order-checking bits are compared against the corresponding first bits of the decoded symbol $S_3$ and $S_7$ to see if they are identical. If not, the system 200 reports a detected error and indicates that the decoding fails. If yes, the system 200 outputs the decoded sequences.

Example: Retrieving Digital Data from Peptide Sequences

Figure 9B:
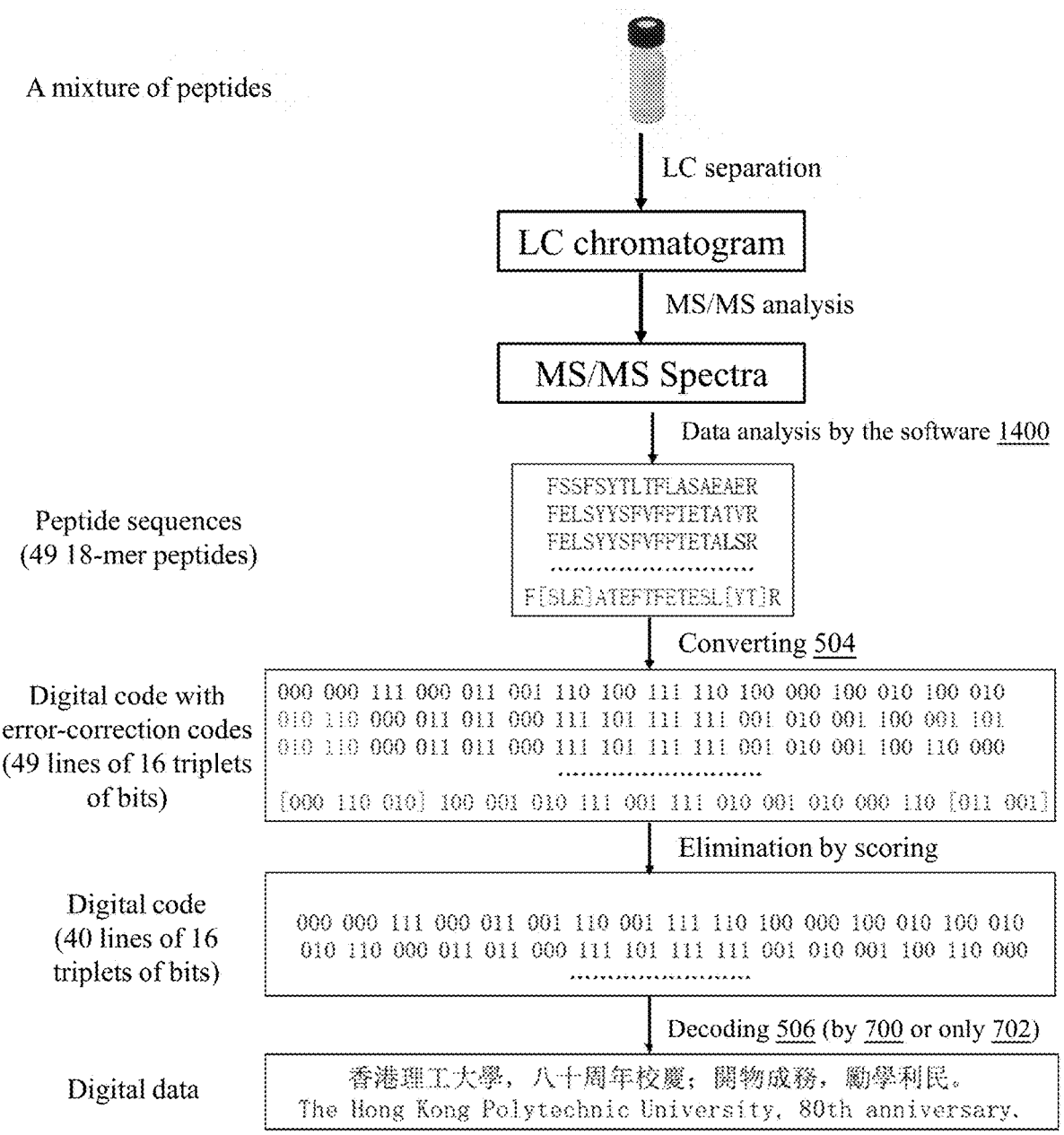

Referring to FIGS. 9A and 9B, illustrations 900 and 950 of retrieving digital data from peptide sequences in accordance with embodiments of the disclosure is depicted. Performing step 502 of method 500, the stored mixture is first analyzed by LC-MS/MS. A 15 cm C18 column is used for ultrahigh pressure liquid chromatography (UPLC) separation, with the elution gradient changed from 95% solution A (0.2% formic acid in water) to 99% solution B (0.2% formic acid in acetonitrile). The MS analysis is performed on an orbitrap mass spectrometer coupled with the UPLC. A non-target strategy with m/z limits of 700-1500 and peptide isotopic pattern recognition are used to select ions for MS/MS analysis. High-energy collisional dissociation (HCD) and electron-capture dissociation (ECD) are performed in parallel to produce MS/MS spectra. A total of 90 spectra are produced.

In one embodiment (FIG. 9A), when two-stage sequencing method 1200 is used, among 90 spectra, there are 6 spectra without output sequences and another 6 spectra without length of 16, which are discarded in the sequence grouping. The sequences have length of 16 because the head and tail amino acids are excluded for simplicity. Excluding duplicate sequences, there are 43 distinct sequences with length of 16. After grouping based on the scores, 40 sequences are obtained corresponding to 40 groups with address pairs of {000 000}, {000 001}, {000 010}, ..., {100 110}, {100 111}. Performing step 504 of method 500, these peptide sequences are converted into a digital code or equivalent symbols. The reverse-mapping method used is amino-acid-to-bits reverse mapping, in which an amino acid is reversely mapped to a triplet of bits. Because the amino acid F at the N-terminal and the amino acid R at the C-terminal do not carry any information, only the 16 amino acids in the 18-mer peptide sequences are converted to digital code or equivalent symbols. The digital code is decoded by performing step 506 of method 500 and method 700. In method 700, the order of the first two amino acids and the order of the last two amino acids are checked using the first bits of $S_3$ and $S_7$, respectively, in accordance with the encoding rules of the order-checking bits. If the bits generated according to the order-checking rules using the first two amino acids and the last two amino acids do not match the first bits of $S_3$ or $S_7$ respectively, then the corresponding sequence will be erased. Finally, a 40×16 block of symbols can be constructed. The error-correction method confirms the correct sequence assignment of 38 peptides, corrected 2 peptides, and excluded 3 impurity peptides. These corrected codes are further decoded to original data, with 100% retrieval. The data density of peptides for data storage in this preliminary study is ~$10^{10}$ bits/g, estimated from the injection volume of 3 L and peptide concentration of about 1 M.

In another embodiment (FIG. 9B), the highest-intensity-tag based sequencing method 1400 is used. Among the 90 spectra, 9 spectra cannot produce any valid sequence, 4 spectra produce valid sequences of length not equal to 16, and the remaining 77 spectra produce a total of 89 valid sequences. Thus, some of the groups have multiple sequences generated by the same or different spectra. Excluding duplicate sequences, there are 49 distinct sequences with length of 16. The sequence grouping method described in paragraphs [0126]-[0128] is used to obtain 40 groups, each with only one sequence. Step 506 of method 500 is performed to decode. Performing method 700 or step 702 of method 700, the correctness of all 40 sequences are confirmed, showing that all sequences in the group are correct even without performing order-checking and error-correction processes of steps 704-714, leading to 100% retrieval of the original data.

The data density may be further improved significantly since MS/MS sequencing of peptides with much smaller amounts, e.g., sub-attomole, could be achieved. At this detection limit, it is estimated at least $10^{16}$ bits/g could be achieved with the same setup.

FIG. 3 depicts an exemplary computing device 300, hereinafter interchangeably referred to as a computer system 300, where one or more such computing devices 300 may be used to execute the methods 400, 500, 600 and 700 of FIGS. 4, 5, 6 and 7. One or more components of the exemplary computing device 300 can also be used to implement the systems 100, 200 as well as the synthesizer 112 and the sequencer 212. The following description of the computing device 300 is provided by way of example only and is not intended to be limiting.

As shown in FIG. 3, the example computing device 300 includes a processor 302 for executing software routines. Although a single processor is shown for the sake of clarity, the computing device 300 may also include a multi-processor system. The processor 302 is connected to a communication infrastructure 306 for communication with other components of the computing device 300. The communication infrastructure 306 may include, for example, a communications bus, cross-bar, or network.

The computing device 300 further includes a main memory 304, such as a random access memory (RAM), and a secondary memory 310. The secondary memory 310 may include, for example, a storage drive 312, which may be a hard disk drive, a solid state drive or a hybrid drive and/or a removable storage drive 314, which may include a magnetic tape drive, an optical disk drive, a solid state storage drive (such as a USB flash drive, a flash memory device, a solid state drive or a memory card), or the like. The removable storage drive 314 reads from and/or writes to a removable storage medium 318 in a well-known manner. The removable storage medium 318 may include magnetic tape, optical disk, non-volatile memory storage medium, or the like, which is read by and written to by removable storage drive 314. As will be appreciated by persons skilled in the relevant art(s), the removable storage medium 318 includes a computer readable storage medium having stored therein computer executable program code instructions and/or data.

In an alternative implementation, the secondary memory 310 may additionally or alternatively include other similar means for allowing computer programs or other instructions to be loaded into the computing device 300. Such means can include, for example, a removable storage unit 322 and an interface 320. Examples of a removable storage unit 322 and interface 320 include a program cartridge and cartridge interface (such as that found in video game console devices), a removable memory chip (such as an EPROM or PROM) and associated socket, a removable solid state storage drive (such as a USB flash drive, a flash memory device, a solid state drive or a memory card), and other removable storage units 322 and interfaces 320 which allow software and data to be transferred from the removable storage unit 322 to the computer system 300.

The computing device 300 also includes at least one communication interface 324. The communication interface 324 allows software and data to be transferred between computing device 300 and external devices via a communication path 326. In various embodiments of the disclosure, the communication interface 324 permits data to be transferred between the computing device 300 and a data communication network, such as a public data or private data communication network. The communication interface 324 may be used to exchange data between different computing devices 300 which such computing devices 300 form part an interconnected computer network. Examples of a communication interface 324 can include a modem, a network interface (such as an Ethernet card), a communication port (such as a serial, parallel, printer, GPIB, IEEE 1394, RJ45, USB), an antenna with associated circuitry and the like. The communication interface 324 may be wired or may be wireless. Software and data transferred via the communication interface 324 are in the form of signals which can be electronic, electromagnetic, optical or other signals capable of being received by communication interface 324. These signals are provided to the communication interface via the communication path 326.

As used herein, the term "computer program product" may refer, in part, to removable storage medium 318, removable storage unit 322, a hard disk installed in storage drive 312, or a carrier wave carrying software over communication path 326 (wireless link or cable) to communication interface 324. Computer readable storage media refers to any non-transitory, non-volatile tangible storage medium that provides recorded instructions and/or data to the computing device 300 for execution and/or processing. Examples of such storage media include magnetic tape, CD-ROM, DVD, Blu-ray™ Disc, a hard disk drive, a ROM or integrated circuit, a solid state storage drive (such as a USB flash drive, a flash memory device, a solid state drive or a memory card), a hybrid drive, a magneto-optical disk, or a computer readable card such as a PCMCIA card and the like, whether or not such devices are internal or external of the computing device 300. Examples of transitory or non-tangible computer readable transmission media that may also participate in the provision of software, application programs, instructions and/or data to the computing device 300 include radio or infra-red transmission channels as well as a network connection to another computer or networked device, and the Internet or Intranets including e-mail transmissions and information recorded on Websites and the like.

The computer programs (also called computer program code) are stored in main memory 304 and/or secondary memory 310. Computer programs can also be received via the communication interface 324. Such computer programs, when executed, enable the computing device 300 to perform one or more features of embodiments discussed herein. In various embodiments, the computer programs, when executed, enable the processor 302 to perform features of the above-described embodiments. Accordingly, such computer programs represent controllers of the computer system 300.

Software may be stored in a computer program product and loaded into the computing device 300 using the removable storage drive 314, the storage drive 312, or the interface 320. The computer program product may be a non-transitory computer readable medium. Alternatively, the computer program product may be downloaded to the computer system 300 over the communication path 326. The software, when executed by the processor 302, causes the computing device 300 to perform the necessary operations to execute the methods 400, 500, 600, and 700 as shown in FIGS. 4, 5, 6 and 7.

It is to be understood that the embodiment of FIG. 3 is presented merely by way of example to explain the operation and structure of the system 300. Therefore, in some embodiments one or more features of the computing device 300 may be omitted. Also, in some embodiments, one or more features of the computing device 300 may be combined together. Additionally, in some embodiments, one or more features of the computing device 300 may be split into one or more component parts.

It will be appreciated that the elements illustrated in FIG. 3 function to provide means for performing the various functions and operations of the system as described in the above embodiments.

When the computing device 300 is configured to realize the system 100 to store digital data into peptide sequences, the system 100 will have a non-transitory computer readable medium having stored thereon an application which when executed causes the system 100 to perform steps comprising: (i) encoding digital data into a digital code; (ii) translating the digital code into peptide sequences; and (iii) synthesizing the translated peptide sequences. When the computing device 300 is configured to realize the system 200 to retrieve digital data from peptide sequences, the system 200 will have a non-transitory computer readable medium having stored thereon an application which when executed causes the system 200 to perform steps comprising: (i) sequencing and determining an order of the peptide sequences; (ii) converting the peptide sequences with the determined order into a digital code; and (iii) decoding the digital data from the digital code.

It will be appreciated by a person skilled in the art that numerous variations and/or modifications may be made to the present disclosure as shown in the specific embodiments without departing from the spirit or scope of the disclosure as broadly described. The present embodiments are, therefore, to be considered in all respects to be illustrative and not restrictive.

What is claimed:

1. A method of storing digital data into one or more peptide sequences, the method comprising:
    encoding the digital data into a digital code;
    translating the digital code into the one or more peptide sequences, wherein translating the digital code comprises mapping a bit pattern or a symbol pattern into one or more amino acids such that the digital code is represented by a sequence of amino acids in the one or more peptide sequences; and wherein each of the one or more peptide sequences independently comprises a N-terminal amino acid covalently bonded via an internal amino acid sequence to a C-terminal amino acid, wherein the C-terminal amino acid is a basic amino acid; and
    providing the one or more translated peptide sequences, with the proviso that if the one or more peptide sequences comprise two or more amino acids with identical molecular weights, then the two or more amino acids have the same mapped bit pattern or symbol pattern.

2. The method of claim 1, wherein the N-terminal amino acid of each of the one or more translated peptide sequences is the same; and the C-terminal amino acid of each of the one or more translated peptide sequences is the same.

3. The method of claim 1, wherein each of the one or more translated peptide sequences independently consists of 8-30 amino acids.

4. The method of claim 1, wherein each of the one or more translated peptide sequences contains no more than one basic amino acid.

5. The method of claim 1, wherein each of the one or more translated peptide sequences contains no more than one basic amino acid independently selected from the group consisting of lysine, arginine, histidine, 1,2-diaminoethane, and 1,3-diaminopropane (DAP).

6. The method of claim 1, wherein the N-terminal of each of the one or more translated peptide sequences is selected from the group consisting of serine, threonine, histidine, lysine, aspartic acid, and glutamic acid.

7. The method of claim 1, wherein the C-terminus of each of the one or more translated peptide sequences is selected from the group consisting of lysine, arginine, histidine, 1,2-diaminoethane, and DAP.

8. The method of claim 1, wherein each of the internal amino acid sequences do not comprise histidine, lysine, arginine, or aspartic acid.

9. The method of claim 1, wherein each of the one or more translated peptide sequences do not comprises cysteine, tryptophan, methionine, asparagine, or glutamine.

10. The method of claim 1, wherein the step of providing the translated peptide sequences comprises synthesizing the translated peptide sequences.

11. The method of claim 1, wherein the translating of the digital code into peptide sequences comprises:
mapping a bit pattern or a symbol pattern into one or more amino acids such that the digital code is represented by a sequence of amino acids in the one or more peptide sequences.

12. The method of claim 1 further comprising adding one or more order-checking bits into the digital code, wherein the one or more order-checking bits are related to the order of the bits or symbols in the digital code.

13. The method of claim 12, wherein the translating of the digital code into peptide sequences comprises: mapping a bit pattern or a symbol pattern into one or more amino acids such that the digital code is represented by a sequence of amino acids in the one or more peptide sequences; each of the one or more peptide sequences independently consists of 17-24 amino acids; each of the one or more peptide sequences contains one basic amino acid located at the C-terminus of each of the one or more peptide sequences selected from the group consisting of DAP and arginine; the N-terminal of each of the one or more peptide sequences is selected from the group consisting of serine, threonine, aspartic acid, and glutamic acid; each of the internal amino acid sequences do not comprise histidine, lysine, arginine, or aspartic acid; and each of the one or more peptide sequences do not comprises cysteine, tryptophan, methionine, asparagine, or glutamine.

14. A method of retrieving digital data from one or more peptide sequences, wherein the retrieving digital data from the one or more peptide sequences comprises:
sequencing and determining an order of the one or more peptide sequences, wherein each of the one or more peptide sequences independently comprises a N-terminal amino acid covalently bonded via an internal amino acid sequence to a C-terminal amino acid, wherein the C-terminal amino acid is a basic amino acid; and wherein the step of sequencing and determining an order of the one or more peptide sequences comprises a mass spectroscopy method;
converting the one or more peptide sequences with the determined order into a digital code wherein the converting of the peptide sequences with the determined order into the digital code comprises mapping one or more amino acids in the peptide sequences into a bit pattern or a symbol pattern such that the digital code is obtained from a sequence of amino acids in the peptide sequences with the determined order; and
decoding the digital data from the digital code, with the proviso that if the one or more peptide sequences comprise two or more amino acids with identical molecular weights, then the two or more amino acids have the same mapped bit pattern or symbol pattern.

15. The method of claim 14, wherein the step of sequencing the one or more peptide sequences comprises a sequencing method selected from the group consisting of a graph theory model and a highest-intensity tag based model.

16. The method of claim 14, wherein the mass spectroscopy method comprises matrix assisted laser desorption ionization mass spectrometry or liquid chromatograph-mass spectrometry/mass spectrometry.

17. The method of claim 14, wherein the N-terminal amino acid of each of the one or more translated peptide sequences is the same; and the C-terminal amino acid of each of the one or more translated peptide sequences is the same.

18. The method of claim 14, wherein each of the one or more translated peptide sequences independently consists of 8-30 amino acids.

19. The method of claim 14, wherein each of the one or more translated peptide sequences contains no more than one basic amino acid.

20. The method of claim 14, wherein each of the one or more translated peptide sequences contains no more than one basic amino acid independently selected from the group consisting of lysine, arginine, histidine, 1,2-diaminoethane, and DAP.

21. The method of claim 14, wherein the N-terminal of each of the one or more translated peptide sequences is selected from the group consisting of serine, threonine, histidine, lysine, aspartic acid, and glutamic acid.

22. The method of claim 14, wherein the C-terminus of each of the one or more translated peptide sequences is selected from the group consisting of lysine, arginine, histidine, 1,2-diaminoethane, and DAP.

23. The method of claim 14, wherein each of the internal amino acid sequences do not comprise histidine, lysine, arginine, or aspartic acid.

24. The method of claim 14, wherein each of the one or more translated peptide sequences do not comprises cysteine, tryptophan, methionine, asparagine, or glutamine.

25. The method of claim 14, wherein the digital code comprises one or more order-checking bits, wherein the one or more order-checking bits are related to the order of the bits or symbols in the digital code.

26. The method of claim 25, wherein the step of sequencing the one or more peptide sequences comprises a sequencing method selected from the group consisting of a graph theory model and a highest-intensity tag based model; the mass spectroscopy method comprises matrix assisted laser desorption ionization mass spectrometry or liquid chromatograph-mass spectrometry/mass spectrometry; each of the one or more peptide sequences independently consists of 17-24 amino acids; each of the one or more peptide sequences contains one basic amino acid located at the C-terminus of each of the one or more peptide sequences selected from the group consisting of DAP and arginine; the N-terminal of each of the one or more peptide sequences is selected from the group consisting of serine, threonine, aspartic acid, and glutamic acid; each of the internal amino acid sequences do not comprise histidine, lysine, arginine, or aspartic acid; and each of the one or more peptide sequences do not comprises cysteine, tryptophan, methionine, asparagine, or glutamine.

27. A system for storing digital data into one or more peptide sequences, the system comprising:
a synthesizer configured to synthesize the one or more peptide sequences;
at least one processor in communication with the synthesizer; and
at least one memory including computer program code, the at least one memory and the computer program code configured to, with the at least one processor, cause the system at least to:

encode the digital data into a digital code;

translate the digital code into one or more peptide sequences, wherein translating the digital code comprises mapping a bit pattern or a symbol pattern into one or more amino acids such that the digital code is represented by a sequence of amino acids in the one or more peptide sequences, with the proviso that if the one or more peptide sequences comprise two or more amino acids with identical molecular weights, then the two or more amino acids have the same mapped bit pattern or symbol pattern; wherein each of the one or more translated peptide sequences independently comprises a N-terminal amino acid covalently bonded via an internal amino acid sequence to a C-terminal amino acid, and wherein the C-terminal amino acid is a basic amino acid; and synthesize the one or more translated peptide sequences using the synthesizer.

28. A system for retrieving digital data from one or more peptide sequences, the system comprising:

a mass spectrometer configured to sequence and determine an order of the one or more peptide sequences, wherein the mass spectrometer is selected from the group consisting of matrix assisted laser desorption ionization mass spectrometry and liquid chromatography-mass spectrometry/mass spectrometry;

at least one processor in communication with the sequencer; and at least one memory including computer program code, the at least one memory and the computer program code configured to, with the at least one processor, cause the system at least to:

sequence and determine the order of the peptide sequences using the mass spectrometer, wherein the step of sequencing and determining the order of the one or more peptide sequences comprises a sequencing method selected from the group consisting of a graph theory model and a highest-intensity tag based model;

convert the one or more peptide sequences with the determined order into a digital code, wherein converting the one or more peptide sequences with the determined order into the digital code comprises mapping one or more amino acids in the peptide sequences into a bit pattern or a symbol pattern such that the digital code is obtained from a sequence of amino acids in the peptide sequences with the determined order, wherein each of the one or more peptide sequences independently comprises a N-terminal amino acid covalently bonded via an internal amino acid sequence to a C-terminal amino acid, and wherein the C-terminal amino acid is a basic amino acid, with the proviso that if the one or more peptide sequences comprise two or more amino acids with identical molecular weights, then the two or more amino acids have the same mapped bit pattern or symbol pattern; and decode the digital data from the digital code.

* * * * *